United States Patent [19]

Keana et al.

[11] Patent Number: 5,801,183
[45] Date of Patent: Sep. 1, 1998

[54] AZA AND AZA (N-OXY) ANALOGS OF GLYCINE/NMDA RECEPTOR ANTAGONISTS

[75] Inventors: John F. W. Keana, Eugene, Oreg.; Sui Xiong Cai, Foothill Ranch, Calif.; Zhang-Lin Zhou; James M. Navratil, both of Eugene, Oreg.

[73] Assignees: State of Oregon, Acting by and Through the Oregon State Board of Higher Education, Acting for and on Behalf of the Oregon Health Sciences University and the University of Oregon, Eugene, Oreg.; Cocensys, Inc., Irvine, Calif.

[21] Appl. No.: 466,043

[22] Filed: Jun. 6, 1995

Related U.S. Application Data

[63] Continuation-in-part of Ser. No. 379,699, Jan. 27, 1995, abandoned.

[51] Int. Cl.$^6$ ...................... A61K 31/435; C07D 471/04
[52] U.S. Cl. .......................... 514/300; 546/122; 546/123
[58] Field of Search ................................ 546/123, 122; 514/300

[56] References Cited

U.S. PATENT DOCUMENTS

| | | | |
|---|---|---|---|
| 4,103,257 | 7/1978 | Hammond | 331/94.5 L |
| 4,128,649 | 12/1978 | Hardtmann | 424/256 |
| 4,215,123 | 7/1980 | Scotese | 424/256 |
| 5,055,465 | 10/1991 | Davey | 514/228.2 |
| 5,196,421 | 3/1993 | McQuaid et al. | 514/250 |
| 5,252,584 | 10/1993 | Carling et al. | 514/312 |
| 5,268,378 | 12/1993 | Baker et al. | 514/312 |
| 5,283,244 | 2/1994 | Sakamoto et al. | 514/249 |
| 5,424,311 | 6/1995 | Billhardt-Troughton et al. | 514/248 |

FOREIGN PATENT DOCUMENTS

| | | |
|---|---|---|
| 0 459 561 | 12/1991 | European Pat. Off. |
| 516392 | 12/1992 | European Pat. Off. |
| 4-178385 | 6/1992 | Japan |
| 1490998 | 11/1977 | United Kingdom |
| WO 92/07847 | 5/1992 | WIPO |
| WO 94/00124 | 1/1994 | WIPO |
| WO 94/20470 | 9/1994 | WIPO |
| WO 94/27605 | 12/1994 | WIPO |

OTHER PUBLICATIONS

Bigge, C.F., "Structural Requirements for the Development of Potent N-Methly-D-Aspartic Acid (NMDA) Receptor Antagonists", *Biochem. Pharmacol.* 45(8):1547-1561 (Apr. 22, 1993).

Bigge, C.F. and Boxer, P.A., "Neuronal Cell Death and Strategies for Neuroprotection", in: *Annual Reports in Medicinal Chemistry*, vol. 29, McCall (Ed.), San Diego: Academic Press, Inc., pp. 13-22 (Aug. 24, 1994).

Carling, R.W. et al., "3-Nitro-3, 4-dihydro-2(1H)-quinolones. Excitatory Amino Acid Antagonists Acting at Glycine-Site NMDA and (RS)-α-Amino-3-hydroxy-5-methyl-4-isoxazolepropionic Acid Recepetors", *J. Med. Chem.* 36:3397-3408 (1993).

Gray, N.M. et al., "Novel Indole-2-carboxylates as Ligands for the Strychnine-Insensitive N-Methyl-D-aspartate-Linked Glycine Receptor", *J. Med. Chem.* 34:1283-1292 (1991).

Kaye, I.A., "Some Substituted Pyrido(2,3)pyrazines", *J. Med. Chem.* 7:240-241 (Mar., 1964).

Kessler, M. et al., "A Glycine Site Associated with N-Methyl-D-Aspartic Acid Receptors: Characterization and Identification of a New Class of Antagonists", *J. Neurochem.* 52(4):1319-1328 (1989).

Kulagowski et al., "3'-(Arylmethyl)- and 3'-(Aryloxy)-3-phenyl-4-hydroxyquinolin-2(1H)-ones: Orally Active Antagonists of the Glycine Site on the NMDA Receptor", *J. Med. Chem.* 37:1402-1405 (May 13, 1994).

Leeson, P.D. et al., "Amino Acid Bioisosteres: Design of 2-Quinoline Derivatives as Glycine-Site N-Methyl-D-Aspartate Receptor Antagonists", *Bioorg. Med. Chem. Lett.* 3(2):299-304 (1993).

Leeson, P.D., "Glycine-Site N-Methyl-D-Aspartate Receptor Antagonists", in: *Drug Design for Neuroscience*, Kozikowski, A.P. (Ed.), New York: Raven Press, Ltd., pp. 339-381 (1993).

Leeson, P.D. and Iversen, L.L., "The Glycine Site on the NMDA Receptor: Structure-Activity Relationships and Therapeutic Potential", *J. Med. Chem.* 37(24):4053-4067 (Nov. 25, 1994).

Lipton, S.A., "Prospects for Clinically Tolerated NMDA Antagonists: Open-Channel Blockers and Alternative Redox States of Nitric Oxide", *Trends in Neurosci.* 16(12):527-532 (Dec., 1993).

Lipton, S.A. and Rosenberg, P.A., "Excitatory Amino Acids as a Final Common Pathway for Neurologic Disorders", *New Engl. J. Med.* 330(9):613-622 (Mar. 3, 1994).

McQuaid, L.A. et al., "Synthesis and Excitatory Amino Acid Pharmacology of a Series of Heterocyclic-Fused Quinoxalinones and Quinazolinones", *J. Med. Chem.* 35:3319-3324 (1992).

(List continued on next page.)

*Primary Examiner*—C. Warren Ivy
*Assistant Examiner*—Evelyn Huang
*Attorney, Agent, or Firm*—Sterne, Kessler, Goldstein & Fox P.L.L.C.

[57] ABSTRACT

Methods of treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease, and Down's syndrome, treating or preventing adverse consequences of the hyperactivity of the excitatory amino acids, as well as treating anxiety, chronic pain, convulsions, inducing anesthesia, and treating or preventing opiate tolerance are disclosed by administering to an animal in need of such treatment or prevention a substituted or unsubstituted pyridine and pyridine (N-oxide) analogs of 4-hydroxydihydroquinolones, tetrahydroquinoline-trione-oximes and quinoxalones, tautomers and pharmaceutically acceptable salts thereof, which have high binding to the glycine receptor.

33 Claims, No Drawings

OTHER PUBLICATIONS

Monn, J.A. and Schoepp, D.D., "Recent Progress in Excitatory Amino Acid Research", in: *Annual Reports in Medicinal Chemistry*, vol. 29, McCall (Ed.), San Diego: Academic Press, Inc., pp. 53–64 (Aug. 24, 1994).

Rowley, M., "3–Acyl–4–hydroxyquinolin–2(1H)–ones. Systemically Active Anticonvulsants Acting by Antagonism as the Glycine Site of the N–Methyl–D–Aspartate Receptor Complex", *J. Med. Chem.* 36:3386–3396 (1993).

Sakamoto, S. et al., "Preparation of Diketopiperazines as Glutamate Receptor Antagonists", *Chem. Abstr.* 117:695, Abstract No. 251367d (1992).

Winterfeld, K. and Wildersohn, M., "2,3–Dichlor–und 2,3,7–Trichlor–5–aza–chinoxalin", *Archiv der Pharmazie* 303(1):44–48 (1970).

Czuba W, Kowalska T, Kowalski P. Pol. J. Chem. 52(12), 2369–76. (abstract), 1978.

Santilli AA, Scotese AC, Bauer RF, Bell SC. J. med. Chem. 30(12), 2270–7. (abstract), 1987.

Mohamed EA, Abdel–Rahman RM, El–Gendy Z, Ismail MM. An.Quim. 89(2), 246–53. (abstract), 1993.

Soliman AY, Bakeer HM. Chin. J. Chem. 9(5), 461–6. (abstract), 1991.

AZA AND AZA (N-OXY) ANALOGS OF GLYCINE/NMDA RECEPTOR ANTAGONISTS

CROSS REFERENCE TO RELATED APPLICATION

This is a continuation-in-part of U.S. application Ser. No. 08/379,699, filed Jan. 27, 1995 abandoned, the contents of which are fully incorporated by reference.

The present invention was made with U.S. government support under grant DA 06726 awarded by the National Institute of Drug Abuse. Therefore, the U.S. Government has certain rights in the invention.

FIELD OF THE INVENTION

The present invention is in the field of medicinal chemistry and relates to compounds that have a high affinity for the glycine binding site, lack PCP side effects, and cross the blood brain barrier at high levels. In particular, the present invention relates to pyridine and pyridine (N-oxide) analogs of 4-hydroxydihydroquinolin-2-ones, and tetrahydroquinoline-trione-oximes, tautomers thereof and pharmaceutically acceptable salts thereof and their use to treat or prevent neuronal degeneration associated with ischemia, pathophysiologic conditions associated with neuronal degeneration, convulsions, anxiety, and chronic pain, as well as to induce anesthesia, treat or prevent psychosis and for preventing opiate tolerance. A further aspect of the present invention employs nitrone analogs of quinoxalone NMDA glycine receptor antagonists, and pyridine and pyridine (N-oxide) derivatives thereof.

BACKGROUND OF THE INVENTION

Glutamate is thought to be the major excitatory neurotransmitter in the brain. There are three major subtypes of glutamate receptors in the CNS. These are commonly referred to as kainate, AMPA, and N-methyl-D-aspartate (NMDA) receptors (Watkins and Olverman, *Trends in Neurosci.* 7:265–272 (1987)). NMDA receptors are found in the membranes of virtually every neuron in the brain. NMDA receptors are ligand-gated cation channels that allow $Na^+$, $K^+$, and $Ca^{++}$ to permeate when they are activated by glutamate or aspartate (non-selective, endogenous agonists) or by NMDA (a selective, synthetic agonist) (Wong & Kemp, *Ann. Rev. Pharmacol. Toxicol.* 31:401–425 (1991)).

Glutamate alone cannot activate the NMDA receptor. In order to become activated by glutamate, the NMDA receptor channel must first bind glycine at a specific, high affinity, glycine binding site that is separate from the glutamate/ NMDA binding site on the receptor protein (Johnson & Ascher, *Nature* 325:329–331 (1987)). Glycine is therefore an obligatory co-agonist at the NMDA receptor/channel complex (Kemp, J. A., et al., *Proc. Natl. Acad. Sci. USA* 85:6547–6550 (1988)).

In addition to the binding sites for glutamate/NMDA and glycine, the NMDA receptor carries a number of other functionally important binding sites. These include binding sites for $Mg^{++}$, $Zn^{++}$, polyamines, arachidonic acid and phencyclidine (PCP) (Reynolds & Miller, *Adv. in Pharmacol.* 21:101–126 (1990); Miller, B., et al., *Nature* 355:722–725 (1992)). The PCP binding site-now commonly referred to as the PCP receptor-is located inside the pore of the ionophore of the NMDA receptor/channel complex (Wong, E. H. F., et al., *Proc. Natl. Acad. Sci. USA* 83:7104–7108 (1986); Huettner and Bean, *Proc. Natl. Acad. Sci. USA* 85:1307–1311 (1988); MacDonald, J. F., et al., *Neurophysiol.* 58:251–266 (1987)). In order for PCP to gain access to the PCP receptor, the channel must first be opened by glutamate and glycine. In the absence of glutamate and glycine, PCP cannot bind to the PCP receptor although some studies have suggested that a small amount of PCP binding can occur even in the absence of glutamate and glycine (Sircar & Zukin, *Brain Res.* 556:280–284 (1991)). Once PCP binds to the PCP receptor, it blocks ion flux through the open channel. Therefore, PCP is an open channel blocker and a non-competitive glutamate antagonist at the NMDA receptor/channel complex.

One of the most potent and selective drugs that bind to the PCP receptor is the anticonvulsant drug MK-801. This drug has a $K_d$ of approximately 3 nM at the PCP receptor (Wong, E. H. F., et al., *Proc. Natl. Acad. Sci. USA* 83:7104–7108 (1986)).

Both PCP and MK-801 as well as other PCP receptor ligands, e.g., dextromethorphan, ketamine and N,N,N'-trisubstituted guanidines, have neuroprotective efficacy both in vitro and in vivo (Gill, R., et al., *J. Neurosci.* 7:3343–3349 (1987); Keana, J. F. W., et al., *Proc. Natl. Acad. Sci. USA* 86:5631–5635 (1989); Steinberg, G. K., et al., *Neuroscience Lett.* 89: 193–197 1988); Church, J., et al., in *Sigma and Phencyclidine-Like Compounds as Molecular Probes in Biology*, Domino & Kamenka, eds., NPP Books, Ann Arbor (1988), pp. 747–756). The well-characterized neuroprotective efficacy of these drugs is largely due to their capacity to block excessive $Ca^{++}$ influx into neurons through NMDA receptor channels, which become over activated by excessive glutamate release in conditions of brain ischemia (e.g., in stroke, cardiac arrest ischemia etc.) (Collins, R. C., *Metabol. Br. Dis.* 1:231–240 (1986); Collins, R. C., et al., *Annals Int. Med.* 110:992–1000 (1989)).

However, the therapeutic potential of these PCP receptor drugs as ischemia rescue agents in stroke has been severely hampered by the fact that these drugs have strong PCP-like behavioral side effects (psychotomimetic behavioral effects) which appear to be due to the interaction of these drugs with the PCP receptor (Tricklebank, M. D., et al., *Eur. J. Pharmacol.* 167:127–135 (1989); Koek, W., et al., *J. Pharmacol. Exp. Ther.* 245:969 (1989); Willets & Balster, *Neuropharmacology* 27:1249 (1988)). These PCP-like behavioral side effects appear to have caused the withdrawal of MK801 from clinical development as an ischemia rescue agent. Furthermore, these PCP receptor ligands appear to have considerable abuse potential as demonstrated by the abuse liability of PCP itself.

The PCP-like behavioral effects of the PCP receptor ligands can be demonstrated in animal models: PCP and related PCP receptor ligands cause a behavioral excitation (hyperlocomotion) in rodents (Tricklebank, M. D., et al., *Eur. J. Pharmacol.* 167:127–135 (1989)) and a characteristic katalepsy in pigeons (Koek, W., et al., *J. Pharmacol. Exp. Ther.* 245:969 (1989); Willets & Balster, *Neuropharmacology* 27:1249 (1988)); in drug discrimination paradigms, there is a strong correlation between the PCP receptor affinity of these drugs and their potency to induce a PCP-appropriate response behavior (Zukin, S. R., et al., *Brain Res.* 294:174 (1984); Brady, K. T., et al., *Science* 215:178 (1982); Tricklebank, M. D., et al., *Eur. J. Pharmacol.* 141:497 (1987)).

Drugs acting as competitive antagonists at the glutamate binding site of the NMDA receptor, such as, CGS 19755 and LY274614, also have neuroprotective efficacy because these drugs—like the PCP receptor ligands—can prevent excessive $Ca^{++}$ flux through NMDA receptor/channels in ischemia (Boast, C. A., et al., *Brain Res.* 442:345–348 (1988); Schoepp, D. D., et al., *J. Neural. Trans.* 85:131–143 (1991)). However, competitive NMDA receptor antagonists also have PCP-like behavioral side-effects in animal models (behavioral excitation, activity in PCP drug discrimination tests) although not as potently as MK-801 and PCP (Tricklebank, M. D., et al., *Eur. J. Pharmacol.* 167:127–135 (1989)).

An alternate way of inhibiting NMDA receptor channel activation is by using antagonists at the glycine binding site of the NMDA receptor. Since glycine must bind to the glycine site in order for glutamate to effect channel opening (Johnson & Ascher, *Nature* 325:329–331 (1987); Kemp, J. A., et al., *Proc. Natl. Acad. Sci. USA* 85:6547–6550 (1988)), a glycine antagonist can completely prevent ion flux through the NMDA receptor channel-even in the presence of a large amount of glutamate.

Recent in vivo microdialysis studies have demonstrated that in the rat focal ischemia model there is a large increase in glutamate release in the ischemic brain region with no significant increase in glycine release (Globus, M. Y. T., et al., *J. Neurochem.* 57:470–478 (1991)). Thus, theoretically, glycine antagonists should be very powerful neuroprotective agents because they can prevent the opening of NMDA channels by glutamate non-competitively and, therefore, unlike competitive NMDA antagonists, do not have to overcome the large concentrations of endogenous glutamate that are released in the ischemic brain region.

Furthermore, because glycine antagonists act at neither the glutamate/NMDA nor the PCP binding sites to prevent NMDA channel opening, these drugs might not cause the PCP-like behavioral side effect seen with both PCP receptor ligands and competitive NMDA receptor antagonists (Tricklebank, M. D., et al., *Eur. J. Pharmacol.* 167:127–135 (1989); Koek, W., et al., *J. Pharmacol. Exp. Ther.* 245:969 (1989); Willets & Balster, *Neuropharmacology* 27:1249 (1988); Zukin, S. R., et al., *Brain Res.* 294:174 (1984); Brady, K. T., et al., *Science* 215:178 (1982); Tricklebank, M. D., et al., *Eur. J. Pharmacol.* 141:497 (1987)). That glycine antagonists may indeed be devoid of PCP-like behavioral side effects has been suggested by recent studies in which available glycine antagonists were injected directly into the brains of rodents without resulting in PCP-like behaviors (Tricklebank, M. D., et al., *Eur. J. Pharmacol.* 167:127–135 (1989)).

For recent reviews on glycine antagonists, reference is made to Leeson, P. D., "Glycine-Site N-Methyl-D-Aspartate Receptor Antagonists," chapter 13 in *Drug Design for Neuroscience*, Kozikowski, A. P., ed., Raven Press, New York (1993), pp. 338–381; and Leeson and Iversen, *J. Med. Chem.* 37: 4053–4067 (1994).

However, there have been two major problems which have prevented the development of glycine antagonists as clinically useful neuroprotective agents:

A. Most available glycine antagonists with relatively high receptor binding affinity in vitro such as 7-Cl-kynurenic acid (Kemp, J. A., et al., *Proc. Natl. Acad. Sci. USA* 85:6547–6550 (1988)), 5,7-dichlorokynurenic acid (McNamara, D., et al., *Neurosci. Lett.* 120:17–20 (1990)) and indole-2-carboxylic acid (Gray, N. M., et al., *J. Med. Chem.* 34:1283–1292 (1991)) cannot penetrate the blood/brain barrier and, therefore, have no utility as therapeutic agents;

B. The only widely available glycine antagonist that sufficiently penetrates the blood/brain barrier—the drug HA-966 (Fletcher & Lodge, *Eur. J. Pharmacol.* 151:161–162 (1988))—is a partial agonist with micromolar affinity for the glycine binding site. A neuroprotective efficacy for HA-966 in vivo has not been demonstrated, nor has it been demonstrated for the other available glycine antagonists because they lack bioavailability in vivo.

However, one recent success in identifying orally active glycine receptor antagonists was reported by Kulagowski et al., *J. Med. Chem.* 37:1402–1405 (1994), who disclose that 3-substituted 4-hydroxyquinoline-2(1H)-ones are selective glycine antagonists possessing potent in vivo activity.

McQuaid, L. A. et al., *J. Med. Chem.* 35:3423–3425 (1992), discloses 3-phenyl-4-hydroxy-1,2-dihydroquinolin-2-ones having the formula:

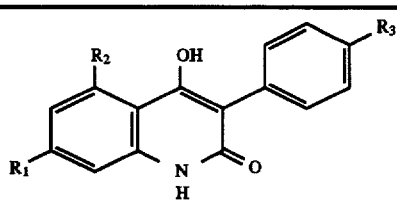

| no. | $R_1$ | $R_2$ | $R_3$ |
|---|---|---|---|
| 7a | H | H | H |
| 7b | Cl | Cl | H |
| 7c | Cl | Cl | $CH_3$ |
| 7d | Cl | Cl | $CH_3O$ |
| 7e | Cl | Cl | $NO_2$ |
| 7f | Cl | Cl | OH |
| 7g | Cl | Cl | $NH_2$ | which are reported to be selective antagonists at the strychnine-insensitive glycine site on the NMDA receptor complex. Kulagowski et al., *J. Med. Chem.*, 37:1402–1405 (1994) teach that compounds of this general formual when $R_1$ is H, $R_2$ is Cl and $R_3$ is H are highly active in vivo. See also Leeson et al., *Bioorg. Med. Chem. Let.*, 3:299–304 (1993). These compounds are hydrophobic and are expected to be hard to administer by the intravenous route since they would be difficult to formulate in an aqueous solution.

Carling et al. in U.S. Pat. No. 5,252,584 disclose a class of 4-hydroxy-2(1H)-quinolone derivatives which are substituted at the 3-position by an N-linked heteroaromatic ring system. The compounds have the general formula:

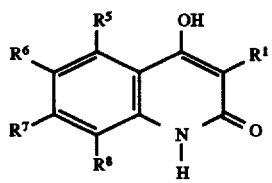

wherein $R^1$ represents a group of formula (i), (ii) or (iii):

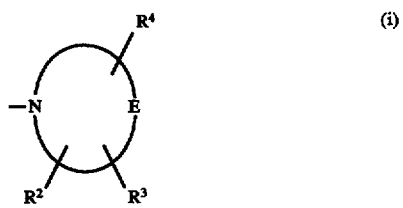

-continued

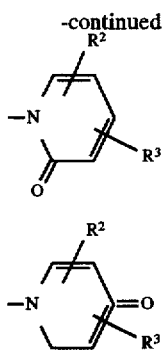

in which the E represents the residue of a 5-membered heteroaromatic ring containing 0, 1, 2, or 3 further nitrogen atoms. These compounds are reportedly useful in the treatment and/or prevention of conditions, in particular neurodegenerative disorders, which require the administration of selective non-competitive antagonists of NMDA receptors.

European Patent Application Publication No. 459,561, published Dec. 12, 1991, discloses 2,4-dioxo-1,2,3,4-tetrahydroquinoline derivatives having the formula:

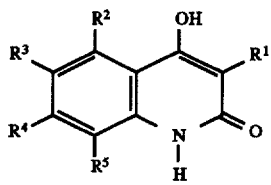

wherein
R$^1$ is a group of part formula (i) or (ii):

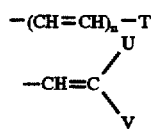

These compounds are reported to be selective non-competitive antagonists of NMDA receptors and are useful in treating neurodegenerative disorders, convulsions and schizophrenia. See also U.S. Pat. No. 5,268,378, to Baker et al., issued Dec. 7, 1993.

International application W094/20470, published Sep. 15, 1994, discloses 4-hydroxy-3-nitro-1,2-dihydroquinoline-2-ones having the formula:

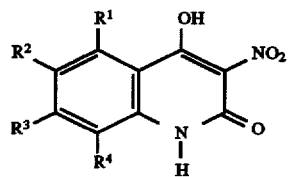

or a pharmaceutically acceptable salt thereof;
wherein
R$_1$–R$_4$ may be hydrogen, nitro, amino, halo, haloalkyl, cyano, alkyl, alkenyl, alkynyl, azido, acylamino, sulfonyl, aryl or alkoxy. This invention resulted from the initial discovery that 4-hydroxy-3-nitro-1,2-dihydroquinolin-2-one exhibits high binding to the glycine receptor. The application discloses methods of treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease and Down's syndrome, treating or preventing the adverse consequences of the overstimulation of the excitatory amino acids, as well as treating anxiety, convulsions, chronic pain and inducing anesthesia, comprising administering the 4-hydroxy-3-nitro-1,2-dihydroquinoline-2-ones to an animal in need of treatment.

International application W094/27605 discloses 1,2,3,4-tetrahydroquinoline-2,3,4-trione-3-oximes and 1,2,3,4-tetrahydroquinoline-2,3,4-trione-4-oximes having the general formula

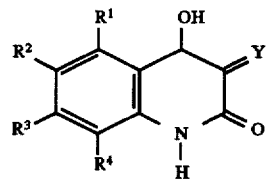

Formula (I)

or a pharmaceutically acceptable salt thereof;
wherein one of X or Y is oxygen and the other of X or Y is N—OR, where R may be hydrogen, alkyl, aryl, heteroaryl, acyl, halogen-substituted acyl or aryloyl. The compounds are useful for treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease and Down's syndrome, treating or preventing the adverse consequences of the overstimulation of the excitatory amino acids, as well as treating anxiety, convulsions, chronic pain, psychosis and inducing anesthesia.

A need continues to exist for potent and selective glycine/NMDA antagonists which can penetrate the blood/brain barrier and which:

- lack the PCP-like behavioral side effects common to the PCP-like NMDA channel blockers, such as MK801, or to the competitive NMDA receptor antagonists, such as CGS19755;
- show potent anti-ischemic efficacy because of the non-competitive nature of their glutamate antagonism at the NMDA receptor;
- have utility as novel anticonvulsants with fewer side-effects than the PCP-like NMDA channel blockers or the competitive NMDA antagonists;
- help in defining the functional significance of the glycine binding site of the NMDA receptor in vivo.

Additional requirements for clinically useful glycine/NMDA antagonists are high water solubility and a relatively low degree of binding to plasma proteins. Good water solubility is desirable so that the glycine/NMDA antagonists can be formulated into an aqueous solution for i.v. administration. Antagonists which have a relatively low degree of binding to plasma protein are desirable so that bioavailability is not reduced.

SUMMARY OF THE INVENTION

The invention relates to a method of treating or preventing neuronal loss associated with stroke, ischemia, CNS trauma, hypoglycemia, and surgery, as well as treating neurodegenerative diseases including Alzheimer's disease, amyotrophic lateral sclerosis, Huntington's disease, and Down's syndrome, treating or preventing the adverse consequences of the overstimulation of the excitatory amino acids, as well as treating anxiety, convulsions, chronic pain, psychosis, inducing anesthesia, and preventing opiate tolerance, comprising administering to an animal in need of such treatment a compound of the Formulae (I–III)

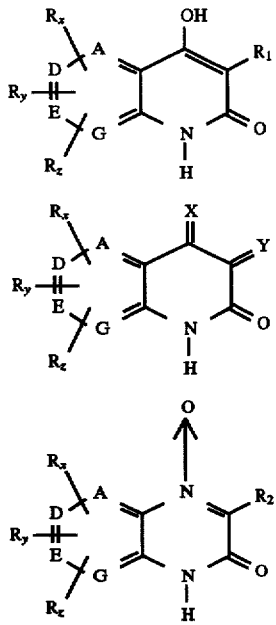

or tautomers or pharmaceutically acceptable salts thereof; wherein

A, D, B and G independently represent carbon or nitrogen, provided that at least two of A, D, B and G represent carbon, one or two of A, D, B and G represent nitrogen, wherein said nitrogen is optionally present as an N-oxide;

$R_x$, $R_y$ and $R_z$ represent two or three substituents not exceeding the maximum permissible by the disposition of nitrogen atoms in the combination A, D, B and G, which substituents independently represent hydrogen, nitro, amino, halo, haloalkyl, cyano, cyanamido, dicyanomethyl, alkyl, cycloalkyl, alkenyl, alkynyl, azido, hydroxy, carboxy, acylamino, alkylsulfonyl, alkylthio, aryl, substituted aryl, heteroaryl, alkoxy, trialkylsilyl-substituted alkoxy, aryloxy, substituted aryloxy, heteroaryloxy, a heterocyclic group, a heterocyclicoxy group, aralkoxy or haloalkoxy, provided that when G is carbon, G may only be substituted by one of hydrogen or fluorine;

$R_1$ represents nitro, cyano, trifluoromethyl, trifluoromethylsulfonyl, 1-alkynyl, —COR, —CO$_2$R, —C(O)SR, cyanamido, tricyanomethyl, —N(CN)$_2$, —C(CN)$_2$—R, —C(=C(CN)$_2$)—R, optionally substituted phenyl or optionally substituted heteroaryl;

$R_2$ represents nitro, cyano, trifluoromethyl, trifluoromethylsulfonyl, 1-alkynyl, —COR, —CO$_2$R, —C(O)SR, —CHR'R", —NHR, —NHC(O)R, cyanamido, tricyanomethyl, —N(CN)$_2$, —C(CN)$_2$—R, —C(=C(CN)$_2$)—R, optionally substituted phenyl or optionally substituted heteroaryl;

R' represents nitro, nitroso, acyl or cyano;

R" represents hydrogen, acyl, alkyl, cycloalkyl, alkenyl, aryl, substituted aryl, cyano, nitro or nitroso;

R represents hydrogen, alkyl, alkenyl, alkynyl, cycloalkyl, arylalkyl, arylalkenyl, arylalkynyl, heteroaryl, heteroarylalkyl or heteroarylalkenyl, any of which groups may be optionally substituted; and one of X or Y represents oxygen and the other of X or Y represents N—OR$_9$, wherein R$_9$ represents hydrogen, alkyl, aryl, heteroaryl, acyl, halogen-substituted acyl or aryloyl.

The invention also relates to novel compounds having the Formulae (I–III) recited above, or a tautomer thereof or a pharmaceutically acceptable salt thereof.

Another aspect of the present invention relates to nitrone analogs of quinoxalone NMDA glycine receptor antagonists having the formula:

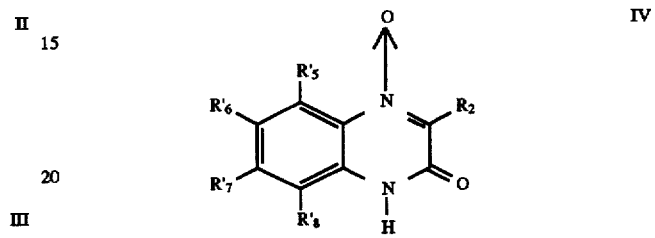

or tautomers or pharmaceutically acceptable salts thereof; wherein

R'$_5$, R'$_6$ and R'$_7$ independently represent hydrogen, nitro, amino, halo, haloalkyl, cyano, alkyl, cycloalkyl, alkenyl, alkynyl, azido, hydroxy, carboxy, acylamino, alkylsulfonyl, alkylthio, aryl, substituted aryl, heteroaryl, alkoxy, trialkylsilyl-substituted alkoxy, aryloxy, substituted aryloxy, heteroaryloxy, a heterocyclic group, a heterocyclicoxy group, aralkoxy or haloalkoxy;

R'$_8$ represents one of hydrogen or fluorine;

R$_2$ represents nitro, cyano, trifluoromethyl, trifluoromethylsulfonyl, 1-alkynyl, —COR, —CO$_2$R, —C(O)SR, —CHR'R", —NHR, —NHC(O)R, cyanamido, tricyanomethyl, —N(CN)$_2$, —C(CN)$_2$—R, —C(=C(CN)$_2$)—R, optionally substituted phenyl or optionally substituted heteroaryl;

R' represents nitro, nitroso, acyl or cyano;

R" represents hydrogen, acyl, alkyl, cycloalkyl, alkenyl, aryl, substituted aryl, cyano, nitro or nitroso; and R represents hydrogen, alkyl, alkenyl, alkynyl, cycloalkyl, arylalkyl, arylalkenyl, arylalkynyl, heteroaryl, heteroarylalkyl, or heteroarylalkenyl, any of which groups may be optionally substituted.

The nitrone analogs also bind the glycine receptor and are useful for treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease and Down's syndrome, treating or preventing the adverse consequences of the overstimulation of the excitatory amino acids, as well as treating anxiety, convulsions, chronic pain, psychosis and inducing anesthesia.

The compounds and methods described herein are an improvement over the prior art. The compounds of the current invention possess greater water solubility than the prior art compounds while maintaining high selectivity for the glycine receptor. It is also believed that the compounds of the invention bind to plasma proteins to a lesser degree than the compounds known in the prior art.

In one embodiment, the present invention relates to a method of treating or preventing (A) neuronal loss associated with stroke, ischemia, CNS trauma, or hypoglycemia or (B) the adverse neurological consequences of surgery, comprising administering to an animal in need of such treatment or prevention an effective amount of a compound defined by one of Formulae I–IV or a pharmaceutically acceptable salt thereof.

In a second embodiment, the present invention relates to a method of treating a neurodegenerative disease selected from Alzheimer's disease, amyotrophic lateral sclerosis, Huntington's disease, and Down's syndrome, comprising administering to an animal in need of such treatment an effective amount of a compound defined by one of Formulae I–IV or a pharmaceutically acceptable salt thereof.

In a third embodiment, the present invention relates to a method of antagonizing excitatory amino acids at the NMDA receptor complex, comprising administering to an animal in need thereof an effective amount of a compound defined by one of Formulae I–IV or a pharmaceutically acceptable salt thereof.

In a fourth embodiment, the present invention relates to a method of treating or preventing the adverse consequences of the hyperactivity of the NMDA receptor, comprising administering to an animal in need of such treatment or prevention an effective amount of a compound defined by one of Formulae I–IV or a pharmaceutically acceptable salt thereof.

In a fifth embodiment, the present invention relates to a method of treating chronic pain, comprising administering to an animal in need of such treatment an effective amount of a compound defined by one of Formulae I–IV or a pharmaceutically acceptable salt thereof.

In a sixth embodiment, the present invention relates to a method of treating or preventing anxiety, comprising administering to an animal in need of such treatment or prevention an effective amount of a compound defined by one of Formulae I–IV or a pharmaceutically acceptable salt thereof.

In a seventh embodiment, the present invention relates to a method of treating or preventing convulsions, comprising administering to an animal in need of such treatment or prevention an effective amount of a compound defined by one of Formulae I–IV or a pharmaceutically acceptable salt thereof.

In an eighth embodiment, the present invention relates to a method of inducing anesthesia, comprising administering to an animal in need of such anesthesia an effective amount of a compound defined by one of Formulae I–IV or a pharmaceutically acceptable salt thereof.

In a ninth embodiment, the present invention relates to a method of treating or preventing NMDA receptor-ion channel related psychosis, comprising administering to an animal in need of such treatment or prevention an effective amount of a compound defined by one of Formulae I–IV or a pharmaceutically acceptable salt thereof.

In a tenth embodiment, the present invention relates to a method of inducing a hypnotic effect, comprising administering to an animal in need of such treatment an effective amount of a compound defined by one of Formulae I–IV or a pharmaceutically acceptable salt thereof.

In an eleventh embodiment, the present invention relates to a radiolabelled compound having one of Formulae I–IV or a pharmaceutically acceptable salt thereof.

In a twelfth embodiment, the present invention relates to a method of preventing opiate tolerance, comprising administering to an animal in need of such prevention an effective amount of a compound having one of Formulae I–IV or a pharmaceutically acceptable salt thereof.

In a thirteenth embodiment, the present invention relates to a pharmaceutical compositions comprising a compound having one of Formulae I–IV and a pharmaceutically acceptable carrier.

DESCRIPTION OF THE PREFERRED EMBODIMENTS

The compounds which may be used in the practice of one embodiment of the invention have the Formulae (I–III) as shown and described above.

By choosing suitable starting materials, the 5-aza, 5-aza (N-oxy), 6-aza, 6-aza(N-oxy), 7-aza, 7-aza(N-oxy), 8-aza, 8-aza(N-oxy), 6,8-diaza, 6,8-diaza(mono-N-oxy), 6,8-diaza (di-N-oxy), 5,7-diaza, 5,7-diaza(mono-N-oxy) or 5,7-diaza (di-N-oxy) analogs of the above formulae can be prepared. Thus, compounds having the following structures are encompassed by the present invention:

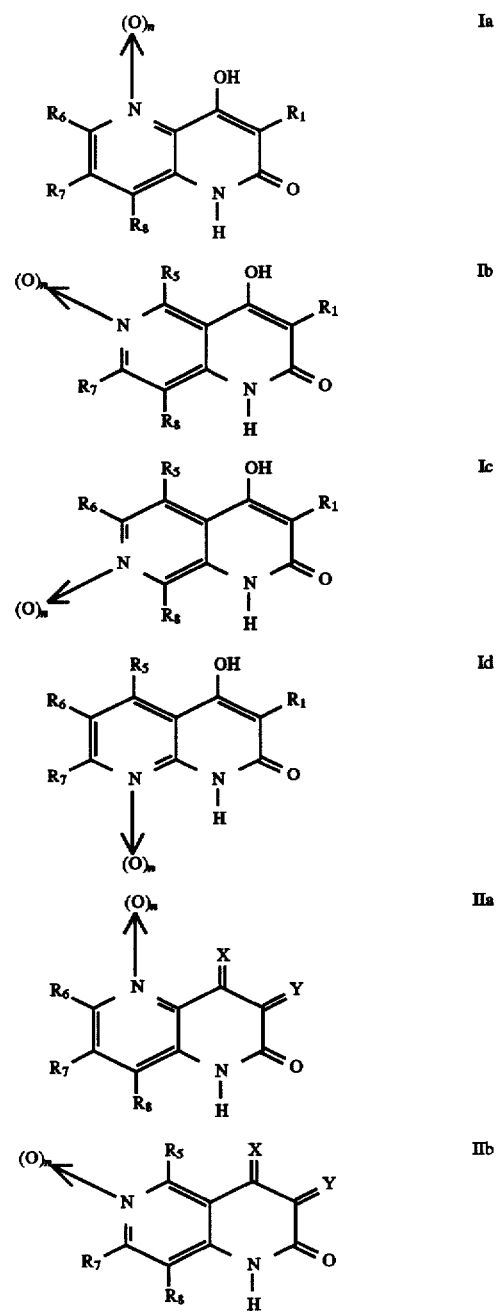

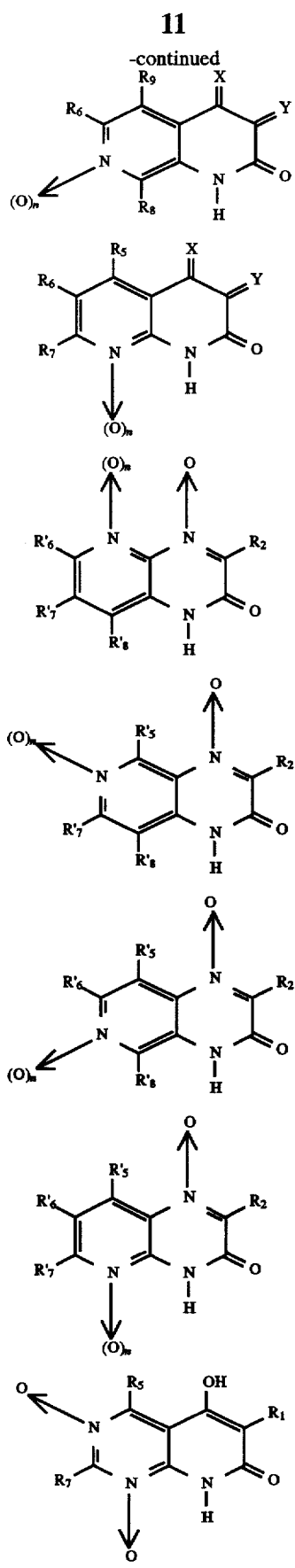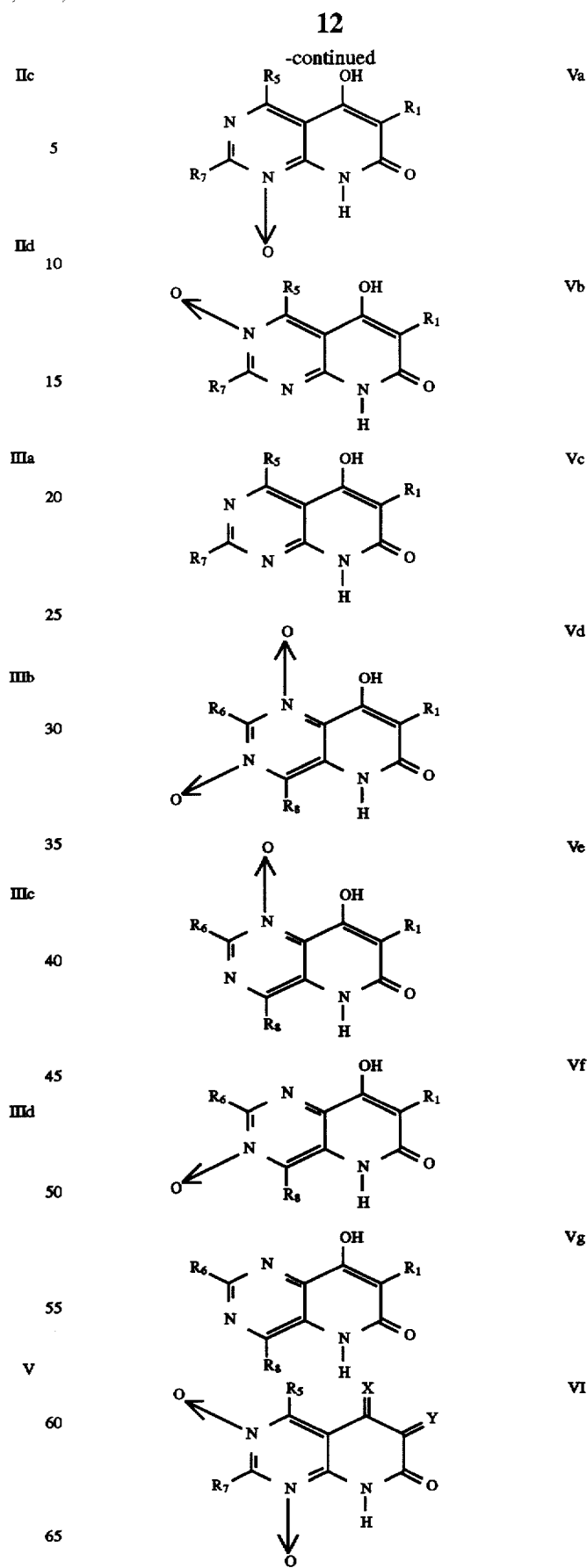

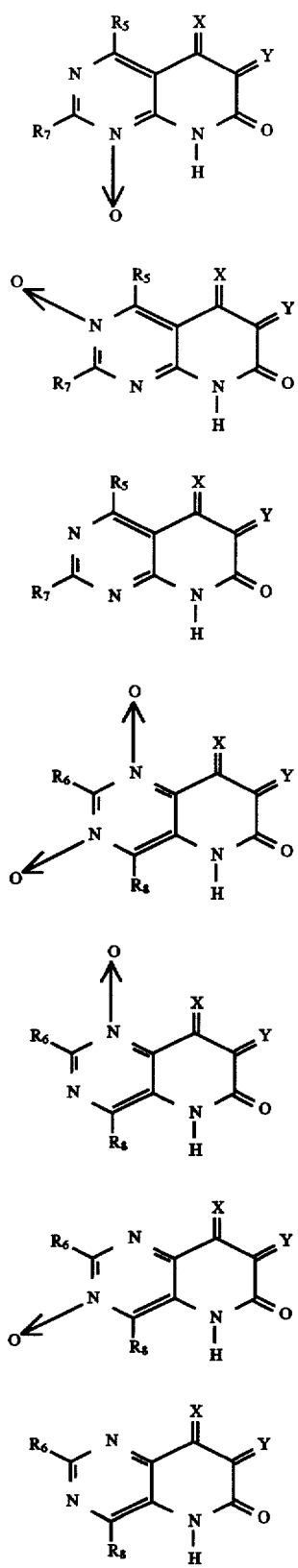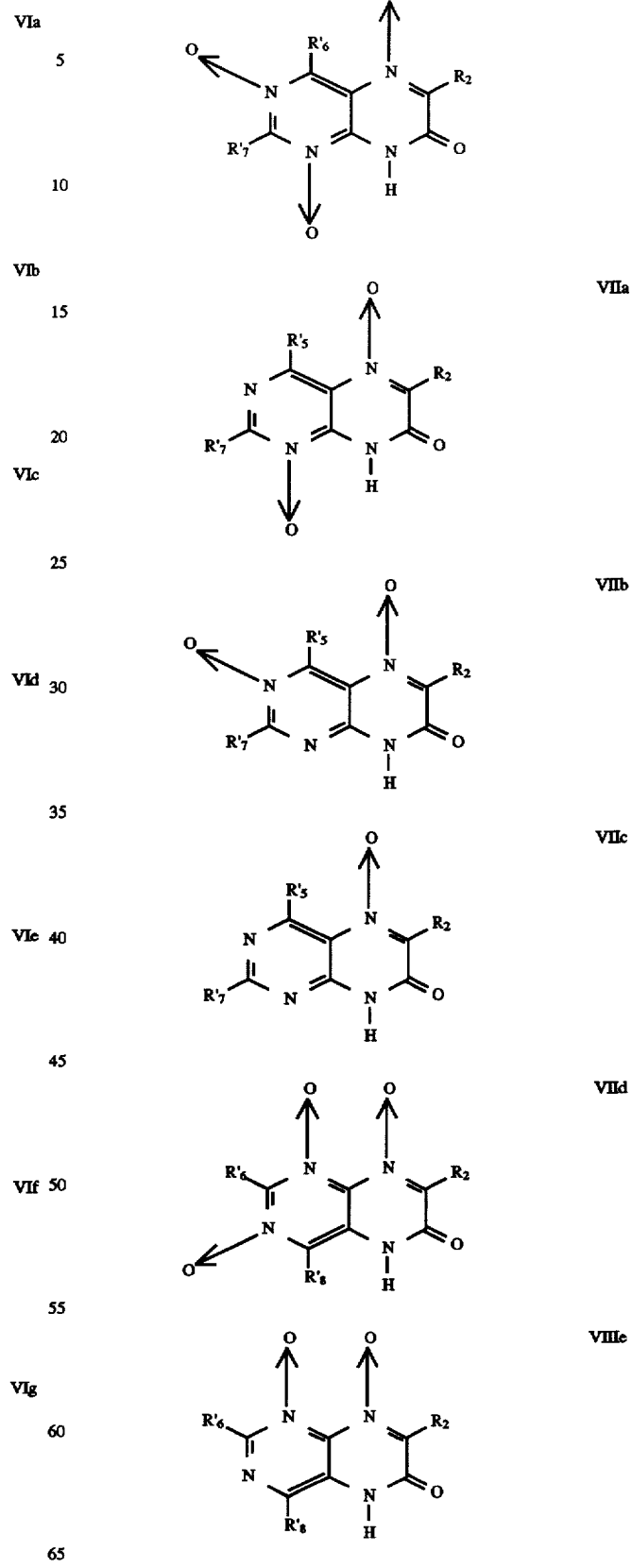

VIIf

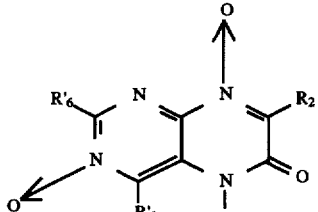

VIIg

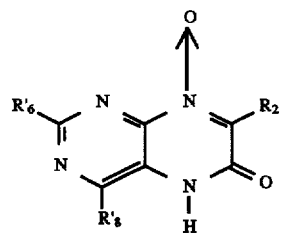

or tautomers or pharmaceutically acceptable salts thereof;

wherein $R_5$, $R_6$, $R_7$, $R'_5$, $R'_6$ and $R'_7$ independently represent hydrogen, nitro, amino, halo, haloalkyl, cyano, hydroxy, carboxy, alkyl, cycloalkyl, alkenyl, alkynyl, azido, acylamino, alkylthio, alkylsulfonyl, aryl, substituted aryl, heteroaryl, alkoxy, trialkylsilyl-substituted alkoxy, aryloxy, substituted aryloxy, heteroaryloxy, a heterocyclic group, a heterocyclicoxy group, aralkoxy or haloalkoxy;

$R_8$ and $R'_8$ represents one of hydrogen or fluorine;

n is zero or one;

$R_1$ represents nitro, cyano, trifluoromethyl, trifluoromethylsulfonyl, 1-alkynyl, —COR, —CO$_2$R, —C(O)SR, cyanamido, tricyanomethyl, —N(CN)$_2$, —C(CN)$_2$—R, —C(=C(CN)$_2$)—R, optionally substituted phenyl or optionally substituted heteroaryl;

$R_2$ represents nitro, cyano, trifluoromethyl, trifluoromethylsulfonyl, 1-alkynyl, —COR, —CO$_2$R, —C(O)SR, —CHR'R", —NHR, —NHC(O)R, cyanamido, tricyanomethyl, —N(CN)$_2$, —C(CN)$_2$—R, —C(=C(CN)$_2$)—R, optionally substituted phenyl, or optionally substituted heteroaryl;

R' represents nitro, nitroso, acyl or cyano;

R" represents hydrogen, acyl, alkyl, cycloalkyl, alkenyl, aryl, substituted aryl, cyano, nitro or nitroso;

R represents hydrogen, alkyl, alkenyl, alkynyl, cycloalkyl, arylalkyl, arylalkenyl, arylalkynyl, heteroaryl, heteroarylalkyl or heteroarylalkenyl, any of which groups may be optionally substituted; and one of X or Y is oxygen and the other of X or Y is N—OR$_9$, wherein R$_9$ represents hydrogen, alkyl, aryl, heteroaryl, acyl, halogen-substituted acyl or aryloyl.

Another aspect of the present invention relates to nitrone analogs of quinoxalone NMDA glycine receptor antagonists having the formula:

IV

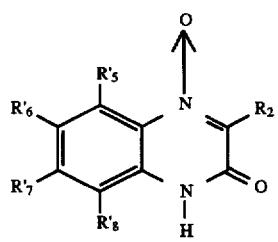

or tautomers or pharmaceutically acceptable salts thereof;

wherein $R'_5$, $R'_6$ and $R'_7$ independently represent hydrogen, nitro, amino, halo, haloalkyl, cyano, alkyl, cycloalkyl, alkenyl, alkynyl, azido, hydroxy, carboxy, acylamino, alkylsulfonyl, alkylthio, aryl, substituted aryl, heteroaryl, alkoxy, trialkylsilyl-substituted alkoxy, aryloxy, substituted aryloxy, heteroaryloxy, a heterocyclic group, a heterocyclicoxy group, aralkoxy or haloalkoxy;

$R'_8$ represents one of hydrogen or fluorine;

$R_2$ represents nitro, cyano, trifluoromethyl, trifluoromethylsulfonyl, 1-alkynyl, —COR, —CO$_2$R, —C(O)SR, —CHR'R", —NHR, —NHC(O)R, cyanamido, tricyanomethyl, —N(CN)$_2$, —C(CN)$_2$—R, —C(=C(CN)$_2$)—R, optionally substituted phenyl or optionally substituted heteroaryl;

R' represents nitro, nitroso, acyl or cyano;

R" represents hydrogen, acyl, alkyl, cycloalkyl, alkenyl, aryl, substituted aryl, cyano, nitro or nitroso; and R represents hydrogen, alkyl, alkenyl, alkynyl, cycloalkyl, arylalkyl, arylalkenyl, arylalkynyl, heteroaryl, heteroarylalkyl, or heteroarylalkenyl, any of which groups may be optionally substituted.

The nitrone analogs also bind the glycine receptor. The orally active glycine receptor antagonists reported by Kulagowski et al., J. Med. Chem. 37:1402–1405 (1994) have a pK$_a$ of about 5.5. Therefore, the majority of these molecules would be deprotonated at the 4-hydroxy group at physiological pH. The nitrone analogs have a similar structure to the deprotonated form of the orally active glycine receptor antagonists reported by Kulagowski et al. and are expected to have similar oral activity.

The compounds of the invention will in general exist in equilibrium with their other tautomeric forms. For example, tautomers of formula Ia include those structures of formulae A to C:

(A)

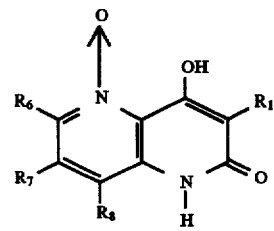

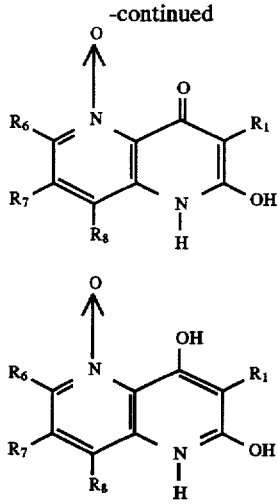

wherein $R_1$ and $R_5$ to $R_8$ are as defined above. It is to be understood that all tautomeric forms of the compounds of formulae I–VII, as well as all possible mixtures thereof, are included within the scope of the present invention.

Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof are encompassed within the scope of the present invention.

One sub-class of compounds which can be employed in the current invention is represented by the compounds of formulae Ie–Ih:

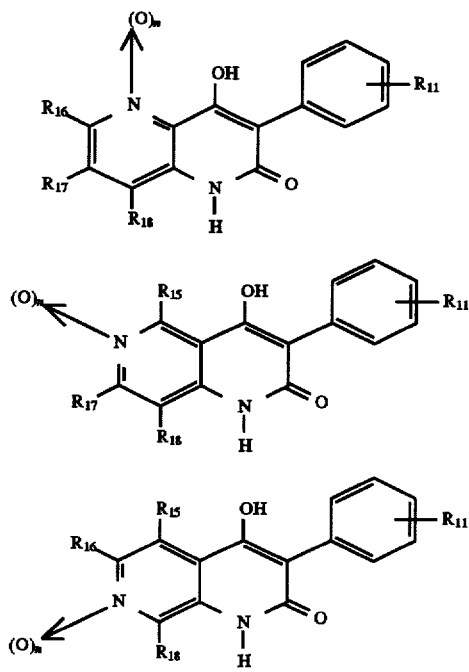

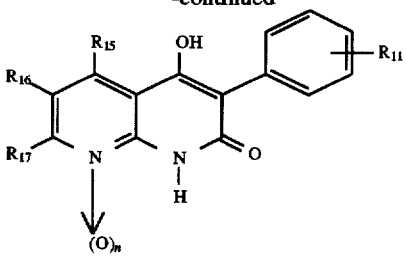

or tautomers or pharmaceutically acceptable salts thereof; wherein $R_{15}$, $R_{16}$ and $R_{17}$ independently represent hydrogen, nitro, amino, halo, haloalkyl, cyano, carboxy, alkyl, alkenyl, alkynyl, alkylthio, azido, acylamino, sulfonyl, aryl, alkoxycarbonyl or alkoxy;

$R_{18}$ represents hydrogen or fluorine;

$R_{11}$ represents hydrogen, halogen, cyano, trifluoromethyl, nitro, hydroxy, amino, carboxy, alkyl, alkenyl, alkoxy, alkynyl, aryl, arylalkyl, aryloxy, arylthio, arylalkenyl, arylalkynyl, heterocycloalkyl, heteroaryl, heteroarylalkyl, heteroaryloxy, heteroarylthio, and heteroarylalkenyl, any of which groups may be optionally substituted; and n is zero or one.

Suitable values of $R_{15}$, $R_{16}$ and $R_{17}$ include hydrogen, halogen, cyano, trifluoromethyl, nitro, hydroxy, amino, carboxy, $C_{1-6}$ alkyl, $C_{1-6}$ alkoxy, $C_{1-6}$ alkylthio or $C_{2-6}$ alkoxycarbonyl.

Suitable values of $R_{11}$ include hydrogen, halogen, cyano, trifluoromethyl, nitro, hydroxy, amino or carboxy. Additional suitable values of $R_{11}$ include $C_{1-6}$ alkyl, aryl($C_{1-6}$)alkyl, aryl($C_{1-6}$)alkenyl, aryloxy, heteroaryl($C_{1-6}$)alkyl, heteroaryl($C_{1-6}$)alkenyl or heteroaryloxy, any of which groups may be optionally substituted.

The optional substituents on the group $R_{11}$ suitably include hydroxy, halogen, trifluoromethyl, $C_{1-6}$ alkyl, $C_{1-6}$ alkoxy, $C_{1-6}$alkoxy($C_{1-6}$)alkoxy, $C_{1-6}$ haloalkyl, phenyl, benzyl or phenoxy.

The optional substituents on the group $R_{11}$ are preferably hydroxy, $C_{1-6}$ alkoxy or $C_{1-6}$alkoxy($C_{1-6}$)alkoxy.

Particular values of $R_{11}$ with respect to formula Ie, If, Ig and Ih include hydrogen, benzyl, phenethyl, hydroxyphenylmethyl, hydroxyphenethyl, phenoxy, methoxyphenylmethyl, methoxymethoxyphenylmethyl, thienylmethyl, thienylethyl, thienylvinyl, thienyloxy, pyridylethyl, pyridylmethyl, pyridyloxy, (N-oxy)pyridylmethyl and (N-oxy)pyridyloxy.

Preferably, for Ie, $R_{16}$ and $R_{18}$ are each hydrogen, and $R_{17}$ is one of fluoro, chloro, bromo, methyl, trifluoromethyl or nitro. For If, $R_{15}$ and $R_{18}$ are each hydrogen, and $R_{17}$ is one of fluoro, chloro, bromo, methyl, trifluoromethyl or nitro. For Ig, $R_{15}$, $R_{16}$ and $R_{18}$ are each hydrogen, and n is 1. For Ih, $R_{15}$ and $R_{16}$ are each hydrogen, $R_{17}$ is one of fluoro, chloro, bromo, methyl, trifluoromethyl or nitro, and n is 0.

When $R_{11}$ is benzyl, phenethyl, (4-hydroxyphenyl)methyl, (4-methoxyphenyl)methyl, (4-methoxymethoxyphenyl)methyl, phenoxy, (3-thienyl)methyl or (3-thienyl)oxy, $R_{11}$ is preferably in the meta position. When $R_{11}$ is $C_{1-6}$ alkyl, $C_{1-6}$ alkoxy, nitro, hydroxy or amino, $R_{11}$ is preferably in the para position.

Another sub-class of compounds according to the invention is represented by the compounds of formulae Ii, Ij, Ik or Il:

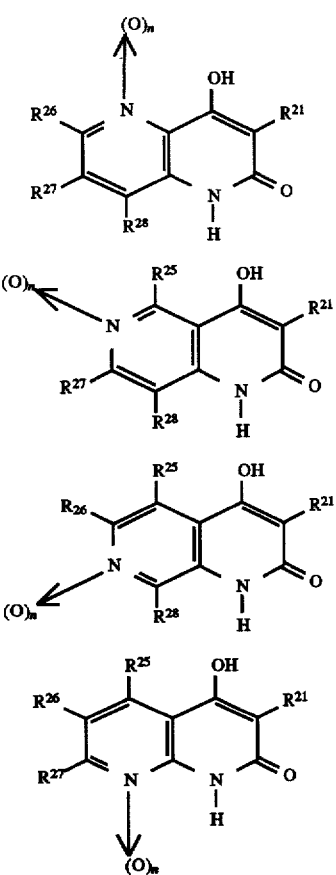

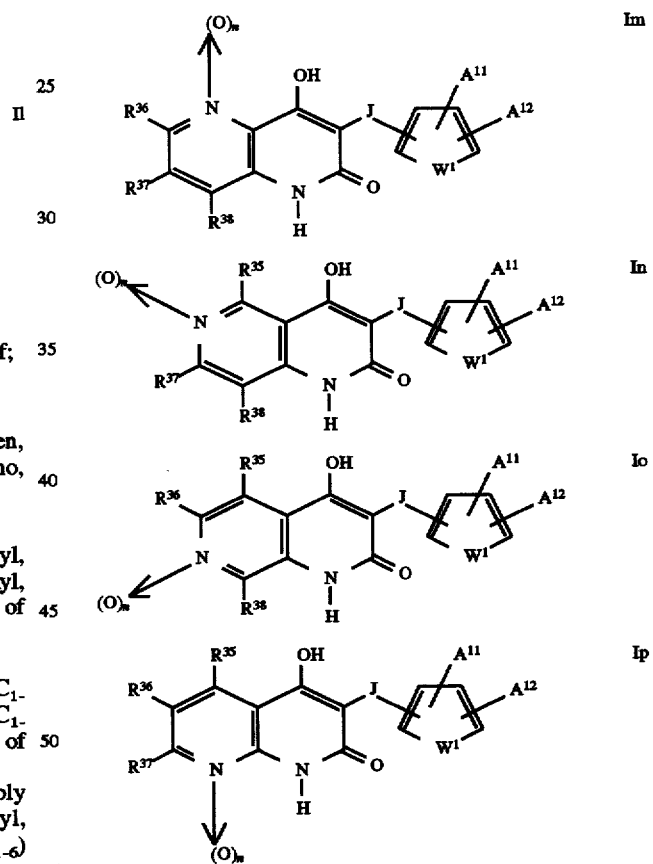

or tautomers or pharmaceutically acceptable salts thereof; wherein $R^{21}$ represents —$COR^{23}$ or —$CO_2R^{23}$;

$R^{25}$, $R^{26}$ and $R^{27}$ independently represent hydrogen, halogen, cyano, trifluoromethyl, nitro, hydroxy, amino, carboxy, $C_{1-6}$ alkyl, $C_{1-6}$ alkoxy, or $C_{1-6}$ alkylthio;

$R^{28}$ represents hydrogen or fluorine;

$R^{23}$ represents alkyl, alkenyl, alkynyl, cycloalkyl, aryl, arylalkyl, arylalkenyl, arylalkynyl, heterocycloalkyl, heteroaryl, heteroarylalkyl or heteroarylalkenyl, any of which groups may be optionally substituted; and n is zero or one.

Preferred values of $R^{23}$ include $C_{3-7}$ cycloalkyl, aryl($C_{1-6}$)alkyl, aryl($C_{2-6}$)alkenyl, aryl($C_{2-6}$)alkynyl, heteroaryl($C_{1-6}$)alkyl or heteroaryl($C_{2-6}$)alkenyl, heteroarylalkynyl, any of which groups may be optionally substituted.

The optional substituents on the group $R^{23}$ suitably include $C_{1-6}$ alkyl, phenyl, halogen, $C_{1-6}$ haloalkyl, trifluoromethyl, hydroxy, $C_{1-6}$ alkoxy, $C_{1-6}$ alkoxy($C_{1-6}$)alkoxy, aryloxy, keto, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, $C_{1-6}$ alkylthio, $C_{1-6}$ alkylsulfinyl, $C_{1-6}$ alkylsulfonyl, amino $C_{2-6}$ alkoxycarbonylamino and $C_{2-6}$ alkoxycarbonylamino($C_{1-6}$)alkyl.

The optional substituents on the group $R^{23}$ are preferably hydroxy, $C_{1-6}$ alkoxy, $C_{1-6}$ alkoxy($C_{1-6}$)alkoxy and $C_{2-6}$ alkoxycarbonylamino($C_{1-6}$)alkyl, especially hydroxy, methoxy, methoxymethoxy and t-butoxycarbonylaminomethyl.

Particular values of $R^{23}$ with respect to formulae Ii, Ij, Ik and Il include cyclopropyl, benzyl, phenethyl, hydroxyphenethyl, bis(methoxymethoxy)phenethyl, (t-butoxycarbonylaminomethyl)phenethyl, phenylpropyl, hydroxyphenylpropyl, phenylbutyl, hydroxyphenylbutyl, phenylallyl, methoxyphenylallyl, phenylpropargyl, hydroxyphenylpropargyl, methoxyphenylpropargyl, indolylethyl, methoxyindolylethyl, indolylpropyl, thienylethyl, thienylvinyl, pyridylethyl, pyridylpropargyl, (N-oxy)pyridylethyl and (N-oxy)pyridylpropargyl. Preferred values of $R^{23}$ are cyclopropyl and hydroxyphenylpropargyl.

Suitably, $R^{25}$, $R^{26}$ and $R^{27}$ are independently selected from hydrogen, halogen, trifluoromethyl, nitro, amino and $C_{1-6}$ alkyl, provided that at least one of $R^{25}$, $R^{26}$ and $R^{27}$ is other than hydrogen. Preferably $R^{26}$ represents hydrogen or halogen, one of $R^{25}$ and $R^{27}$ represents halogen or nitro, and the other of $R^{25}$ and $R^{27}$ represents hydrogen, halogen or nitro. In a particular embodiment, $R^{25}$ and $R^{26}$ each represents hydrogen and $R^{27}$ represents halogen, especially chlorine.

An additional sub-class of compounds according to the invention is represented by the compounds of formulae Im, In, Io and Ip:

or tautomers or pharmaceutically acceptable salts thereof; wherein $W^1$ represents oxygen, sulphur or N—$A^{13}$, $A^{11}$ and $A^{12}$ independently represent hydrogen, halogen, cyano, trifluoromethyl, nitro, hydroxy, amino, carboxy, $C_{1-6}$ alkyl, $C_{2-6}$ alkenyl, $C_{2-6}$ alkynyl, $C_{3-7}$cycloalkyl, $C_{3-7}$ cycloalkyl($C_{1-6}$)alkyl, aryl, aryl($C_{1-6}$)alkyl, $C_{1-6}$ alkoxy, $C_{2-6}$ alkenyloxy, $C_{1-6}$ alkylthio, $C_{2-6}$ alkenylthio, $C_{2-6}$ alkylcarbonyl, arylcarbonyl or $C_{2-6}$ alkoxycarbonyl; or $A^{11}$ and $A^{12}$ together represent the residue of an optionally substituted aromatic or heteroaromatic ring;

$A^{13}$ represents hydrogen, $C_{1-6}$ alkyl or aryl($C_{1-6}$)alkyl;

J represents a bond or a carbonyl group (C=O);

$R^{38}$ represents hydrogen or fluorine; and $R^{35}$, $R^{36}$ and $R^{37}$ independently represent hydrogen, halogen, cyano, trifluoromethyl, nitro, hydroxy, amino, carboxy, $C_{1-6}$ alkyl, $C_{1-6}$ alkoxy, $C_{1-6}$ alkylthio or $C_{2-6}$ alkoxycarbonyl; and n is zero or one.

Examples of suitable values for the groups $A^{11}$ and $A^{12}$ include hydrogen, halogen, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, $C_{1-6}$ alkoxy, $C_{2-6}$ alkenyloxy, $C_{1-6}$ alkylthio, $C_{2-6}$ alkenylthio and arylcarbonyl. Particular values of $A^{11}$ and $A^{12}$ include hydrogen, bromo, methyl, ethyl, isopropyl, vinyl, allyl, cyclopropyl, cyclopropylmethyl phenyl, benzyl, allyloxy, allylthio and benzoyl.

Where $A^{11}$ and $A^{12}$ together represent the residue of an optionally substituted aromatic or heteroaromatic ring, this is preferably an optionally substituted benzene ring. Examples of optional substituents on the aromatic or heteroaromatic ring suitably include nitro, and $C_{1-6}$ alkoxy such as methoxy.

Suitably, $A^{13}$ represents hydrogen or methyl, preferably methyl.

Suitably, $R^{35}$, $R^{36}$ and $R^{37}$ are independently selected from hydrogen, halogen, nitro, amino and $C_{1-6}$ alkyl, provided that at least one of $R^{35}$, $R^{36}$ and $R^{37}$ is other than hydrogen. Preferably $R^{36}$ represents hydrogen or halogen, one of $R^{35}$ and $R^{37}$ represents halogen or nitro, and the other of $R^{35}$ and $R^{37}$ represents hydrogen, halogen or nitro. In a particular embodiment, $R^{35}$ and $R^{36}$ each represents hydrogen and $R^{37}$ represents halogen, especially chlorine.

A further sub-class of compounds according to the invention is represented by the compounds of formulae Iq, Ir, Is and It and salts thereof:

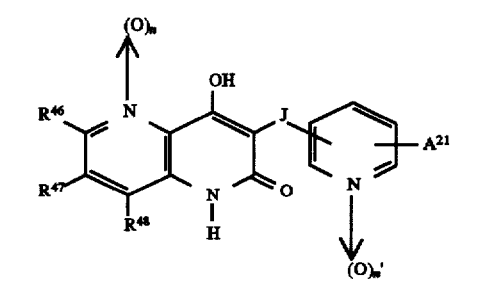

Iq

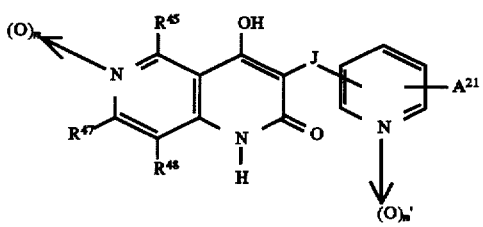

Ir

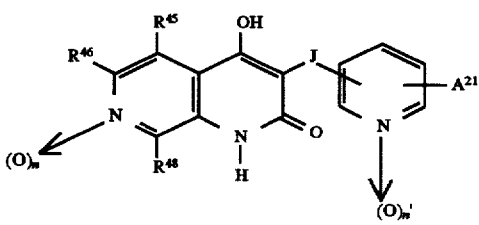

Is

-continued

It wherein $A^{21}$ represents hydrogen, halogen, cyano, trifluoromethyl, nitro, hydroxy, amino, carboxy, $C_{1-6}$ alkyl, $C_{1-6}$ alkoxy, $C_{1-6}$ alkylthio, $C_{2-6}$ alkylcarbonyl, arylalkyl, aryloxy, arylalkenyl, arylalkynyl, heteroaryl, heteroarylalkyl, heteroaryloxy, heteroarylalkenyl, arylcarbonyl, or $C_{2-6}$ alkoxycarbonyl;

J represents a bond or a carbonyl group (C=O);

$R^{48}$ represents hydrogen or fluorine;

$R^{45}$, $R^{46}$ and $R^{47}$ independently represent hydrogen, halogen, cyano, trifluoromethyl, nitro, hydroxy, amino, carboxy, $C_{1-6}$ alkyl, $C_{1-6}$ alkoxy, $C_{1-6}$ alkylthio or $C_{2-6}$ alkoxycarbonyl, provided that at least one of $R^{45}$, $R^{46}$ and $R^{47}$ is other than hydrogen; and n and n' are each independently zero or one.

Examples of suitable values for the groups $A^{21}$ include hydrogen, halogen, $C_{1-6}$ alkyl, aryl($C_{1-6}$)alkenyl, heteroaryl ($C_{1-6}$)alkyl, heteroaryl($C_{1-6}$)alkenyl and arylcarbonyl. Preferably, $A^{21}$ is hydrogen. Additionally, the aryl and heteroaryl moieties present in $A^{21}$ may have one, two or three optional substituents. These optional substituents suitably include hydroxy, halogen, trifluoromethyl, $C_{1-6}$ alkyl, $C_{1-6}$ alkoxy, $C_{1-6}$alkoxy($C_{1-6}$)alkoxy, $C_{1-6}$ haloalkyl, phenyl, benzyl or phenoxy.

Suitably, $R^{45}$, $R^{46}$ and $R^{47}$ are independently selected from hydrogen, halogen, nitro, amino and $C_{1-6}$ alkyl, provided that at least one of $R^{45}$, $R^{46}$ and $R^{47}$ is other than hydrogen. Preferably $R^{46}$ represents hydrogen or halogen, one of $R^{45}$ and $R^{47}$ represents halogen or nitro, and the other of $R^{45}$ and $R^{47}$ represents hydrogen, halogen or nitro.

Preferably, J is a bond and can attach the quinolone to the 2, 3 or 4 positions of the pyridine moiety.

Most preferably, for Iq, $A^{21}$, $R^{46}$ and $R^{48}$ are each hydrogen, J is a bond, and $R^{47}$ is one of fluoro, chloro, bromo, methyl, trifluoromethyl or nitro. Most preferably, for Ir, $A^{21}$, $R^{45}$ and $R^{48}$ are each hydrogen, J is a bond, and $R^{47}$ is one of fluoro, chloro, bromo, methyl, trifluoromethyl or nitro. Most preferably, for Is, $A^{21}$, $R^{45}$, $R^{46}$ and $R^{48}$ are each hydrogen, J is a bond, and n is 1. Most preferably, for It, $A^{21}$, $R^{45}$ and $R^{46}$ are each hydrogen, J is a bond, $R^{47}$ is one of fluoro, chloro, bromo, methyl, trifluoromethyl or nitro, n' is zero or one n is zero.

Compounds wherein an aza and/or an aza(N-oxy) group is at each of positions 6 and 8 or positions 5 and 7 are considered equivalents of the compounds having formulae Ie through It for the purposes of this invention.

Preferred compounds within the scope of Formulae III and IV are nitrones capable of existing in a tautomeric N-hydroxy form. Nitrone-N-hydroxyenamine tautomerism is known for several classes of heterocyclic compounds (Breuer E. In *Nitrones, Nitronates and Nitroxides*; Patai and Rappoport, Eds.; John Wiley & Sons: N.Y.; 1989, p. 139). Examples of nitrone derivatives in the quinoxaline series which are expected to exist in N-hydroxy forms include, but are not limited to, two following subclasses of compounds.

One subclass of compounds that can be employed in this aspect of the current invention is represented by compounds of the following formulae:

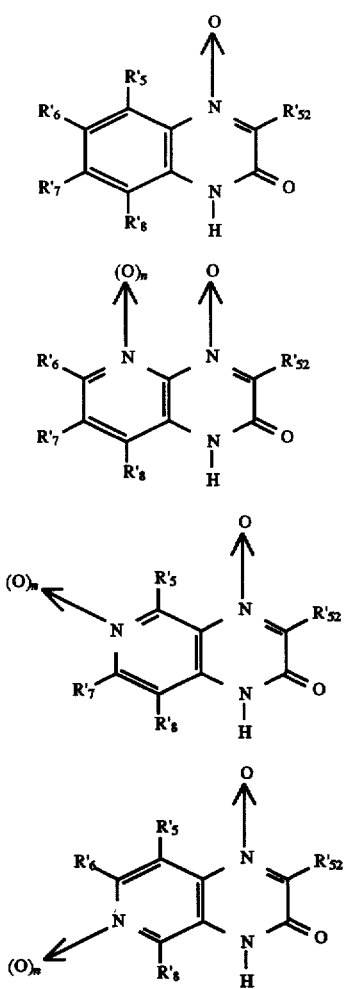

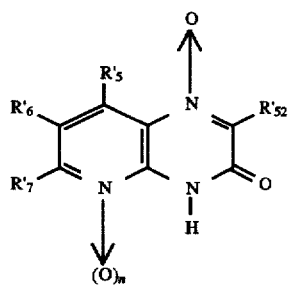

or tautomers or pharmaceutically acceptable salts thereof;

wherein $R'_5$, $R'_6$, $R'_7$ and $R'_8$ are as defined above for Formula IV;

$R'_{52}$ represents substituted aryl or substituted heteroaryl, wherein said substituted aryl or substituted heteroaryl are substituted with —OH, —SH or a group —NHR'$_a$ wherein R'$_a$ represents hydrogen, alkyl, cycloalkyl or alkoxy; and n is zero or one.

Preferably $R'_{52}$ is phenyl, substituted at the ortho- or para-position with —OH, —SH or —NHR'$_a$, where R'$_a$ is preferably hydrogen, $C_{1-6}$ alkyl or $C_{1-6}$ alkoxy.

The most preferred compounds of Formulae IIe–IIIh and IVb have a proton donor substituent (—OH, —SH or —NHR'$_a$) in an active position of the aromatic or heteroaromatic ring. Thus, compounds having the following structures and tautomeric forms are included within the preferred scope of the invention:

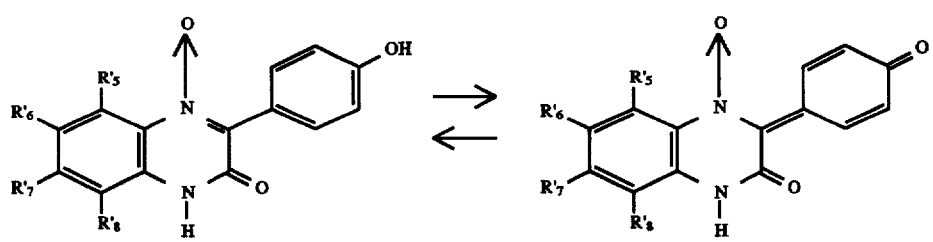

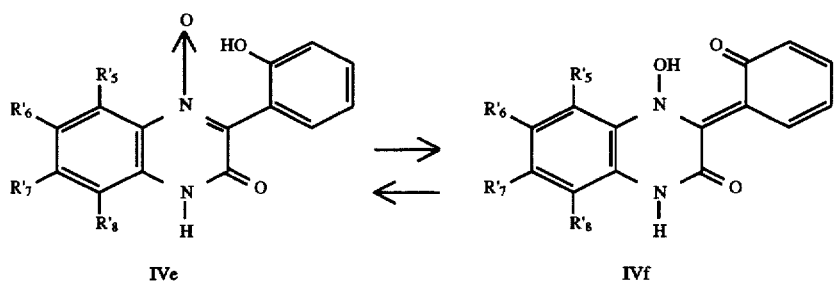

wherein, preferably, $R'_5$ represents hydrogen, nitro or halogen; $R'_6$ and $R'_7$ independently represent hydrogen or halogen; and $R'_8$ is hydrogen.

Another subclass of compounds that can be employed in the current invention is represented by compounds of the following formulae:

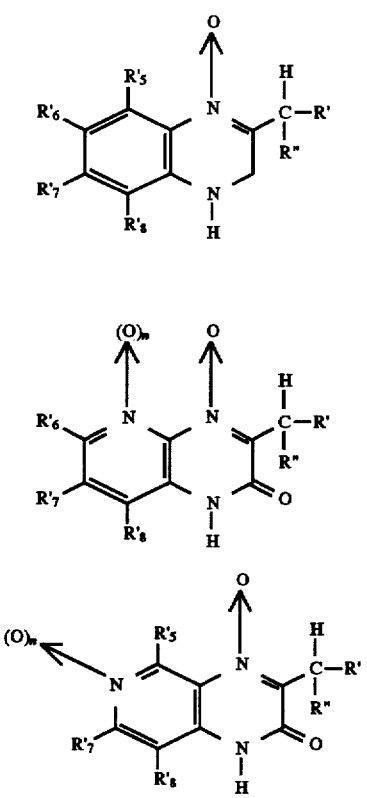

or tautomers or pharmaceutically acceptable salts thereof;

wherein $R'_5$, $R'_6$, $R'_7$, $R'_8$, $R'$ and $R''$ are as defined above for Formula IV; and n is zero or one.

The compounds of this subclass will also exist in equilibrium with their other tautometric forms, including:

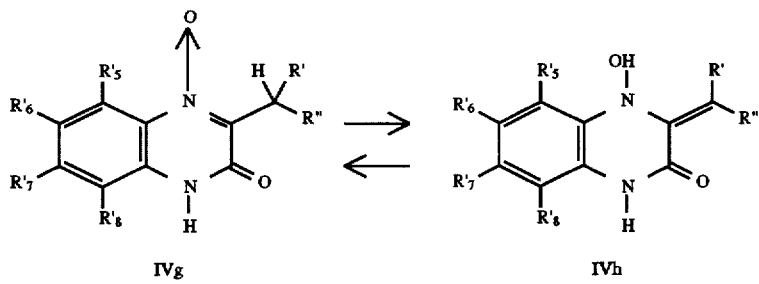

Preferably, R' represents hydrogen; R" represents acyl, cyano, nitro, nitroso or amino; R'$_5$ represents hydrogen, nitro or halogen; R'$_6$ and R'$_7$ independently represent hydrogen or halogen; and R'$_8$ represents hydrogen. Most preferably, R'$_5$ and R'$_6$ are hydrogen while R'$_7$ is chlorine; or R'$_5$ and R'$_7$ are chlorine, and R'$_6$ is hydrogen.

Preferred aryl groups are those having 6 to 14 carbon atoms. Typical C$_{6-14}$ aryl groups include phenyl, naphthyl, phenanthryl, anthracyl, indenyl, azulenyl, biphenyl, biphenylenyl, and fluorenyl groups.

Typical aryloxy groups include any of the C$_{6-14}$ aryl groups linked by oxygen, e.g., phenoxy and 1-naphthyloxy groups.

Typical substituted aryl groups include any of the C$_{6-14}$ aryl groups substituted by one or more halo, nitro, cyano, alkyl, alkenyl, and alkynyl groups, e.g., 2-chlorophenyl, 2,4-dibromophenyl, and the like.

Typical substituted aryloxy groups include any of the C$_{6-14}$ aryl groups substituted by one or more halo, nitro, cyano, alkyl, alkenyl, and alkynyl groups, and linked by oxygen, e.g., 2-chlorophenoxy, 2,4-dibromophenoxy, and the like.

Typical aryloyl groups include any of the above-mentioned aryl groups substituted by a carbonyl group.

Preferred heterocyclic groups are those having 3 to 10 carbon atoms and having one or more 4, 5, 6, or 7 member saturated or unsaturated rings containing 1, 2, or 3 oxygen, nitrogen or sulfur heteroatoms (where examples of hetero-cyclic radicals are: tetrahydrofuran, 1,4-dioxane, 1,3,5-trioxane, pyrrolidine, piperidine, piperazine, imadazoline, isoindoline, chromane, isochromane, pyrazolidine, quinuclidine, pyridine, pyrrole, oxazole, indole, purine, pyrimidine, 1,3-dithiane, azetidine, tetrahydropyran, imidazole, thiazole, isoxazole, pyrazole, quinoline, cytosine, thymine, uracil, adenine, guanine, pyrazine, 1-methyl-1,4-dihydronicotine, picolinic acid, picoline, furoic acid, furfural, furfuryl alcohol, carbazole, isoquinoline, 3-pyrroline, thiophene, furan, hexamethyleneimine, E-caprolactone, e-caprolactam, omega-thiocaprolactam, and morpholine).

Typical heteroaryl groups have 3 to 14 ring atoms; 6, 10 or 14 π electrons shared in a cyclic array; and contain carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

Typical heteroaryloxy groups include any of the heteroaryl groups linked by oxygen, e.g. 2-furanoxy, 4-pyridoxy, 2-pyrazinoxy, purine-6-oxy and the like.

Typical heterocyclicoxy groups include any of the heterocyclic groups linked by oxygen, e.g. 4-tetrahydropyranyloxy.

Typical amino groups include NH$_2$, NHR$_8$, and NR$_8$R$_9$, wherein R$_8$ and R$_9$ are C$_{1-4}$ alkyl groups.

Typical halo groups include fluorine, chlorine, bromine, and iodine.

Typical C$_{1-4}$ alkyl groups include methyl, ethyl, propyl, isopropyl, butyl, sec-butyl, and tert-butyl groups.

Typical C$_{3-8}$ cycloalkyl groups include cyclopropyl, cyclobutyl, cyclopentyl, cyclohexyl, cycloheptyl, and cyclooctyl groups.

Typical C$_{2-4}$ alkenyl groups include vinyl, allyl, 1-butenyl, 2-butenyl, 3-butenyl, and isobutenyl groups.

Typical C$_{2-4}$ alkynyl groups include propargyl, 1-propynyl, 2-propynyl, 1-butynyl, 2-butynyl, and 3-butynyl groups.

Typical aralkoxy groups include C$_{1-4}$ alkoxy groups substituted by any one of the aryl groups mentioned above.

Typical haloalkyl groups include C$_{1-4}$ alkyl groups substituted by one or more fluorine, chlorine, bromine, or iodine atoms, e.g., fluoromethyl, difluoromethyl, trifluoromethyl, pentafluoroethyl, 1,1-difluoroethyl, and trichloromethyl groups.

Typical alkoxy groups include any one of the C$_{1-4}$ alkyl groups mentioned above linked by oxygen.

Typical haloalkoxy groups include any one of the alkoxy groups substituted by one or more fluoro, chloro, bromo, or iodo groups, e.g., trifluoromethoxy, trichloromethoxy, 2-chloroethoxy, 2-bromoethoxy, pentafluoroethyl, 3,3,3-trichloropropoxy, 4,4,4-trichlorobutoxy, and the like.

Typical trialkylsilyl-substituted alkoxy groups include any one of the C$_{1-4}$ alkoxy groups substituted by a C$_{3-6}$ trialkylsilyl group, e.g. 2-trimethylsilylethoxy, 2-triethylsilylethoxy and 2-(t-butyldimethylsilyl)ethoxy, and the like.

Typical C$_{2-6}$ acyl (alkanoyl) groups include acetyl, propionyl, butanoyl, and pentanoyl groups.

Typical C$_{2-6}$ acyl groups substituted by halogen include the above-mentioned acyl groups substituted by one or more fluoro, chloro, bromo or iodo groups, e.g., trifluoroacetyl.

Examples of optional substituents on "substituted" or "optionally substituted" groups of R$_x$, R$_y$, R$_2$, R$_5$, R$_6$, R$_7$, R'$_5$, R'$_6$, R'$_7$, R, R$_1$, R$_2$, and R" suitably include hydrogen, halogen, cyano, trifluoromethyl, nitro, hydroxy, amino, carboxy, C$_{1-6}$ alkyl, C$_{2-6}$ alkenyl, C$_{2-6}$ alkynyl, C$_{3-7}$ cycloalkyl, $C_{3-7}$ cycloalkyl($C_{1-6}$)alkyl, aryl, aryloxy, arylthio, aryl($C_{1-6}$)alkyl, $C_{1-6}$ alkoxy, $C_{2-6}$ alkenyloxy, $C_{1-6}$ alkylthio, $C_{1-6}$ alkylsulfinyl, $C_{1-6}$ alkylsulfonyl, $C_{2-6}$ alkenylthio, $C_{2-6}$ alkylcarbonyl, arylcarbonyl or $C_{2-6}$ alkoxycarbonyl, $C_{1-6}$ alkoxy($C_{1-6}$)alkoxy, $C_{1-6}$ alkoxybenzyl, $C_{1-6}$ alkoxy($C_{1-6}$)alkoxybenzyl, phenoxy, heteroaryl($C_{1-6}$)alkyl, heteroarylthio or heteroaryloxy. Optional substituents have been described for other groups above.

Preferred compounds within the scope of Formula I include those of Formula Ia wherein $R_1$ is nitro, $R_6$ and $R_7$ independently represent hydrogen, fluoro, chloro, bromo, methyl, trifluoromethyl or nitro, and $R_8$ is hydrogen; compounds of Formula Ib wherein $R_1$ is nitro, $R_5$ and $R_7$ independently represent hydrogen, fluoro, chloro, bromo, methyl, trifluoromethyl or nitro, and $R_8$ is hydrogen; compounds of Formula Ic wherein $R_1$ is nitro, $R_5$ and $R_6$ independently represent hydrogen, fluoro, chloro, bromo, methyl, trifluoromethyl or nitro and $R_8$ is hydrogen; and compounds of Formula Id wherein $R_1$ is nitro, $R_5$, $R_6$ and $R_7$ independently represent hydrogen, fluoro, chloro, bromo, methyl, trifluoromethyl or nitro, and n is zero.

Additional preferred compounds within the scope of Formula I include those of Formula Ia wherein $R_1$ is cyano, $R_6$ and $R_7$ independently represent hydrogen, fluoro, chloro, bromo, methyl, trifluoromethyl or nitro, and $R_8$ is hydrogen; compounds of Formula Ib wherein $R_1$ is cyano, $R_5$ and $R_7$ independently represent hydrogen, fluoro, chloro, bromo, methyl, trifluoromethyl or nitro, and $R_8$ is hydrogen; compounds of Formula Ic wherein $R_1$ is cyano, $R_5$ and $R_6$ independently represent hydrogen, fluoro, chloro, bromo, methyl, trifluoromethyl or nitro and $R_8$ is hydrogen; and compounds of Formula Id wherein $R_1$ is cyano, $R_5$, $R_6$ and $R_7$ independently represent hydrogen, fluoro, chloro, bromo, methyl, trifluoromethyl or nitro, and n is zero. Additional preferred compounds within the scope of Formula I include compounds defined by Formulae Ie–It above.

Especially preferred compounds within the scope of Formula I include 5-aza-7-chloro-4-hydroxy-3-nitro-2-quinolone, 5-(N-oxy)aza-7-chloro-4-hydroxy-3-nitro-2-quinolone, 5-aza-7-chloro-3-cyano-4-hydroxy-2-quinolone, 5-(N-oxy)aza-7-chloro-3-cyano-4-hydroxy-2-quinolone, 5-aza-7-chloro-4-hydroxy-3-(3'-methoxyphenyl)-2-quinolone, 5-(N-oxy)aza-7-chloro-4-hydroxy-3-(3'-methoxyphenyl)-2-quinolone, 5-aza-7-chloro-4-hydroxy-3-(3'-phenoxyphenyl)-2-quinolone, 5-(N-oxy)aza-7-chloro-4-hydroxy-3-(3'-phenoxyphenyl)-2-quinolone, 5-aza-7-chloro-4-hydroxy-3-(4'-methoxyphenyl)-2-quinolone, 5-(N-oxy)aza-7-chloro-4-hydroxy-3-(4'-methoxyphenyl)-2-quinolone, 5-aza-7-chloro-4-hydroxy-3-(2-pyridyl)-2-quinolone, 5-(N-oxy)aza-7-chloro-4-hydroxy-3-(2-pyridyl)-2-quinolone, 5-aza-7-chloro-4-hydroxy-3-[2-(N-oxy)pyridyl]-2-quinolone, 5-(N-oxy)aza-7-chloro-4-hydroxy-3-[2-(N-oxy)pyridyl]-2-quinolone, 5-aza-7-chloro-4-hydroxy-3-(3-pyridyl)-2-quinolone, 5-(N-oxy)aza-7-chloro-4-hydroxy-3-(3-pyridyl)-2-quinolone, 5-aza-7-chloro-4-hydroxy-3-[3-(N-oxy)pyridyl]-2-quinolone, 5-(N-oxy)aza-7-chloro-4-hydroxy-3-[3-(N-oxy)pyridyl]-2-quinolone, 5-aza-7-chloro-4-hydroxy-3-(4-pyridyl)-2-quinolone, 5-(N-oxy)aza-7-chloro-4-hydroxy-3-(4-pyridyl)-2-quinolone, 5-aza-7-chloro-4-hydroxy-3-[4-(N-oxy)pyridyl]-2-quinolone, 5-(N-oxy)aza-7-chloro-4-hydroxy-3-[4-(N-oxy)pyridyl]-2-quinolone. 5-aza-7-chloro-4-hydroxy-3-[3'-(2-pyridyloxyphenyl)]-2-quinolone, 5-(N-oxy)aza-7-chloro-4-hydroxy-3-[3'-(2-pyridyloxyphenyl)]-2-quinolone, 5-aza-7-chloro-4-hydroxy-3-{3'-[2-(N-oxy)pyridyloxyphenyl]}-2-quinolone, 5-(N-oxy)aza-7-chloro-4-hydroxy-3-{3'-[2-(N-oxy)pyridyloxyphenyl]}-2-quinolone.

With respect to Formula IIa, preferred compounds are those wherein X is oxygen, Y is NOH, $R_6$ and $R_7$ independently represent hydrogen, fluoro, chloro, bromo, methyl, trifluoromethyl or nitro, and $R_8$ is hydrogen; compounds of Formula IIb wherein X is oxygen, Y is NOH, $R_5$ and $R_7$ independently represent hydrogen, fluoro, chloro, bromo, methyl, trifluoromethyl or nitro, and $R_8$ is hydrogen; compounds of Formula IIc wherein X is oxygen, Y is NOH, $R_5$ and $R_6$ independently represent hydrogen, fluoro, chloro, bromo, methyl, trifluoromethyl or nitro, and $R_8$ is hydrogen; and compounds of Formula IId wherein X is oxygen, Y is NOH, $R_5$, $R_6$ and $R_7$ independently represent hydrogen, fluoro, chloro, bromo, methyl, trifluoromethyl or nitro, and n is zero.

Especially preferred compounds having Formula II include 5-aza-7-chloroquinoline-2,3,4-trione-3-oxime, 5-(N-oxy)aza-7-chloroquinoline-2,3,4-trione-3-oxime, 5-aza-7-bromoquinoline-2,3,4-trione-3-oxime, 5-(N-oxy)aza-7-bromoquinoline-2,3,4-trione-3-oxime, 5-aza-7-methylquinoline-2,3,4-trione-3-oxime, 5-(N-oxy)aza-7-methylquinoline-2,3,4-trione-3-oxime, 5-aza-7-chloro-6-methylquinoline-2,3,4-trione-3-oxime, and 5-(N-oxy)aza-7-chloro-6-methylquinoline-2,3,4-trione-3-oxime.

With respect to Formula IIIa, preferred compound include those wherein $R'_6$ and $R'_7$ independently represent hydrogen, fluoro, chloro, bromo, methyl, trifluoromethyl, or nitro; $R'_8$ is hydrogen; $R_2$ represents phenyl or phenoxy, either or which is optionally substituted with hydroxy, $C_{1-6}$ alkoxy, $C_{1-6}$ alkoxy($C_{1-6}$)alkoxy or phenoxy; or —$CO_2R^{23}$, wherein values of $R^{23}$ preferably include $C_{3-7}$ cycloalkyl, aryl($C_{1-6}$) alkyl, aryl($C_{2-6}$)alkynyl or heteroaryl($C_{1-6}$)alkyl, any of which groups being optionally substituted with hydroxy or $C_{1-6}$ alkoxy. Alternatively, $R_2$ represents cyano, trifluoromethyl, trifluoromethylsulfonyl or 1-alkynyl.

With respect to Formula IIIb preferred compounds include those wherein $R'_5$ and $R'_7$ independently represent hydrogen, fluoro, chloro, bromo, methyl, trifluoromethyl, or nitro; $R'_8$ is hydrogen; $R_2$ represents the same groups as in the preceding paragraph. With respect to Formula IIIc preferred compounds include those wherein $R'_5$ and $R'_6$ independently represent hydrogen, fluoro, chloro, bromo, methyl, trifluoromethyl, or nitro; $R'_8$ is hydrogen; $R_2$ represents the same groups as in the preceding paragraph. With respect to Formula IIId preferred compounds include those wherein $R'_5$, $R'_6$ and $R'_7$ independently represent hydrogen, fluoro, chloro, bromo, methyl, trifluoromethyl, or nitro; $R'_8$ is hydrogen; $R_2$ represents the same groups as in the preceding paragraph.

With respect to Formula IV, preferred compounds are those wherein $R'_5$ is hydrogen, $R'_7$ is $C_{1-6}$ alkyl, most preferably methyl and $R_2$ is phenyl; phenyl substituted in the 2, 3 or 4 position with one of hydroxy, $C_{1-6}$ alkoxy, $C_{1-6}$ alkoxy($C_{1-6}$)alkoxy or phenoxy; or —$CO_2R^{23}$ wherein values of $R^{23}$ preferably include $C_{3-7}$ cycloalkyl, aryl($C_{1-6}$) alkyl, heteroaryl($C_{1-6}$)alkyl or aryl($C_{2-6}$)alkynyl, any of which groups being optionally substituted with hydroxy or $C_{1-6}$ alkoxy.

Additional preferred compounds within the scope of Formula IV include those of Formula IV wherein $R_1$ is cyano, trifluoromethyl, trifluoromethylsulfonyl or 1-alkynyl, $R'_6$ and $R'_7$ independently represent hydrogen, fluoro, chloro, bromo, methyl, trifluoromethyl or nitro, and $R'_8$ is hydrogen.

Most preferred are those compounds wherein $R'_5$ is hydrogen or chloro, $R'_6$ is hydrogen, $R'_7$ is chloro and $R'_8$ is hydrogen. Especially preferred compounds within the scope of Formula IV include 6,7-dichloro-3-phenyl-1,2- dihydroquinoxalin-2-one-4-oxide, 6,7-dichloro-3-(4'-methoxyphenyl)-1,2-dihydroquinoxalin-2-one-4-oxide, 6,7-dichloro-3-(3'-methoxyphenyl)-1,2-dihydroquinoxalin-2-one-4-oxide, 6,7-dichloro-3-(2'-methoxyphenyl)-1,2-dihydroquinoxalin-2-one-4-oxide, 6,7-dichloro-3-(3'-methylphenyl)-1,2-dihydroquinoxalin-2-one-4-oxide, 6,7-dichloro-3-(3'-phenoxyphenyl)-1,2-dihydroquinoxalin-2-one-4-oxide, 3-cyano-6,7-dichloro-1,2-dihydroquinoxalin-2-one-4-oxide, 6,7-dichloro-3-(4'-hydroxyphenyl)-1,2-dihydroquinoxalin-2-one-4-oxide, and 6,7-dichloro-3-(2'-hydroxyphenyl)-1,2-dihydroquinoxalin-2-one-4-oxide.

In general, preferred compounds having high binding to the glycine receptor are substituted in each available position (5-, 6- and 7-positions) except for the 8-position which must be hydrogen or fluorine. It is important that when the 8-position is a —CH— group, that the group is either unsubstituted or substituted only by fluorine in order to avoid steric interference with the interaction of the NH in the 1-position with the receptor (probably by hydrogen bonding). Preferred compounds may also have electron withdrawing substituents, such as $NO_2$ in the 5-position, and/or 6,7-substituents, such as, halogen and alkyl. N-oxides or electron withdrawing substituents in the 5-position are also very important to render the NH acidic, which is critical for the formulation of the compounds in aqueous basic solution. The aza(N-oxy) group is considered to function as an electron withdrawing substituent similar to $NO_2$, and can replace the —CH— group at any of the 5, 6, 7 or 8-positions. The replacement of the CH with N at the 8-position does not introduce any steric interference effect. It is therefore expected that the (N-oxy)pyridine analogs of 3-substituted 4-hydroxydihydroquinolin-2-ones, and tetrahydroquinaline-trione-oximes described herein should behave similarly to the corresponding 3-substituted 4-hydroxydihydroquinolin-2-ones, and tetrahydroquinaline-trione-oximes that have high binding to the glycine receptor. It is also expected that the (N-oxy)pyridine analogs of 3-substituted 4-hydroxydihydroquinolin-2-ones, and tetrahydroquinaline-trione-oximes will be easier to formulate in pharmaceutical compositions that are soluble in aqueous solutions, compared to 3-substituted 4-hydroxydihydroquinolin-2-ones, and tetrahydroquinaline-trione-oximes themselves, especially for those having an aza group in the 5-position. Since log $P_{benzene}$=2.15, log $P_{pyridine}$=0.65 and log $P_{pyridine\ N-oxide}$=−1.69 (see, Leo et al., Chem. Rev. 71:525 (1971)), there is a difference in log P of −1.50 from benzene to pyridine and −3.84 from benzene to pyridine N-oxide. It is therefore expected that the pyridine and pyridine N-oxide analogs of the hydroxyquinolones, dihydroquinolones and tetrahydroquinolines will have a lower log P and will be more water soluble compared to the corresponding hydroxyquinolones, dihydroquinolones and tetrahydroquinolines.

The compounds of the present invention are expected to be potent anticonvulsants in animal models and will prevent ischemia-induced nerve cell death in the gerbil global ischemia model after i.p. or i.v. administration. The compounds disclosed herein are active in treating or preventing neuronal loss, neurodegenerative diseases, and chronic pain and are active as anticonvulsants and in inducing anesthesia without untoward side effects caused by non-selective binding with other receptors, particularly, kainate, AMPA, and quisqualate receptors and the PCP and glutamate receptors associated with the NMDA receptor. In addition, these compounds are effective in treating or preventing the adverse consequences of the hyperactivity of the excitatory amino acids, e.g., those that are involved in the NMDA receptor system, by blocking the glycine receptors and preventing the ligand-gated cation channels from opening and allowing excessive influx of $Ca^{++}$ into neurons, as occurs during ischemia.

Neurodegenerative diseases that may be treated with the compounds of the present invention include those selected from the group consisting of Alzheimer's disease, amyotrophic lateral sclerosis, Huntington's disease, and Down's syndrome.

The compounds of the present invention find particular utility in the treatment or prevention of neuronal loss associated with multiple strokes, which gives rise to dementia. After a patient has been diagnosed as suffering from a stroke, the compounds of the present invention may be administered to ameliorate the immediate ischemia and prevent further neuronal damage that may occur from recurrent strokes.

Additionally, the compounds of the present invention are able to cross the blood/brain barrier, which makes them particularly useful for treating or preventing conditions involving the central nervous system. The compounds of the present invention are more water soluble than prior art NMDA glycine receptor antagonists, better at crossing the blood/brain barrier, and bind plasma proteins to a much lower degree than prior art compounds, resulting in a higher bioavailability.

For a compound to begin to show in vivo efficacy and, thus, the ability to cross the blood-brain barrier, the compound should exhibit an $ED_{50}$ of less than about 100 mg/kg body weight of the animal. Preferably, the compounds of the present invention exhibit an $ED_{50}$ of less than about 20 mg/kg and, more preferably, less than about 10 mg/kg.

The compounds of the invention find particular utility in treating or preventing the adverse neurological consequences of surgery. For example, coronary bypass surgery requires the use of heart-lung machines, which tend to introduce air bubbles into the circulatory system that may lodge in the brain. The presence of such air bubbles robs neuronal tissue of oxygen, resulting in anoxia and ischemia. Pre- or post- surgical administration of the compounds of the present invention will treat or prevent the resulting ischemia. In a preferred embodiment, the compounds of the invention are administered to patients undergoing cardiopulmonary bypass surgery or carotid endarterectomy surgery.

The compounds of the present invention also find utility in treating or preventing pain, e.g., chronic pain. Such chronic pain can be the result of surgery, trauma, headache, arthritis, pain associated with terminal cases of cancer, or degenerative diseases. The compounds of the present invention find particular utility in the treatment of phantom pain that results from amputation of an extremity. In addition to treatment of pain, the compounds of the invention are also expected to be useful in inducing anesthesia, either general or local anesthesia, for example, during surgery.

The binding affinities of compounds of the present invention at NMDA receptor glycine sites can be estimated by electrophysiological assays with either cloned rat NMDA receptors expressed in Xenopus oocytes, or non-NMDA receptors expressed in oocytes by whole rat brain poly(A)$^+$ RNA. $K_i$ values are estimated by assuming competitive inhibition and assaying suppression of membrane current responses elicited by fixed concentrations of agonist: 1 mM glycine and 100 mM glutamate for NMDA receptors; 20 mM kainic acid for non-NMDA receptors. For NMDA receptors $K_i$s are approximated by averaging values at three subtype combinations (NR1A/NR2A, NR1A/NR2B, and NR1A/NR2C). See U.S. application Ser. No. 08/148,259, entitled Glycine Receptor Antagonists and the Use Thereof, supra.

Preferably, the compounds of the invention exhibit a binding affinity to the glycine binding site of $K_i$=about 10 μM or less, more preferably, 1 μM or less and more preferably, 500 nM or less, and more preferably, 100 nM or less, and most preferably, about 10 nM or less. Also preferable are compounds that exhibit binding at the kainate and AMPA sites of not less than $K_i$=1 μM and, more preferably, not less than 10 μM.

The affinity of the compounds for the NMDA receptor glycine site also was measured by inhibition of [$^3$H]DCKA binding to rat brain membranes. See, Canton, T. et al., *J. Pharm. Pharmacol.* 44:812–816 (1992).

The novel glycine antagonists can be tested for in vivo activity after intraperitoneal injection using a number of anticonvulsant tests in mice (audiogenic seizure model in DBA-2 mice, pentylenetetrazol-induced seizures in mice, NMDA-induced death in mice, and MES in mice). Preferred compounds exhibit ataxia side effects in the rotorod ataxia test at dosage levels of greater than about 10 mg/kg, more preferably, greater than about 20 mg/kg.

The compounds can also be tested in drug discrimination tests in rats trained to discriminate PCP from saline. It is expected that most of the compounds will not generalize to PCP at any dose. In addition, it is also expected that none of the compounds will produce a behavioral excitation in locomotor activity tests in the mouse. It is expected that such results will suggest that the glycine antagonists of the present invention do not show the PCP-like behavioral side effects that are common to NMDA channel blockers such as MK-801 and PCP or to competitive NMDA antagonists such as CGS 19755.

The glycine and excitatory amino acid antagonists are also expected to show potent activity in vivo after intraperitoneal injection suggesting that these compounds can penetrate the blood/brain barrier.

It is well known to use opiates, e.g., morphine, in the medical field to alleviate pain. (As used herein, the term "opiates" is intended to mean any preparation or derivative of opium, especially the alkaloids naturally contained therein, of which there are about twenty, e.g., morphine, noscapine, codeine, papaverine, and thebaine, and their derivatives.) Unfortunately, with continued use, the body builds up a tolerance for the opiate, and, thus, for continued relief, the patient must be subjected to progressively larger doses. Tolerance develops after both acute and chronic morphine administration (Kornetsky et al., *Science* 162:1011–1012 (1968); Way et al., *J. Pharmacol. Exp Ther.* 167:1–8 (1969); Huidobro et al., *J. Pharmacol. Exp Ther.* 198:318–329 (1976); Lutfy et al., *J. Pharmacol. Exp Ther.* 256:575–580 (1991)). This, in itself, can be detrimental to the patient's health. Furthermore, a time can come when the tolerance is substantially complete and the pain killing properties of the drug are no longer effective. Additionally, administration of higher doses of morphine may lead to respiratory depression, causing the patient to stop breathing. Seeking alternative drugs to produce analgesia without development of tolerance or as an adjunct therapy to block tolerance without interference with analgesia is an active area of research.

Recent studies have suggested a modulatory role for the NMDA receptor in morphine tolerance. (Trujillo et al., *Science* 251:85–87 (1991); Marek et al., *Brain Res.* 547:77–81 (1991); Tiseo et al., *J. Pharmacol. Exp Ther.* 264:1090–1096 (1993); Lutfy et al., *Brain Res.* 616:83–88 (1993).) The present invention is also directed to the administration of the compounds described herein to inhibit opiate tolerance by blocking the glycine co-agonist site associated with the NMDA receptor.

The compounds of the present invention may be tested for potential glycine antagonist activity by observing the inhibition of binding of 1 μM glycine-stimulated [$^3$H]-MK-801 in rat or guinea pig brain membrane homogenates. The more potent the glycine antagonist, the less [$^3$H]-MK-801 can bind since the [$^3$H]-MK801 binding site (PCP receptor) is accessible only upon opening of the ion channel by glutamate and glycine (Fletcher, E. L., et al., in *Glycine Neurotransmission*, Otterson, P., et al., eds., John Wiley and Sons (1990); Johnson, J. W., et al., *Nature* 325:529 (1987)).

The compounds of the present invention may be prepared as follows. A starting material for preparing 5-aza and 5-aza(N-oxy) analogs of 3-substituted 4-hydroxydihydroquinolin-2-ones is 3-aminopicolinic acid. 3-Aminopicolinic acid can be prepared according to Nakadate et al. by Hofmann rearrangement of 2,3-pyridinecarboximide (*Chem. Pharm. Bull.* 13:113–118 (1965)). 5-Substituted 3-aminopicolinic acid can be prepared from 2-amino-5-substituted pyridine as shown in Scheme I. Substitutions on the pyridine ring can be introduced by employing the appropriate substituted 3-aminopicolinic acid. For example, chlorination of 3-aminopicolinic acid yields the desired 3-amino-5-chloropicolinic acid. Alternatively, 5-substituted 3-aminopicolinic acid is prepared from 5-substituted 2,3-pyridinedicarboxylic anhydride.

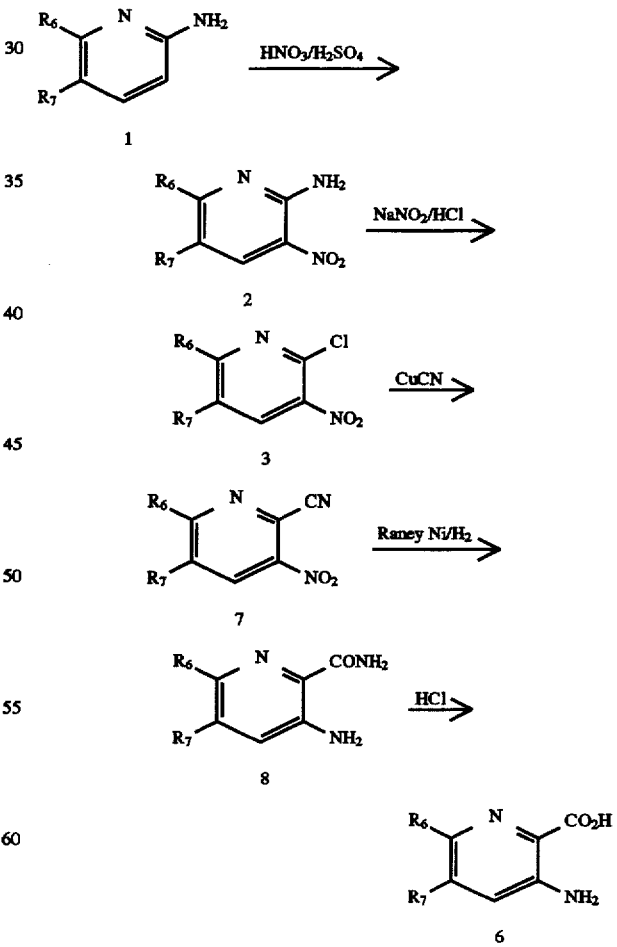

Scheme I wherein $R_6$ and $R_7$ are defined above. In this reaction $R_7$ is preferably one of hydrogen, methyl, chloro, bromo, iodo, nitro, trifluoromethyl, carboxy, carbamoyl or sulfonic acid and $R_6$ is preferably hydrogen.

The general reaction scheme for synthesizing the 5-(N-oxy)aza analogs of 3-substituted 4-hydroxy-dihydroquinolin-2-ones is as follows:

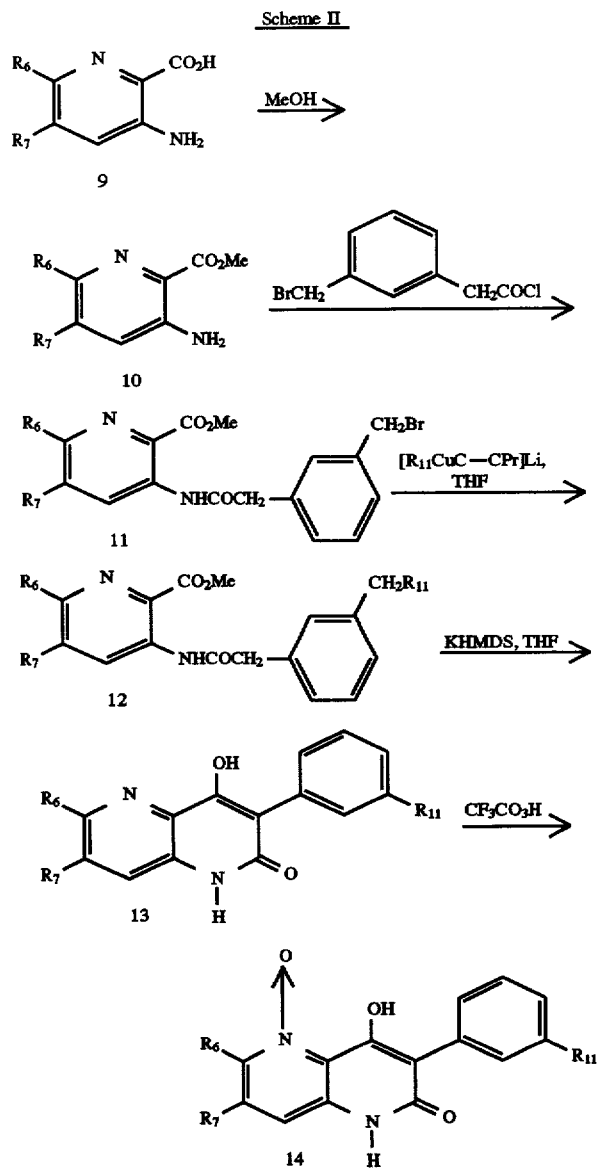

wherein $R_6$, $R_7$ and $R_{11}$ are as defined above. In this reaction $R_6$ is preferably hydrogen, $R_7$ is preferably either chlorine or hydrogen, and $R_{11}$ is preferably benzyl, 4-methoxybenzyl or 4-methoxymethoxybenzyl.

Alternatively, the N-oxide group may be introduced in an earlier stage of the preparation, such as shown in Scheme III.

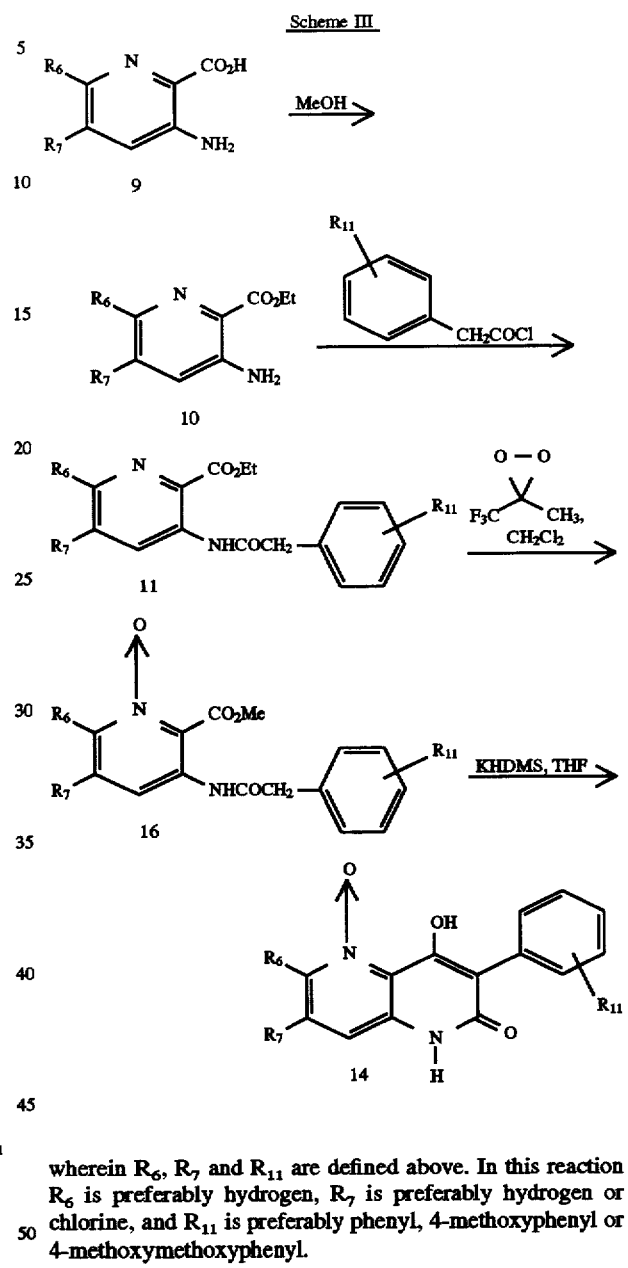

wherein $R_6$, $R_7$ and $R_{11}$ are defined above. In this reaction $R_6$ is preferably hydrogen, $R_7$ is preferably hydrogen or chlorine, and $R_{11}$ is preferably phenyl, 4-methoxyphenyl or 4-methoxymethoxyphenyl.

The general reaction scheme for synthesizing the 5-aza (N-oxy) analogs of 3nitro-4-hydroxy-dihydroquinolin-2-ones or 1,2,3,4-tetrahydroquinoline-2,3,4-trione-3-oximes is as follows:

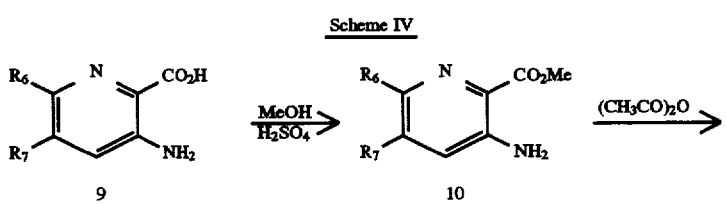

-continued
Scheme IV
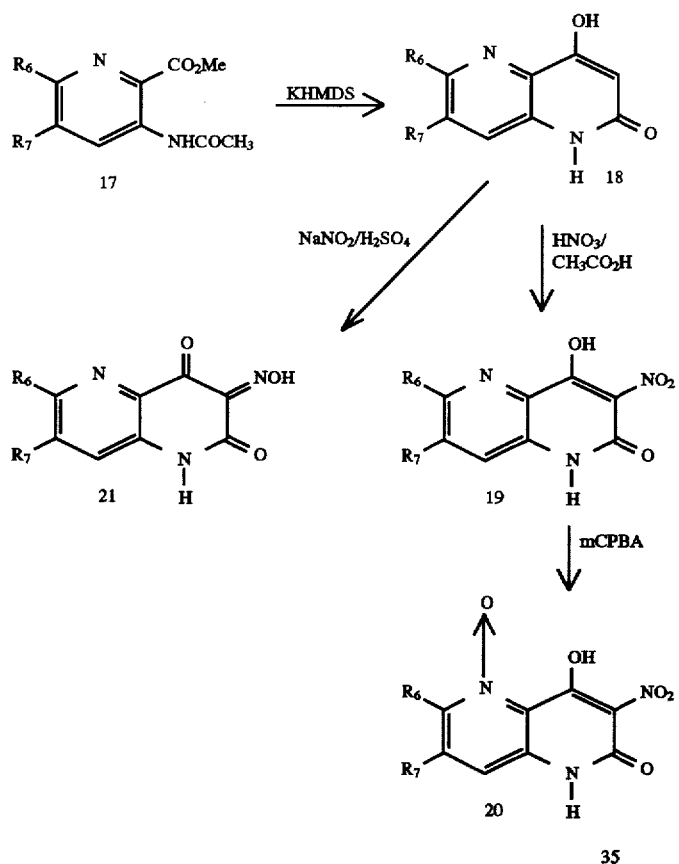
wherein $R_6$ and $R_7$ are defined above. In this reaction, $R_6$ is preferably hydrogen, and $R_7$ is preferably hydrogen or chlorine.
Alternatively, the N-oxide group may be introduced in an earlier stage of the preparation, such as shown in Scheme V.
Scheme V
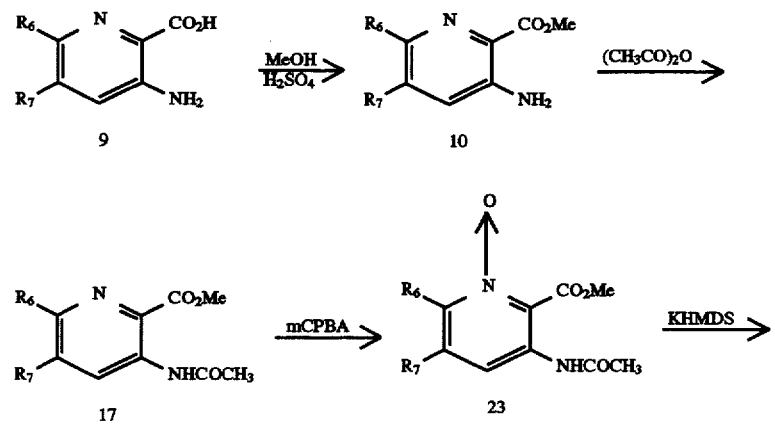

-continued
Scheme V

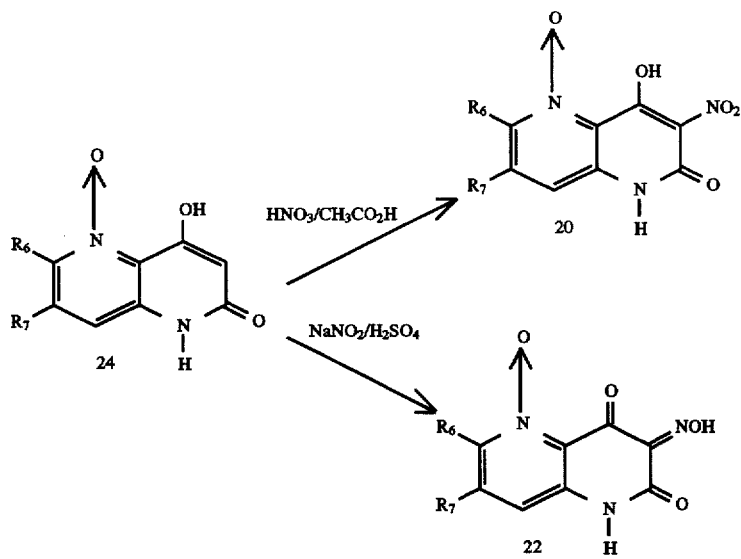

The general scheme for synthesizing nitrone derivatives of quinoxalines is as follows:

Scheme VI

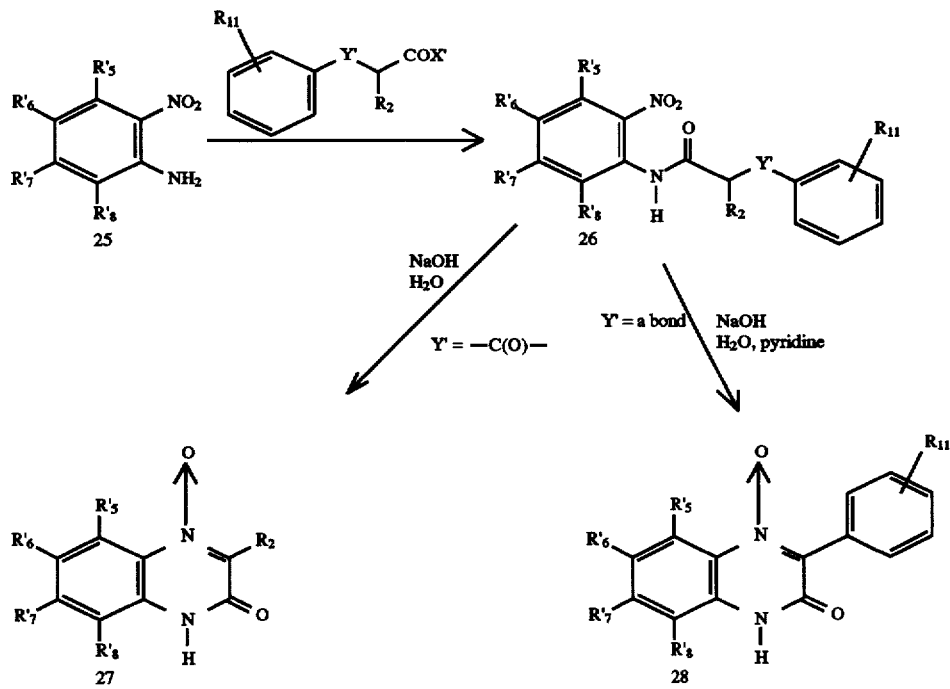

wherein R'$_5$, R'$_6$, R'$_7$, R'$_8$ and R$_2$, are as defined above for Formula IV, X' represents chlorine or bromine, Y' represents a bond or —C(O)—, and R$_{11}$ is as defined above for Formula Ie.

Commercially available substituted phenylacetic acids are employed as starting material. They are converted into acyl chlorides, that in turn are used for acylation of the starting o-nitro anilines to form open-chain amides. The open-chain amides are treated with a strong base, such as sodium hydroxide, in a water-pyridine mixture to form phenyl nitrones, analogous to conditions used in Ahmad, Y. et al., Tetrahedron 21:861 (1965).

To prepare aldonitrones (R$_2$ is H) or alkyl nitrones (R$_2$ is C$_{1-4}$ alkyl), the starting nitroaniline is reacted with ethyl benzoylacetate or alkyl substituted benzoylacetate ethyl ester, respectively, at a temperature of between about 160° and about 170° C. The intermediate amide loses a benzoyl group under the cyclization conditions to give the compound of interest, as it was reported for a structural analog in Tennant, G., *J. Chem. Soc.*:2428 (1963).

To prepare 3-cyano nitrone derivatives ($R_2$ is CN), the starting nitroaniline is reacted with cyanoacetyl chloride to form the open-chain amide, which is thereafter cyclized.

Compounds having the formula IVb can be prepared similarly using phenylacetic acids bearing the tautomeric fragment ($R_2$) in protected form. Suitable oxygen and sulfur protective groups are well-known in the art.

Compounds having the formula IVg can be prepared according to the following synthetic scheme (Scheme VII) based upon a scheme reported by Martin and Volodarskii, *Izv. Akad. Nauk SSSR, Ser. Khim.* (6):1336 (1980).

Scheme VII

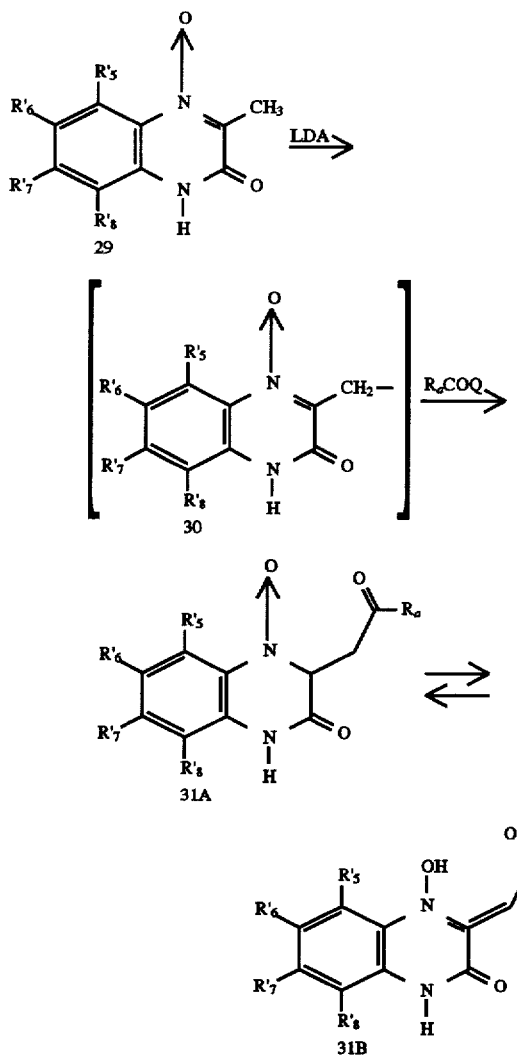

wherein $R'_5$, $R'_6$, $R'_7$ and $R'_8$ are as defined above for Formula IV and $R_aCOQ$ is an electrophilic acylating reagent.

Methyl nitrone (29), as prepared above, is deprotonated with an excess of LDA (lithium diisopropylamide) to provide a resonance-stabilized anion, that is then allowed to react with an electrophilic acylating reagent ($R_aCOQ$) to afford a nitrone compound having an acylmethyl moiety in the $R_2$ position. Alternatively, the resonance-stabilized anion may be allowed to react with $R_aONO$ or $R_aONO_2$ to give an oxime or —$CH_2NO_2$, respectively. $R_a$ is defined as above for formula IVb.

Scheme VIII describes the synthesis of the intermediate quinoxaline-aldonitrone 34. Acylation of an o-nitro aniline 32 with ethyl benzoylacetate gives open-chain o-nitroanilide 33. This compound is cyclized upon treatment with hot aqueous alkaline solution to give the nitrone 34. In these preparations a modification of the procedure disclosed by Tennant, G., *J. Chem. Soc.*:2428 (1963) was used.

Scheme VIII

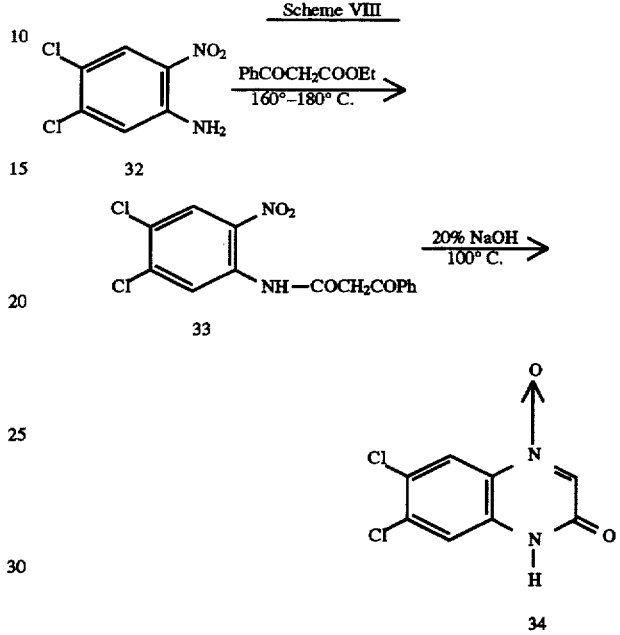

Scheme IX describes the syntheses of quinoxaline phenyl nitrones 38, starting with substituted phenylacetic acids 35. These acids were converted into acyl chlorides 36, that were not isolated and purified. Instead, acyl chlorides 36 were reacted with o-nitroaniline 32 to give open-chain o-nitroanilides 37. These compounds were easily separated from the starting reactants on the basis of their low solubility in ether. Cyclization of the compound 37 into nitrones 38 was achieved by treatment with base in water-pyridine solution, using a modification of the procedure disclosed by Ahmad, Y. et al., *Tetrahedron* 21:861 (1965).

Scheme IX

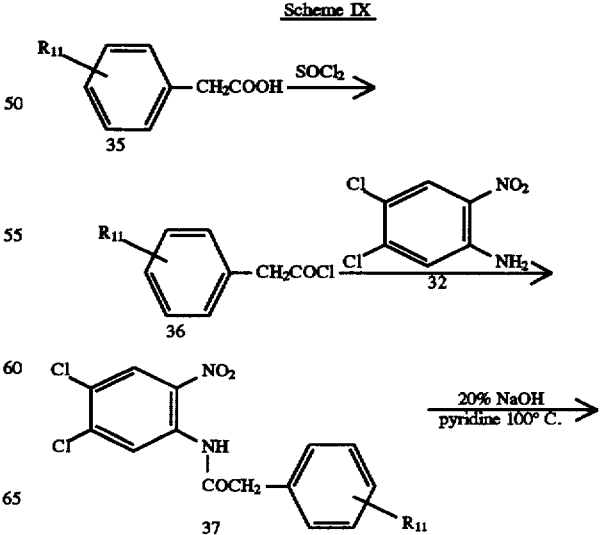

Scheme IX -continued

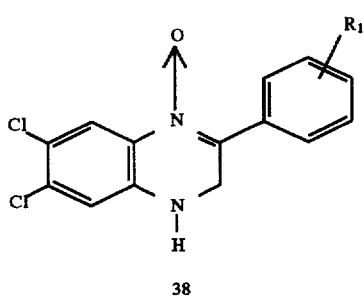

Scheme X illustrates an alternative method of preparing phenyl nitrones (38). Aldonitrone 34 was treated with excess of a Grignard reagent to give hydroxylamine derivatives 39. These compounds were not isolated or purified, but were directly oxidized into targeted phenyl nitrones 38.

Scheme X

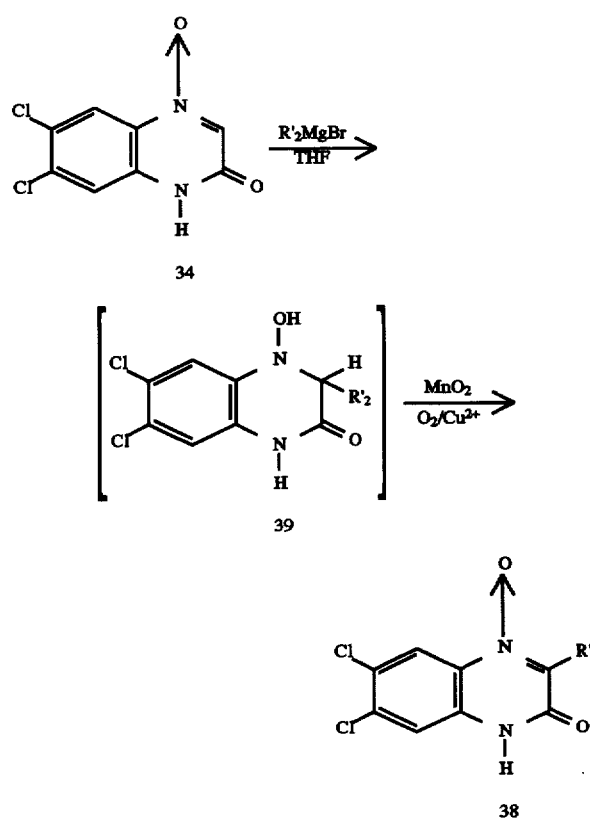

wherein R'$_2$ represents phenyl or substituted phenyl.

In Scheme XI hydroxyphenyl substituted nitrones of the IVb sub-class were prepared. Treatment of the methoxy-substituted phenyl nitrone 40 with boron tribromide led to dimethylation to give the hydroxyphenyl substituted nitrone 41.

Scheme XI

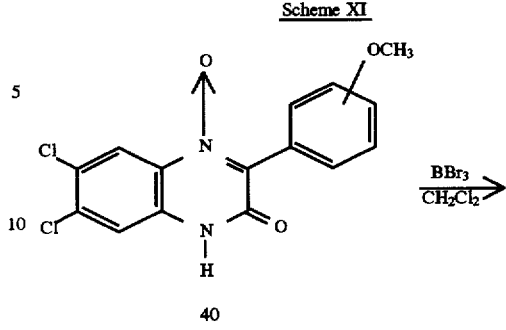

To prepare the 8-aza(N-oxy) analogs, 2-aminonicotinic acid (available from Aldrich) is employed as a starting material. The 2-aminonicotinic acid is substituted for 3-aminopicolinic acid in the general synthesis schemes shown above. The 6-aza(N-oxy) analogs may be prepared by substituting 4-amino-3-pyridinecarboxylic acid for 3-aminopicolinic acid in the general synthesis schemes. The 7-aza(N-oxy) analogs may be prepared by substituting 3-amino-4-pyridinecarboxylic acid for 3-aminopicolinic acid in the general synthesis schemes. Methods for preparing the 4-amino-3-pyridinecarboxylic acid and 3-amino-4-pyridinecarboxylic acid starting materials are taught in Hurd et al., J. Org. Chem. 35:1471 (1970), and Tserng et al., J. Heterocycl. Chem. 9:1433 (1972). The diaza (N-oxy) analogs can be prepared by analogous methods.

The N-oxides may be prepared by oxidation of the pyridine nitrogen by peracetic acid (Israel & Day, J. Org. Chem. 24:1455–1460 (1959)), or by oxidation with m-chloroperbenzoic acid (mCPBA) (Daines, R. A., et al., J. Med. Chem. 36:3321–3332 (1993)). Alternatively, the N-oxide may be introduced prior to cyclizing by reacting a pyridyl intermediate with methyl(trifluoromethyl)dioxirane.

One of ordinary skill in the art would be able to synthesize 5-aza(N-oxy), 6-aza(N-oxy), 7-aza(N-oxy) and 8-aza(N-oxy) analogs falling within the scope of the claims in view of the disclosed reaction schemes and generally known organic synthetic techniques.

Thus, the present invention is directed to compounds having high binding to the glycine receptor and low binding to the kainate and AMPA sites. Particular compounds of the invention may have high antagonist potency at the kainate, AMPA, and quisqualate receptors in addition to the glycine receptor. According to the present invention, those compounds having high binding to the glycine receptor exhibit a glycine binding affinity ($K_i$) of about 100 µM or less in a glycine binding assay. Preferably, the compounds of the present invention exhibit a $K_i$ of 10 µM or less. Most preferably, the compounds of the present invention exhibit a $K_i$ of 1 µM or less. The compounds exhibit high binding to the kainate and AMPA sites if they exhibit a $K_i$ of about 10 µM or less, especially, 1 µM or less in a kainate or AMPA binding assay.

The present invention also relates to the discovery that certain 5-aza-4-hydroxy-3-arylquinoline-2-ones have high affinity for the glycine/NMDA receptor and have in vivo activity as an anticonvulsant in MES experiment in mice. For instance, 5-aza-7-chloro-4-hydroxy-3-(m-phenoxyphenyl)quinoline-2-one was found to have a $K_i$ of 5 nM in the glycine/NMDA receptor and $ED_{50}$ of 3 mg/kg as an anticonvulsant in a MES experiment in mice.

The present invention also relates to the discovery that certain 3-substituted-1,2-dihydroquinoxaline-2-one-4-oxides have high affinity for the glycine/NMDA receptor and have in vivo activity as an anticonvulsant in a MES experiment in mice. For instance, 6,7-dichloro-3-cyano-1,2-dihydroquinoxaline-2-one-4-oxide was found to have an $IC_{50}$ of 135 nM in [$^3$H]DCKA binding and an $ED_{50}$ of 5 mg/kg as an anticonvulsant in a MES experiment in mice.

The glycine antagonist potency in vitro may be determined using a 1 μM glycine-stimulated [$^3$H]-MK801 binding assay. This assay takes advantage of the fact that the binding of [$^3$H]-MK801 to the PCP receptor inside the pore of the NMDA channel is dependent on the presence of both glutamate and glycine. In the absence of glycine, but in the presence of glutamate, [$^3$H]-MK801 cannot bind effectively to the PCP receptor, because the NMDA channel remains closed and access of [$^3$H]-MK801 to the PCP receptor inside the closed channel pore is severely restricted.

The assay is conducted using rat brain membrane homogenates that are enriched in NMDA receptors. The membranes are prepared as follows. Frozen rat brains (obtained from Pel-Freez, Rogers, Ark.) are homogenized in 15 volumes (w/v) of ice cold 0.32M sucrose. The homogenate is spun at 1,000×g for ten minutes. The supernatant is collected and spun for 20 minutes at 44,000×g. The pellet is suspended in 15 volumes of water (relative to original brain weight). The homogenate is again spun at 44,000×g for twenty minutes. The pellet is resuspended in 5 volumes of water and the suspension is freeze-thawed 2 times. After the final thaw cycle, the suspension is brought to 15 volumes with water and spun at 44,000×g for twenty minutes. The pellet is resuspended in 5 volumes of ice-cold 10 mM HEPES, and is titrated to pH 7.4 with KOH containing 0.04% Triton X-100. Membranes are incubated with the Triton/HEPES buffer at 37° C. for 15 minutes. The volume is then brought to 15 with ice-cold 10 mM HEPES, pH 7.4, and spun/washed three times with spins of 44,000×g between washes. The final pellet is suspended in three volumes of 50 mM HEPES, pH 7.4 and the protein concentration is determined with a standard dye-binding protein assay (Bio-Rad, Richmond, Calif.). The suspension is stored at −80° C. until used. Only HPLC grade water is used for all buffers and suspensions/washings. The extensive washings are necessary to remove as much endogenous glycine from the membrane preparation as possible.

On the day of the assay, the previously prepared membranes are thawed and 5 mM Tris/HCl buffer, pH 7.4, is added to yield a final protein concentration of 0.156 mg/mL. For binding assays, 0.8 mL of membranes are pipetted into polypropylene tubes followed by 0.033 mL of 15.1 μM 5,7-dichlorokynurenic acid (DCK), 0.033 mL of 30.3 μM glycine in buffer (or buffer alone), 0.033 mL of 303 μM glutamate in buffer (or for controls, 0.1 mL 1 mM PCP instead of DCK/gly/glu), 0.033 mL glycine antagonist in buffer (or buffer alone) and 0.1 mL buffer containing 200,000 cpm [$^3$H]-MK801. Nonspecific binding is defined as the difference in binding that occurs in the absence or presence of PCP (final concentration: 100 μM). To determine the effect of 1 μM glycine on the binding of [$^3$H]-MK801, bound radioactivity in the presence of 10 μM glutamate alone (final concentration) is subtracted from the bound radioactivity in the presence of both 10 μM glutamate and 1 μM glycine (final concentration). A 500 nM concentration (final) of 5,7-dichlorokynurenic (DCK) acid is added to all assay tubes. This concentration of the glycine antagonist DCK "buffers" most of the residual endogenous glycine that is not removed by the extensive washing steps that are carried out during the membrane preparation procedure. The 500 nM DCK does not interfere with the stimulation of [$^3$H]-MK801 binding that is effected by the addition of 1 μM exogenous glycine.

The assays are incubated for 120 minutes at room temperature after which time the membrane-bound radioactivity is isolated from the free radioactivity by vacuum filtration through Whatman glass fiber filters that had been pretreated with 0.3% polyethyleneimine. Filtration is accomplished using a Brandel 48 well cell harvester. Filtered membranes are washed three times with 3 mL each of ice cold buffer. Filters are transferred to scintillation vials and 5 mL of scintillation cocktail is added. The vials are shaken overnight and the radioactivity is counted by liquid scintillation spectroscopy. The assays are done in triplicate and all experiments are conducted at least three times.

Inhibition dose response curves are constructed using increasing concentrations of glycine antagonists from 5 nM to 330 μM. $IC_{50}$ values are determined for compounds active in inhibiting 1 μM glycine-stimulated [$^3$H]-MK801 binding by computer-assisted plotting of the inhibition curves and interpolation. When compounds are found to inhibit glycine-stimulated [$^3$H]-MK801 binding, experiments are conducted to determine whether the inhibition of the glycine-stimulated [$^3$H]-MK801 binding is indeed mediated at the glycine binding site of the NMDA receptor. In these experiments, a fixed concentration of antagonist sufficient to produce a >95% inhibition of the 1 μM glycine-stimulated [$^3$H]-MK801 binding is incubated with the membranes without any additional glycine (above 1 μM) and in the presence of increasing concentrations of additional glycine (2 μM to 1 μM). If the inhibition of [$^3$H]-MK801 binding by the drug in the presence of 1 μM glycine is fully reversed by adding increasing concentrations of glycine, then the inhibition of [$^3$H]-MK801 binding is mediated by the drug acting as an antagonist at the glycine binding site of the NMDA receptor.

After constructing inhibition dose response curves and determination of glycine reversibility, $K_i$ values for the glycine antagonists are calculated using the Cheng and Prusoff equation employing the experimentally determined $IC_{50}$ values, the known concentration of glycine in the assay (1 μM) and the known affinity of glycine for the glycine binding site of the NMDA receptor (100 nM).

The same rat brain membrane homogenates used for the 1 μM glycine-stimulated [$^3$H]-MK801 binding assay are used for the [$^3$H]-AMPA radioligand binding assay. On the day of the assay the frozen membranes (prepared as described above) are thawed and diluted with 30 mM Tris/HCl buffer containing 2.5 mM $CaCl_2$ and 100 mM KSCN, pH 7.4, to yield a final membrane concentration of 1.25 mg/mL membrane protein. For the binding assay, 0.8 mL of membrane homogenate is added to polypropylene tubes followed by 0.033 mL drug and 0.067 mL buffer (or for controls by 0.1 mL buffer alone) and 0.1 mL buffer containing 200,000 cpm of [$^3$H]-AMPA. The assay is incubated for 30 minutes on ice. Bound radioactivity is separated from free radioactivity by filtration over Whatman glass fiber filters (pre-treated with 0.3% polyethyleneimine) using a Brandel 48 well cell harvester.

Filtered membranes are washed three times with 3 mL each of ice cold buffer. The filters are transferred to scintillation vials and 5 mL of scintillation cocktail is added. The vials are shaken overnight and radioactivity is counted by liquid scintillation spectroscopy. Nonspecific binding is determined by the radioactivity that remains bound to the membranes in the presence 10 mM glutamate. Inhibition dose response curves are constructed by adding increasing concentrations of drug from 10 nM to 100 µM.

The same membrane preparation as that used for the [$^3$H]-AMPA binding assay may be used for the [$^3$H]-kainate radioligand binding assay. On the day of the assay the frozen rat brain membranes are thawed and 5 mM Tris/HCl buffer, pH 7.4, is added to yield a final concentration of 0.5 mg/mL membrane protein. For the binding assay, 0.8 mL of membrane homogenate is added to polypropylene tubes followed by 0.033 mL drug and 0.067 mL buffer (or for controls by 0.1 mL buffer alone) and 0.1 mL buffer containing 200,000 cpm of [$^3$H]-kainate. The assay is incubated for 2 hours on ice. Bound radioactivity is separated from free radioactivity by filtration over Whatman glass fiber filters (pretreated with 0.3% polyethyleneimine) using a Brandel 48 well cell harvester. Filtered membranes are washed three times with 3 mL each of ice cold buffer. The filters are transferred to scintillation vials and 5 mL of scintillation cocktail is added. The vials are shaken overnight and radioactivity is counted by liquid scintillation spectroscopy. Nonspecific binding is determined by the radioactivity that remains bound to the membranes in the presence 10 mM glutamate. Inhibition dose response curves are constructed by adding increasing concentrations of drug from 250 nM to 330 µM.

The binding affinities at NMDA receptor glycine sites also were estimated by electrophysiological assay either using cloned rat NMDA receptors expressed in Xenopus oocytes, or non-NMDA receptors expressed in oocytes by whole rat brain poly(A)$^+$ RNA. See U.S. application Ser. No. 08/148,259, filed Nov. 5, 1993 U.S. Pat. No. 5,514,680. $K_b$ values were estimated by assuming competitive inhibition and assaying suppression of membrane current responses elicited by fixed concentrations of agonist: 1 mM glycine and 100 mM glutamate for NMDA receptors; 20 mM kainic acid for non-NMDA receptors. For NMDA receptors $K_b$s were approximated by averaging values at three subtype combinations (NR1A/NR2A, NR1A/NR2B, and NR1A/NR2C).

The anxiolytic activity of any particular compound of the present invention can be determined by use of any of the recognized animal models for anxiety. A preferred model is described by Jones, B. J., et al., Br. J. Pharmacol. 93:985–993 (1988). This model involves administering the compound in question to mice that have a high basal level of anxiety. The test is based on the finding that such mice find it aversive when taken from a dark home environment in a dark testing room and placed in an area painted white and brightly lit. The test box has two compartments, one white and brightly illuminated and one black and non-illuminated. The mouse has access to both compartments via an opening at floor level in the divider between the two compartments. The mice are placed in the center of the brightly illuminated area. After locating the opening to the dark area, the mice are free to pass back and forth between the two compartments. Control mice tend to spend a larger proportion of time in the dark compartment. When given an anxiolytic agent, the mice spend more time exploring the more novel brightly lit compartment and exhibit a delayed latency to move to the dark compartment. Moreover, the mice treated with the anxiolytic agent exhibit more behavior in the white compartment, as measured by exploratory rearings and line crossings. Since the mice can habituate to the test situation, naive mice should always be used in the test. Five parameters can be measured: the latency to entry into the dark compartment, the time spent in each area, the number of transitions between compartments, the number of lines crossed in each compartment, and the number of rears in each compartment. The administration of the compounds of the present invention is expected to result in the mice spending more time in the larger, brightly lit area of the test chamber.

In the light/dark exploration model, the anxiolytic activity of a putative agent can be identified by the increase of the numbers of line crossings and rears in the light compartment at the expense of the numbers of line crossings and rears in the dark compartment, in comparison with control mice.

A second preferred animal model is the rat social interaction test described by Jones, B. J. et al., supra, wherein the time that two mice spend in social interaction is quantified. The anxiolytic activity of a putative agent can be identified by the increase in the time that pairs of male rats spend in active social interaction (90% of the behaviors are investigatory in nature). Both the familiarity and the light level of the test arena can be manipulated. Undrugged rats show the highest level of social interaction when the test arena is familiar and is lit by low light. Social interaction declines if the arena is unfamiliar to the rats or is lit by bright light. Anxiolytic agents prevent this decline. The overall level of motor activity may also be measured to allow detection of drug effects specific to social behaviors.

The efficacy of the glycine and excitatory amino acid antagonists to inhibit glutamate neurotoxicity in a rat brain cortex neuron cell culture system can be determined as follows. An excitotoxicity model modified after that developed by Choi (Choi, D. W., J. Neuroscience 7:357 (1987)) can be used to test anti-excitotoxic efficacy of the glycine and excitatory amino acid antagonists. Fetuses from rat embryonic day 19 are removed from time-mated pregnant rats. The brains are removed from the fetuses and the cerebral cortex is dissected. Cells from the dissected cortex are dissociated by a combination of mechanical agitation and enzymatic digestion according to the method of Landon and Robbins (Methods in Enzymology 124:412 (1986)). The dissociated cells are passed through an 80 micron nitex screen and the viability of the cells are assessed by Trypan Blue. The cells are plated on poly-D-lysine coated plates and incubated at 37° C. in an atmosphere containing 91% $O_2$/9% $CO_2$. Six days later, fluoro-d-uracil is added for two days to suppress non-neural cell growth. At culture day 12, the primary neuron cultures are exposed to 100 µM glutamate for 5 minutes with or without increasing doses of glycine and excitatory amino acid antagonist or other drugs. After 5 minutes, the cultures are washed and incubated for 24 hours at 37° C. Neuronal cell damage is quantitated by measuring the lactate dehydrogenase (LDH) activity that is released into the culture medium. The LDH activity is measured according to the method of Decker et al. (Decker et al., J. Immunol. Methods 15:16 (1988)).

The anticonvulsant activity of the glycine and excitatory amino acid antagonists can be assessed in the audiogenic seizure model in DBA-2 mice as follows. DBA-2 mice can be obtained from Jackson Laboratories, Bar Harbor, Me. These mice at an age of <27 days develop a tonic seizure within 5–10 seconds and die when they are exposed to a sound of 14 kHz (sinus wave) at 110 dB (Lonsdale, D., Dev. Pharmacol. Ther. 4:28 (1982)). Seizure protection is defined when animals injected with drug 30 minutes prior to sound exposure do not develop a seizure and do not die during a 1 minute exposure to the sound. 21 day old DBA-2 mice are used for all experiments. Compounds are given intraperitoneally in either saline, DMSO, or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The anticonvulsant efficacy of the glycine receptor antagonists can be assessed in the pentylenetetrazol (PTZ)-induced seizure test as follows. Swiss/Webster mice, when injected with 50 mg/kg PTZ (i.p.) develop a minimal clonic seizure of approximately 5 seconds in length within 5–15 minutes after drug injection. Anticonvulsant efficacy of a glycine/excitatory amino acid antagonist (or other) drug is defined as the absence of a seizure when a drug is given 30 minutes prior to PTZ application and a seizure does not develop for up to 45 minutes following PTZ administration. Glycine/excitatory amino acid antagonist or other drugs are given intraperitoneally in either saline, DMSO, or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The efficacy of glycine/excitatory amino acid antagonists to protect mice from NMDA-induced death may be assessed as follows. When mice are injected with 200 mg/kg N-methyl-D-aspartate (NMDA) i.p., the animals will develop seizures followed by death within 5–10 minutes. Glycine/excitatory amino acid antagonists are tested for their ability to prevent NMDA-induced death by giving the drugs i.p. 30 minutes prior to the NMDA application. Glycine/excitatory amino acid antagonist or other drugs are given intraperitoneally in either saline, DMSO, or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The anticonvulsant activity of the glycine antagonists may be assessed in the maximum electroshock-induced seizure (MES) assay in mice. Electroshock was applied to male Swiss/Webster mice (20–30 g, Simonsen) through corneal electrodes (Swinyard, E. A., in Anticonvulsant Drugs, Mercier, J., ed., Pergamon Press, Oxford (1973), pp. 47–65). The seizure stimulus parameters were: 50 mA, 60 Hz, rectangular pulse, width 0.8 msec, duration 200 msec. Tonic hind limb extension observed after application of the electrical stimulus was recorded as occurrence of seizure. The drug was applied i.v. as an aqueous basic solution.

A series of different evaluations can be conducted on doses of the glycine/excitatory amino acid antagonists of the invention to determine the biological activity of the compounds both in normal gerbils and in animals exposed to 5 minutes of bilateral carotid occlusion. See Scheme XII.

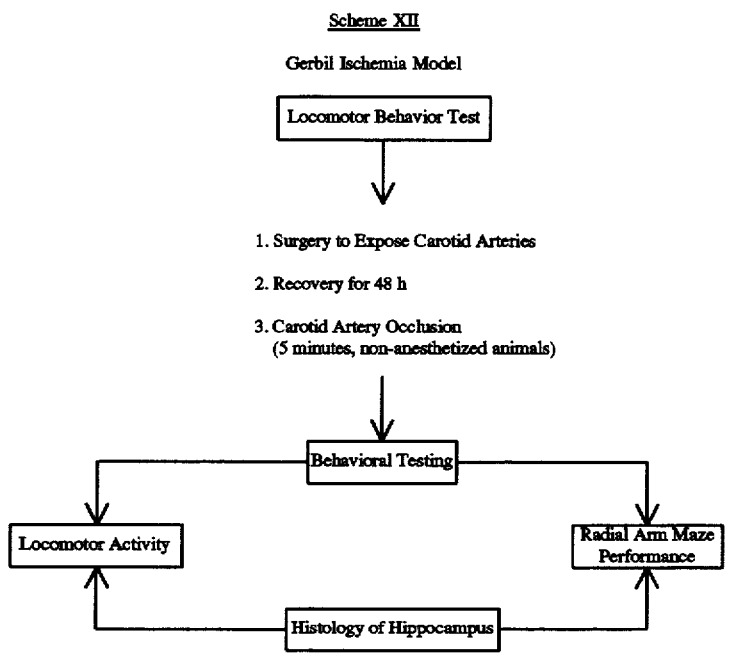

These studies are conducted in animals who are conscious and have no other pharmacological agents administered to them. Gerbils are preinstrumented 48-hours prior to ischemia to allow for the complete elimination of the pentobarbital anesthetic that is employed. When tested with drugs, animals are given IP injections of the glycine/excitatory amino acid antagonist or vehicle. In the case of multiple injections, animals are given IP injections 2 hours apart and the final injection is given 30 minutes prior to the ischemic period, or, in the case of post treatment, the animals are given injections at 30 minutes, 2 hours, 4 hours, and 6 hours post-ischemic reperfusion.

In order to assess the direct pharmacological activity or potential activity of the glycine/excitatory amino acid antagonists, naive gerbils are injected with either saline or differing doses of the antagonist. The behavioral changes are assessed using a photobeam locomotor activity chamber, which is a two foot circular diameter arena with photobeam detection. Animals are individually placed in the 2 foot diameter chambers. The chambers are housed in a closed cabinet and noise is abated using both a background white noise generator and a fan. Animals are placed in these chambers in the case of the initial pharmacological evaluation for a period of 6 hours and the total activity during each successive hour is accumulated using computer control systems.

Saline results in an initial high rate of activity, with the control animals showing a first hour activity level of about 1600 counts. This level of control activity is typical for the gerbil under these experimental conditions. As the session progresses, animals decrease their exploratory activity and at the terminal period the activity declines to about 250 counts per hour. It is expected that the glycine/excitatory amino acid antagonists of the present invention will have no significant effect on either the initial exploratory rate or the terminal rate of exploration.

In a next phase of the evaluation of the glycine/excitatory amino acid antagonists, gerbils are pretreated with varying doses of the antagonists and then exposed to a five minute period of bilateral carotid occlusion. Following the initiation of reperfusion, animals are placed into the circular locomotor activity testing apparatus and the activity at the beginning of the first hour following reperfusion is monitored for the subsequent four hours.

Control animals not exposed to ischemia and given injections of saline prior to being placed in the locomotor activity chamber show a characteristic pattern of activity that, in the first hour of locomotor activity, is substantially higher than during all other hours and progressively declines over four hours to a very low value. In contrast to the progressive decline in activity over the four hour testing period, control animals that are exposed to five minutes of cortical ischemia demonstrate a completely different pattern of locomotor activity. During the first hour, there is a significant decline in activity, followed by a progressive increase in which the activity during the fourth hour is ten-fold higher than that demonstrated by animals not exposed to carotid occlusion. These results are typical and are a reliable result of the alterations caused by five minutes of bilateral carotid occlusion in the gerbil.

Separate groups of gerbils are pretreated with the glycine/excitatory amino acid antagonists of the invention 30 minutes before the onset of carotid occlusion and then placed into the locomotor activity following one hour of reperfusion. It is expected that pretreatment of the gerbils with the glycine/-excitatory amino acid antagonists of the invention will prevent both the post-ischemic decrease and increase in activity. Post-ischemic decreases in activity are expected to be near zero during the first hour following reperfusion. Pretreatment with the glycine/excitatory amino acid antagonists of the invention is expected to reduce or prevent this early depression of behavior. In addition, the glycine/excitatory amino acid antagonists of the invention are expected to prevent the post-ischemic stimulation of behavior.

Subsequent to completion of the single dose pretreatment evaluations, gerbils are also evaluated with multiple injections of the glycine/excitatory amino acid antagonists of the invention. Doses are administered I.P. at 6 hours, 4 hours, 2 hours, and 30 minutes prior to the onset of 5 minutes of ischemia.

At 24 hours, all animals are evaluated for differences in patrolling behavior using a 8-arm radial maze. In this procedure, animals are placed into the center start chamber of the maze, the barrier removed and the amount of time and the number of times the animal makes an error recorded prior to completion of exploration in all 8 arms of the maze. An error is defined as the revisiting of an arm by an animal entering to the extent of the entire body without including its tail. If the animal perseveres or fails to leave the arm for longer than five minutes, the session is terminated. In the control population of the animals, the number of errors and exploration of the maze with no prior experience (naive) is approximately 6 errors. This is an average value for an N of 28 gerbils. Following 5 minutes of bilateral carotid occlusion and testing at 24 hours, gerbils make an average number of errors of 21. When animals are pretreated with the glycine/excitatory amino acid antagonists of the invention, there is expected to be a significant reduction in the number of errors made. There is also expected to be a significant sparing of the behavioral changes that are induced in the radial arm maze performance.

It is also expected that post treatment with the glycine/excitatory amino acid antagonists of the invention will reduce the short term memory impairment 24 hours post ischemic/reperfusion.

The effects of 5 minutes of bilateral carotid occlusion on neuronal cell death in the dorsal hippocampus may be evaluated in animals 7 days after ischemia reperfusion injury. Previous studies have demonstrated that neuronal degeneration begins to occur around 3 days following cerebral ischemia. By 7 days, those neurons that have been affected will undergo cytolysis and have either completed degeneration or are readily apparent as dark nuclei and displaced nuclei or as cells with eosinophilic cytoplasm and pycnotic nuclei. The lesion with 5 minutes of ischemia is essentially restricted within the hippocampus to the CA1 region of the dorsal hippocampus. The intermedial lateral zone of the horn is unaffected and the dentate gyrus and/or cells in CA3 do not show pathology. Gerbils are anesthetized on day 7 following ischemia with 60 mg/kg of pentobarbital. Brains are perfused transcardiac with ice-cold saline followed by buffered paraformaldehyde (10%). Brains are removed, imbedded and sections made. Sections are stained with hematoxylin-eosin and neuronal cell counts are determined in terms of number of neuronal nuclei/100 micrometers. Normal control animals (not exposed to ischemia reperfusion injury) will not demonstrate any significant change in normal density nuclei within this region. Exposure to five minutes of bilateral carotid occlusion results in a significant reduction in the number of nuclei present in the CA1 region. In general, this lesion results in a patchy necrosis instead of a confluent necrosis which is seen if 10 minutes of ischemia is employed. Pretreatment with the glycine receptor antagonists of the invention are expected to produce a significant protection of hippocampal neuronal degeneration.

It is known that NMDA receptors are critically involved in the development of persistent pain following nerve and tissue injury. Tissue injury, such as, that caused by injecting a small amount of formalin subcutaneously into the hindpaw of a test animal, has been shown to produce an immediate increase of glutamate and aspartate in the spinal cord (Skilling, S.R., et al., *J. Neurosci.* 10:1309–1318 (1990)). Administration of NMDA receptor blockers reduces the response of spinal cord dorsal horn neurons following formalin injection (Dickenson and Aydar, *Neurosci. Lett.* 121:263–266 (1991); Haley, J. E., et al., *Brain Res.* 518:218–226 (1990)). These dorsal horn neurons are critical in carrying the pain signal from the spinal cord to the brain and a reduced response of these neurons is indicative of a reduction in pain perceived by the test animal to which pain has been inflicted by subcutaneous formalin injection.

Because of the observation that NMDA receptor antagonists can block dorsal horn neuron response induced by subcutaneous formalin injection. NMDA receptor antagonists have potential for the treatment of chronic pain, such as, pain caused by surgery or by amputation (phantom pain) or by infliction of other wounds (wound pain). However, the use of conventional NMDA antagonists, such as, MK801 or CGS 19755, in preventing or treating chronic pain is severely limited by the adverse PCP-like behavioral side effects that are caused by these drugs. It is expected that the glycine receptor antagonists that are the subject of this invention will be highly effective in preventing chronic pain in mice induced by injecting formalin subcutaneously into the hindpaw of the animals. Because the glycine/excitatory amino acid antagonists of this invention are expected to be free of PCP-like side effects, these drugs are highly useful in preventing or treating chronic pain without causing PCP-like adverse behavioral side effects The effects of the glycine receptor antagonists of the present invention on chronic pain can be evaluated as follows. Male Swiss/Webster mice weighing 25–35 grams are housed five to a cage with free access to food and water and are maintained on a 12 hour light cycle (light onset at 0800 h). The glycine receptor antagonist is dissolved in DMSO at a concentration of 1–40 and 5–40 mg/mL, respectively. DMSO is used as vehicle control. All drugs are injected intraperitoneally (1 µl/g). The formalin test is performed as described (Dubuisson and Dennis, Pain 4:H161–174 (1977)). Mice are observed in a plexiglass cylinder, 25 cm in diameter and 30 cm in height. The plantar surface of one hindpaw is injected subcutaneously with 20 µl of 5% formalin. The degree of pain is determined by measuring the amount of time the animal spends licking the formalin-injected paw during the following time intervals: 0–5' (early phase); 5'–10', 10'–15', and 15'–50' (late phase). To test whether the glycine/excitatory amino acid antagonists prevent chronic pain in the test animals, vehicle (DMSO) or drugs dissolved in vehicle at doses of 1 mg/kg to 40 mg/kg are injected intraperitoneally 30 minutes prior to the formalin injection. For each dose of drug or vehicle control, at least six animals are used.

Compared to vehicle control, it is expected that the intraperitoneal injection of the glycine receptor antagonists 30 minutes prior to formalin injection into the hindpaw will significantly inhibit formalin-induced chronic pain in a dose-dependent manner as determined by the reduction of the time spent licking by the mouse of the formalin injected hindpaw caused by increasing doses of glycine/excitatory amino acid antagonist.

Compositions within the scope of this invention include all compositions wherein the compounds of the present invention are contained in an amount that is effective to achieve its intended purpose. While individual needs vary, determination of optimal ranges of effective amounts of each component is with the skill of the art. Typically, the compounds may be administered to mammals, e.g., humans, orally at a dose of 0.0025 to 50 mg/kg, or an equivalent amount of the pharmaceutically acceptable salt thereof, per day of the body weight of the mammal being treated for anxiety disorders, e.g., generalized anxiety disorder, phobic disorders, obsessional compulsive disorder, panic disorder, and post traumatic stress disorders. Preferably, about 0.01 to about 10 mg/kg is orally administered to treat or prevent such disorders. For intramuscular injection, the dose is generally about one-half of the oral dose. For example, for treatment or prevention of anxiety, a suitable intramuscular dose would be about 0.0025 to about 15 mg/kg, and most preferably, from about 0.01 to about 10 mg/kg.

In the method of treatment or prevention of neuronal loss in ischemia, brain and spinal cord trauma, hypoxia, hypoglycemia, and surgery, as well as for the treatment of Alzheimer's disease, amyotrophic lateral sclerosis, Huntington's disease, and Down's Syndrome, in a method of treating or preventing opiate tolerance, or in a method of treating a disease in which the pathophysiology of the disorder involves hyperactivity of the excitatory amino acids or NMDA receptor-ion channel related neurotoxicity or psychosis, the pharmaceutical compositions of the invention can comprise the compounds of the present invention at a unit dose level of about 0.01 to about 50 mg/kg of body weight, or an equivalent amount of the pharmaceutically acceptable salt thereof, on a regimen of 1–4 times per day. When used to treat chronic pain or to induce anesthesia, the compounds of the invention can be administered at a unit dosage level of from about 0.01 to about 50 mg/kg of body weight, or an equivalent amount of the pharmaceutically acceptable salt thereof, on a regimen of 1–4 times per day. Of course, it is understood that the exact treatment level will depend upon the case history of the animal, e.g., human being, that is treated. The precise treatment level can be determined by one of ordinary skill in the art without undue experimentation.

The unit oral dose can comprise from about 0.01 to about 50 mg, preferably about 0.1 to about 10 mg of the compound. The unit dose can be administered one or more times daily as one or more tablets each containing from about 0.1 to about 10, conveniently about 0.25 to 50, mg of the compound or its solvates.

In addition to administering the compound as a raw chemical, the compounds of the invention can be administered as part of a pharmaceutical preparation containing suitable pharmaceutically acceptable carriers comprising excipients and auxiliaries that facilitate processing of the compounds into preparations that can be used pharmaceutically. Preferably, the preparations, particularly those preparations that can be administered orally and that can be used for the preferred type of administration, such as, tablets, dragees, and capsules, and preparations that can be administered rectally, such as, suppositories, as well as suitable solutions for administration by injection or orally, contain from about 0.01 to 99 percent, preferably from about 0.25 to 75 percent, of active compound(s), together with the excipient.

Also included within the scope of the present invention are the non-toxic pharmaceutically acceptable salts of the compounds of the present invention. Basic salts are formed by mixing a solution of a particular compound of the present invention with a solution of a pharmaceutically acceptable non-toxic base, such as, sodium hydroxide, potassium hydroxide, sodium bicarbonate, sodium carbonate, or an amino compound, such as, choline hydroxide, Tris, bis-Tris, N-methylglucamine, arginine, and the like. See, U.S. application Ser. No. 08/148,268 U.S. Pat. No. 5,514,680, supra.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

When the compositions of the invention are administered ocularly, one may achieve either local or systemic administration. For example, the compositions of the present invention can be administered in the form of eye drops that are substantially isotonic with tear fluid to achieve systemic administration. Preferably, such compositions will also comprise a permeation-enhancing agent, which aids the systemic absorption of the compounds of the present invention. See, U.S. Pat. No. 5,182,258. Alternatively, the compositions of the invention can be administered ocularly to treat or prevent optic nerve degeneration. In this embodiment, the compounds of the present invention are administered in the form of eye drops, as disclosed above, or can be injected into the vicinity of the optic nerve. In the alternative, thin ocular implants can be employed, which slowly release the compounds of the present invention.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically. The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Possible pharmaceutical preparations that can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules, which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. Especially preferred alkaline salts are ammonium salts prepared, for example, with tris, choline hydroxide, bis-tris propane, N-methylglucamine, or arginine. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

The characterization of glycine binding sites in vitro has been difficult because of the lack of selective drug ligands. Thus, the glycine ligands of the present invention can be used to characterize the glycine binding site. Particularly preferred substituted and unsubstituted compounds that can be used for this purpose are isotopically or radiolabelled derivatives, e.g., where one or more of the atoms are replaced with $^2H$, $^3H$, $^{11}C$, $^{14}C$, $^{15}N$, or $^{18}F$.

The following examples are illustrative, but not limiting, of the method and compositions of the present invention. Other suitable modifications and adaptations of the variety of conditions and parameters normally encountered in clinical therapy and obvious to those skilled in the art are within the spirit and scope of the invention.

EXAMPLES

Example 1

Preparation of 5-Aza-7-chloro-4-hydroxy-3-(m-methoxy-phenyl)quinolin-2-one (109)

2-Amino-5-chloro-3-nitropyridine (102)

Concentrated $H_2SO_4$ (97%, 300 mL) was placed in a 500 mL three-neck round-bottom flask. The flask was equipped with an internal thermometer, a glass funnel and stopper, and placed in a salt/ice bath. When the internal temperature reached 5° C., 2-amino-5-chloropyridine (101) (77.2 g, 0.600 mol) was added over 1 h with stirring. The suspension was then stirred at room temperature to dissolve the rest of the solid. The resulting solution was heated to 55° C. $HNO_3$ (70%, 40.5 mL, d=1.41, 0.634 mol) was added dropwise through an addition funnel as to maintain the internal temperature at 57°±3° C. The reaction solution was poured over ice (1.5 kg), and the resulting mixture partially neutralized with 40% NaOH (~600 mL). The mixture was filtered to leave a yellow/orange solid. This solid was washed by resuspension in water (600 mL). The mixture was filtered, and the resulting solid was dried in the oven for 48 h to yield the title compound as an orange/yellow solid (66.3 g, 63.8%), mp 184°–6° C. (Lit., 190°–3° C., Vaughan et al., *J. Amer. Chem. Soc.* 71:1885 (1949)); ¹H NMR (CDCl₃): δ6.69 (bs, 2H), 8.33 (d, J=1.5 Hz, 1H), 8.43 (d, J=1.5 Hz, 1H).

2-Bromo-5-chloro-3-nitropyridine (103)

To a stirred, ice bath cooled solution of HBr (48%, 214 mL, d=1.49, 1.89 mol) was added 2-amino-5-chloro-3-nitropyridine (2) (66.0 g, 376 mmol). The mixture was stirred until the internal temperature was less than 0° C., and then bromine (65 mL, d=3.102, 1.3 mol) was added dropwise. The resulting orange mixture was stirred at a temperature below 0° C. A solution of NaNO₂ (91.3 g, 1.32 mol, used as received) in water (125 mL) was added slowly to the mixture so as to maintain the internal temperature below 0° C. The mixture was stirred for an additional 45 min at below 0° C., and then NaOH (139.3 g, 3.482 mol) in water (200 mL) was slowly added to the mixture to maintain the internal temperature below 20° C. The mixture was stirred at below 20° C. for an additional hour, and then gravity filtered. The recovered brown solid was dried at 25° C. under vacuum for 6 h. It was purified by recrystalization from 95% ethanol to obtain 103 as a yellow solid (46.0 g, 51.5%), mp 68°–73° C. (Lit., 75° C., Berrie et al., *J. Chem. Soc.* 2042 (1952)); ¹H NMR (CDCl₃): δ8.15 (d, J=2.1 Hz, 1H), 8,57 (d, J=2.1 Hz, 1H).

5-Chloro-3-nitropicolinonitrile (104)

2-Bromo-5-chloro-3-nitropyridine (103) (6.0 g, 25 mmol) was mixed with copper (I) cyanide (4.6 g, 51 mmol) in a 100 mL round-bottom flask having a condensor loosely plugged with cotton was attached. The flask was slowly heated in an oil bath. When the temperature reaches approximately 150° C. (takes 2 h), the reaction mass begins to turn black. When the reaction mass turned completely black, the pressure was reduced to approximately 1 mm Hg by vacuum and the oil bath removed after 30 sec. (If the reaction goes too long, a vigorous reaction ensues, leaving little recoverable product.) The mixture was cooled to room temperature, and the sublimed solid (on the cotton) and reaction mass were treated with hot acetone (100 mL). The resulting mixture was gravity filtered, and the mother liquor rota-evaporated to dryness to yield the crude title compound as a dark brown solid. This solid can be purified by column chromatography using 4:1 hexane-EtOAc (R_f=0.13). Purified 104 was obtained in 60% yield overall, mp 93°–5° C. (Lit., 75° C., Berrie, et al., *J. Amer. Chem. Soc.*:2042 (1952)); ¹H NMR (CDCl₃): δ8.62 (d, J=1.5 Hz, 1H), 8.95 (d, J=1.5 Hz, 1H).

3-Amino-5-chloropicolinamide (105)

Raney Nickel (10 g of Aldrich 50% slurry in water) was washed with water (100 mL), 5% AcOH (100 mL), water (100 mL), and 95% EtOH (3×100 mL). The resulting slurry was added to a solution of 5-chloro-3-nitropicolinonitrile (104) (5.0 g, 27 mmol) in 95% EtOH (100 mL). The mixture was hydrogenated at 45 psi for 2.5 h. The mixture was then filtered over a bed of Celite and washed with 95% EtOH (2×100 mL). The red/brown filtrate was rota-evaporated to dryness, leaving the title compound as a light brown solid, 3.8 g (82%), mp 152°–6° C. (Lit., 165°–6° C., McCaustland and Cheng, *J. Heterocycl. Chem.* 7:467 (1970)); ¹H NMR (CDCl₃): δ5.42 (bs, 1H), 6.05 (bs, 2H), 7.00 (d, J=1.2 Hz, 1H), 7.71 (bs, 1H), 7.79 (d, J=1.2 Hz, 1H).

3-Amino-5-chloropicolinic acid (106)

Conc. HCl (38%, 32 mL, d=1.20, 400 mmol) was added to 3-amino-5-chloropicolinamide (105) (2.3 g, 13 mmol). The mixture was stirred and heated to reflux. The resulting solution was refluxed (100° C.) for 17 h. The resulting mixture was cooled to room temperature, then placed in the cold room for 3 h. The mixture was filtered, leaving the title compound as its hydrochloride salt, 2.1 g (66%); mp 235°–236° C. ¹H NMR (DMSO-d₆): δ6.68 (bs, 2H), 7.33 (d, J=1.8 Hz, 1H), 7.80 (d, J=2.1, 1H).

Ethyl 3-amino-5-chloropicolinate (107)

Absolute EtOH (1.00 mL, d=0.785, 17.0 mmol) and H₂SO₄ (96%, 0.10 mL, d=1.840, 1.8 mmol) were added to the hydrochloride salt of 3-amino-5-chloropicolinic acid (106) (0.100 g, 0.407 mmol). The mixture was stirred and heated to reflux. The mixture was refluxed (120° C.) for 19 h. The resulting solution was cooled to room temperature, poured over ice (1.0 g), and neutralized to pH 5 with solid Na₂CO₃. The resulting mixture was extracted with EtOAc (4×3 mL), the organic layer dried (Na₂SO₄), and rota-evaporated to dryness, leaving the title compound as an orange solid, 68.6 mg (84.0%), mp 139.5°–142.5° C. (Lit., 165°–6° C., McCaustland and Cheng, *J. Heterocycl. Chem.* 7:467 (1970)); ¹H NMR (CDCl₃): δ1.44 (t, J=6.9 Hz, 3H), 4.45 (q, J=6.9 Hz, 3H), 5.84 (bs, 2H), 7.05 (d, J=1.5 Hz, 1H), 7.99 (d, J=1.8 Hz, 1H).

Ethyl 5-chloro-3-(m-methoxyphenylacetamido)nicotinate (108)

To a solution of ethyl 3-amino-5-chloropicolinate (107) (0.401 g, 2.0 mmol) in 10 mL of 1,2-dichloroethane and 0.51 mL of triethylamine was added m-methoxyphenylacetic acid chloride (1.25 mL, 8.0 mmol). The resulting solution was allowed to reflux for 12 hr. After cooled to room temperature, the solvent was evaporated in vacuo to dryness. Water (15 mL) was added to the residue and the mixture was extracted with ethyl acetate (3×15 mL). The combined extracts were washed with brine and dried over sodium sulfate. The solvent was evaporated in vacuo and the title compound was obtained by flash chromatography to give 0.7 g (100%) of 108.¹H NMR (CDCl₃): δ1.424 (t, J=7.2 Hz, 3H), 3.802 (s, 3H), 3.812 (s, 2H), 4.420 (q, J=7.2 Hz, 2H), 6.846 (m, 3H), 7.303 (s, 1H), 8.339 (s, 1H), 9.211 (d, J=1.2 Hz, 1H), 11.080 (s, 1H).

5-Aza-7-chloro-4-hydroxy-3-(m-methoxyphenyl)quinolin-2-one (109)

To a solution of KHDMS in toluene (12 mL, 6 mmol) was added dropwise a solution of compound 108 (0.202 g, 0.58 mmol) in 5 mL of THF at −78° C. under N₂. The resulting mixture was allowed to warm to room temperature and stirred at room temperature for additional 12 hr. Water (10 mL) was added to the reaction mixture and extracted with ethyl acetate (5 mL) and the water phase was acidified with 4N HCl to pH 2. The white solid was obtained by filtration and dried to give 100 mg (57%) of the product as a white solid. mp 256°–258° C. ¹H NMR (DMSO-d₆): δ3.717 (s, 3H), 6.837 (d, J=7.2 Hz, 1H), 6.953 (m, 2H), 7.258 (m, 1H), 7.685 (d, J=1.2 Hz, 1H), 8.463 (s, 1H), 10.80 (brs, 1H), 11.657 (s, 1H). EIMS m/e 302 (100, M⁺). HRMS Calcd for C₁₅H₁₁ClN₂O3: 302.0460. Found: 302.0459. (HPLC purity >96%).

Example 2

Preparation of 5-Aza-7-chloro-4-hydroxy-3-(m-phenoxyphenyl) quinolin-2-one (113)

m-Phenoxyphenylacetic acid chloride (111)

To a solution of m-phenoxyphenylacetic acid (110) (1.14 g, 5.0 mmol) in 15 mL of dichloromethane was added 1.27 g (0.87 mL) of oxalyl chloride. The resulting solution was allowed to stir at room temperature for 24 hr. Solvent was evaporated to give an oil (1.233 g, 97%), which was used in next step without purification.

Ethyl 5-chloro-3-(m-phenoxyphenylacetamido)nicotinate (112)

To a solution of ethyl 3-amino-5-chloropicolinate (107) (0.401 g, 2.0 mmol) in 10 mL of 1,2-dichloroethane and 0.35 mL of triethylamine was added m-phenoxyphenylacetic acid chloride (111) (1.233 g, 5.0 mmol). The resulting solution was allowed to reflux for 12 hr. After cooling to room temperature, the solvent was evaporated in vacuo to dryness. Water (15 mL) was added to the residue and the mixture was extracted with ethyl acetate (3×15 mL). The combined extracts were washed with brine and dried over sodium sulfate. The solvent was evaporated in vacuo and the title compound was obtained by flash chromatography to give 0.821 g (100%) of 112. $^1$H NMR (CDCl$_3$): δ1.431 (t, J=7.2 Hz, 3H), 3.762 (s, 2H), 4.423 (q, J=7.2 Hz, 2H), 6.846 (m, 5H), 7.327 (m, 4H), 8.347 (d, J=1.2 Hz, 1H), 9.226 (d, J=1.2 Hz, 1H), 11.076 (s, 1H).

5-Aza-7-chloro-4-hydroxy-3-(m-phenoxyphenyl)quinolin-2-one (113)

To a solution of KHDMS in toluene (4.2 mL, 2.1 mmol) was added dropwise a solution of compound 112 (0.30 g, 0.7 mmol) in 5 mL of THF at −78° C. under N$_2$. The resulting mixture was allowed to warm to room temperature and stirred at room temperature for additional 12 hr. Water (10 mL) was added to the reaction mixture and extracted with ethyl acetate (2×5 mL) and the water phase was acidified with 4N HCl to pH=2. The white solid was obtained by filtration and dried to give 120 mg (47%) of the product as a white solid. mp 246°–248° C. $^1$H NMR (DMSO-d$_6$): δ6.894 (m, 1H), 7.022 (m, 2H), 7.110 (m, 2H), 7.208 (d, J=7.2 Hz, 1H), 7.353 (s, 3H), 7.678 (d, J=1.5 Hz, 1H), 8.462 (d, J=1.5 Hz, 1H), 11.003 (brs, 1H), 11.674 (s, 1H). EIMS m/e 364 (40, M$^+$), 77 (100). HRMS Calcd for C$_{20}$H$_{13}$ClN$_2$O$_3$: 364.0603. Found: 364.0609. (HPLC purity >99%).

Example 3

Preparation of 5-aza-4-hydroxy-3-phenylquinolin-2-one (119)

Quinolinimide (114)

A mixture of quinolinic acid (16.8 g, 101 mmol) and acetic anhydride (22 mL, 233 mmol) was heated at atmospheric pressure in a distillation apparatus with mixing to distill off 19 mL of distillate. The residue was cooled to approximately 100° C. and acetamide (13.4 g, 227 mmol) was added over 5 min. with stirring. The stirred mixture was heated to reflux and refluxed for 2.5 h. The mixture was allowed to cool to room temperature, filtered, and the filter cake washed with water (2×25 mL) to obtain a brown solid. The solid was triturated with water (25 mL) and filtered. The filter cake was washed with water (2×25 mL), and dried to obtain a brown solid (9.4 g, 63%); mp 228°–229.5° C. The solid was treated with hot ethanol (95%, 50 mL), cooled in an ice bath, and filtered. The filter cake was washed with water (20 mL), and dried to obtain the title compound (114) as a brown solid (8.4 g, 56%); mp 230°–231° C. (Lit., 230°–233° C., Crum and Fuchsman, *J. Heterocycl. Chem.* 3:252–256 (1966)). IR (KBr) 3484, 3189, 3100, 3083, 1735, 1704, 1086, 736. $^1$H NMR (DMSO-d$_6$): δ7.76 (dd, J$_1$=2.4, J$_2$=5.1, 1, H-5), 8.24 (dd, J$_1$=0.9, J$_2$=7.2, 1, H-4), 8.96 (dd, J$_1$=0.9, J$_2$=7.5, 1, H-6), 11.66 (bs, 1, NH).

3-Aminopicolinic acid (115)

Quinolinimide (114) (8.0 g, 54 mmol) was dissolved in an ice-cold 10% NaOH solution (160 mL) in a 250 mL round-bottom flask with stirring. Ice-cold aqueous sodium hypobromite [prepared by adding bromine (3.0 mL, 9.3 g, 58 mmol) to an ice-cold 15% NaOH solution (56 mL)] was added to the above solution over 10 min. The brown solution was stirred at room temperature for 1 h and then at 85° C. (oil bath) for 1 h. The solution was then cooled to room temperature and the pH adjusted to 5 using sulfuric acid. The solution was stirred at 4° C. for 63 h. The resulting mixture was filtered and the mother liquor was treated with copper (II) acetate-monohydrate (3.2 g, 16 mmol) in hot water (64 mL) containing glacial acetic acid (1.60 mL). The resulting mixture was cooled to room temperature and filtered, and the filter cake washed with water (2×25 mL). The precipitate was resuspended in water (64 mL) and saturated with hydrogen sulfide. The mixture was filtered through a fritted filter to remove the copper sulfide. The filtrate was rota-evaporated to dryness, leaving an orange solid. The orange solid was dissolved in hot water (20 mL), cooled in an ice-bath, filtered and the filter cake dried to yield the title compound (115) as light brown crystals; mp 207.5°–208° C. (Lit., 210° C., Oakes et al., *J. Chem. Soc.*:1045–1054 (1956)). IR (KBr) 3386, 3200, 3133, 1644, 1565, 1532, 1398, 1286, 806. $^1$H NMR (DMSO-d$_6$): δ7.26 (d, J=8.4, 1, H-4), 7.33 (dd, J$_1$=4.2, J$_2$=8.4, 1, H-5), 7.82 (d, J=3.9, 1, H-6). A second crop of crystals was obtained by evaporating the mother liquor and recrystallizing in water (0.62 g, 8.3%); mp 205°–206° C. $^1$H NMR (DMSO-d$_6$): δ7.26 (d, J=8.1, 1, H-4), 7.33 (dd, J$_1$=3.9, J$_2$=8.4, 1, H-5), 7.82 (d, J=4.2, 1, H-6).

Methyl 3-aminopicolinate (116)

3-Aminopicolinic acid (115) (0.585 g, 4.24 mmol) was dissolved in MeOH (absolute, 45 mL). The solution was stirred while an ethereal solution of diazomethane was added until a yellow color persisted (~30 mL). The solution was stirred an additional 30 min, and the solvent rota-evaporated. The resulting residue was dried under reduced pressure at room temperature to yield 0.635 g (98.5%) of crude 116 as a yellow residue. The crude residue was chromatographed on a column of silica (12 g, Mallinckrodt, grade 62, mesh 60–200, used as received) using CHCl$_3$-MeOH [19:1, (180 mL), 7:3 (100 mL), 1:1 (100 mL), 100% MeOH (150 mL)]. After collecting appropriate fractions, rota-evaporating off the solvent and drying under reduced pressure at 25° C., 0.333 g (51.7%) of 116 was obtained as a yellow solid; mp 139°–146° C.; R$_f$=0.54 [CHCl$_3$-MeOH (9:1)]. IR (KBr) 3455, 3295, 3160, 1689, 1617, 1408, 1335, 1244, 1115. $^1$H NMR (CDCl$_3$) δ3.98 (t, J=7.2, 3, CH$_3$O—), 5.73 (d, J=1.8, 2, NH$_2$), 7.05 (dd, J$_1$=1.2, J$_2$=8.4, 1, H-4), 7.22 (dd, J$_1$=4.2, J$_2$=8.4, 1, H-5), 8.07 (dd, J$_1$=1.2, J$_2$=4.2, 1, H-6).

Methyl 3-(phenylacetamido)picolinate (118)

Dry CH$_2$Cl$_2$ (20 mL) was added to methyl 3-aminopicolinate (116) (0.421 g, 2.77 mmol). The solution was purged with nitrogen. Triethyl amine (1.16 mL, d=0.726, 8.31 mmol) was added to the solution via syringe. Phenylacetyl chloride (117) (0.805 mL, d=1.169, 6.09 mmol) was added to the solution via syringe. The mixture was stirred overnight at room temperature under nitrogen. The mixture was then stirred at 40° C. for 6 h. More triethyl amine (0.50 mL, 3.6 mmol) was added and, an hour later, more phenylacetyl chloride (0.400 mL, 3.02 mmol) was added. The mixture was stirred an additional hour and allowed to cool to room temperature. The reaction was quenched with water (20 mL), and the aqueous layer removed. The organic layer washed with water (3×15 mL), and dried with MgSO$_4$. Silica gel was added and the slurry rota-evaporated to dryness. The resulting silica was chromatographed on silica (40 g, Davisil, grade 643, mesh 200–450) and eluded with EtOAc-hexanes (2:1, 400 mL). The appropriate fractions were collected (R$_f$=0.35). The solvent was rota-evaporated to yield the title compound (118) as a yellow oil, which, upon drying, precipitated out as a yellow solid (0.4463 g, 59.6%); R$_f$=0.35. $^1$H NMR (CDCl$_3$) δ3.78 (s, 2, benzyllic), 3.97 (s, 3, CH$_3$O—), 7.38

(m, 6, phenyl & H-5), 8.39, (dd, $J_1$=0.6, $J_2$=3.9, 1, H-4), 9.10 (dd, $J_1$=8.4, $J_2$=8.3, 1, H-6), 10.96 (s, 1, NH); MS (m./z) 270 (M$^+$, 35), 211 (35), 179 (85), 153 (40), 147 (65), 119 (40), 94, (40), 91 (100).

5-Aza-4-hydroxy-3-phenylquinolin-2-one (119)

Methyl 3-(phenylacetamido)picolinate (118) (78.5 mg, 0.290 mmol) was placed in a 10 mL round-bottom flask. The system was purged with nitrogen. Dry THF (5 mL) was added to the flask via syringe. The solution was chilled to −70° C. (acetone/dry ice). KHMDS (0.600 mL of 0.5M solution in toluene) was added dropwise to the cold solution via syringe. The resulting mixture was allowed to warm to room temperature by leaving the flask in the evaporating cooling bath. More KHMDS (0.600 mL of 0.5M solution in toluene) was added via syringe. The mixture was allowed to stir under nitrogen at room temperature overnight. The reaction mixture was filtered to obtain a white-yellow solid. The solid was dissolved in water (6 mL). The solution was neutralized to pH 6 with 0.1N HCl. The mixture was extracted twice with EtOAc (7 mL). The organic layer now contained the white suspension. The solvent was removed by rota-evaporation, leaving the title compound (119) as a brown solid (0.0367 g, 53%); mp 254°–258° C. IR (KBr) 3427, 3161, 2923, 2854, 1655, 1477, 1402, 1123, 693. $^1$H NMR (DMSO-d$_6$): δ7.29 (d, J=7.2, 1, phenyl), 7.37 (t, J=7.2, 2, phenyl), 7.45 (d, J=7.5, 2, phenyl), 7.60 (dd, $J_1$=4.2, $J_2$=8.1, 1, H-7), 7.69 (d, J=8.1, 1, H-8), 8.49 (d, J=4.2, 1, H-6), 11.62 (s, 1, NH). MS (m./z) 238 (M$^+$, 100), 210 (10), 181 (15), 93 (20), 89 (15), 78 (15), 63 (15), 51 (10), 39 (25).

Example 4

Preparation of 8-Aza-4-hydroxy-3-phenylquinolin-2-one (122)

Ethyl 2-aminonicotinate (121)

Absolute ethanol (10 mL) was added to 2-aminonicotinic acid (120, commercially available) (3.9 g, 28 mmol). To the resulting stirred mixture was added H$_2$SO$_4$ (96%, 5 mL). The mixture was heated and refluxed at 120° C. for ~4 h. The suspension was cooled to room temperature, poured over ice (30 g), and neutralized to pH 5 using solid Na$_2$CO$_3$. The aqueous suspension was extracted with EtOAc (3×25 mL). These combined organic extracts were washed with water (3×30 mL), dried (Na$_2$SO$_4$), and rota-evaporated to dryness, leaving the title compound as off-white crystals (2.8 g, 60%); mp 90.5°–92.5° C. (Lit., 94°–95° C., Hirai, E., *Chem. Pharm. Bull.* 14:861 (1966)). $^1$H NMR (CDCl$_3$): δ1.38 (t, J=7.2, 3, CH$_3$CH$_2$), 4.34 (q, J=7.2, 2, CH$_3$CH$_2$O), 6.40 (bm, 2, NH$_2$), 6.62 (dd, $J_1$=4.9, $J_2$=7.8, 1, H-4), 8.14 (dd, $J_1$=1.0, $J_2$=8.4, 1, H-5), 8.21 (dd, $J_1$=1.2, $J_2$=3.8, 1, H-6).

8-Aza-4-hydroxy-3-phenylquinolin-2-one (122)

To a stirred solution of freshly prepared sodium ethoxide (0.0403 g of Na and 4 mL of absolute EtOH) under nitrogen was added ethyl 2-aminonicotinate (122) (103.0 mg, 0.6280 mmol). To this solution was added ethyl phenylacetate (0.25 mL, d=1.031, 1.6 mmol). The suspension was stirred, heated to 95° C. (oil bath, external), and refluxed for approximately 22 h. The mixture was cooled to room temperature and centrifuged (5 min) to separate a white solid and yellow mother liquor. The mother liquor was removed by pipet, and solid dissolved in water (2 mL). Glacial acetic acid (2 drops) was added to form a white precipitate. The mixture was centrifuged (5 min) to separate a white solid and clear mother liquor. The mother liquor was removed by pipet, and the solid product removed and dried in an oven (43° C., 1.5 h). The title compound was obtained as a white powder, 123.4 mg (82.5%), mp 340°–342° C. $^1$H NMR (DMSO-d$_6$): δ7.17 (dd, $J_1$=4.8, $J_2$=7.8, 1, H-6), 7.25 (m, 1, H-4'), 7.34 (t, J=7.2, 2, H-3' & H-5'), 7.42 (dd, $J_1$=0.9, $J_2$=7.2, 2, H-2' & H-6'), 8.29 (dd, $J_1$=1.2, $J_2$=7.8, H-5), 8.45 (dd, $J_1$=1.2, $J_2$=7.8, H-7), 11.64 (s, 1, —NH); HPLC 99.2%; LRMS (m/z) 239 (M$^+$. 100), 238 (90), 181 (20), 121 (40), 118 (20), 93 (40), 91 (55), 89 (15), 77 (25) 69 (20), 63 (25), 57 (35), 55 (40), 51 (30), 43 (55), 41 (55); HRMS Calcd: 238.0742. Found: 238.0737.

Example 5

Preparation of 6,7-Dichloro-1,2-dihydroquinoxalin-2-one-4-oxide (124)

N-(Benzoylacetyl)-4,5-dichloro-2-nitroaniline (123)

A mixture of 4,5-dichloro-2-nitroaniline (2.07 g, 10 mmol) and ethyl benzoylacetate (technical, 5 mL, approximately 22 mmol) was heated at 180° C. for 16 h under stirring. It was cooled to 150° C. and kept at this temperature under aspirator vacuum for 5 h, then cooled to room temperature. Chloroform (50 mL) was added and the mixture was evaporated, then diluted with ether (200 mL) and cooled to −10° C. Precipitate was filtered and washed with ether (5×50 mL) to give 2.12 g (60%) of the title compound as an orange solid: mp 177°–179° C. (from EtOH); IR (KBr) 3330, 1693, 1670, 1561, 1472, 1340, 1233, and 764 cm$^{-1}$; $^1$H NMR (DMSO-d$_6$) δ4.24 (s, 2H), 7.53 (m, 2H), 7.65 (m, 1H), 7.77 (d, 1H, J=7.6 Hz), 7.97 (d, 1H, J=7.6 Hz), 8.11 (s, 1H), 8.23 (s, 1H), 10.70 (s, 1H, N—H). HRMS Calcd for $C_{15}H_{10}N_2O_4Cl_2$: 352.0018. Found: 352.0020.

6,7-Dichloro-1,2-dihydroquinoxaline-2-one-4-oxide (124)

A suspension of the N-(benzoylacetyl)-4,5-dichloro-2-nitroaniline (0.351 g, 1 mmol) in 20% NaOH (5 mL) was refluxed under stirring for 1 h. The mixture was cooled to room temperature and acidified with 2N HCl to pH 2 to form a precipitate. The precipitated product was filtered, washed with 2N HCl (3×20 mL), H$_2$O (5×20 mL), ethanol (20 mL), and ether (20 mL), and then air dried to give 0.207 g (90%) of the title compound as a light brown powder: mp 278°–280° C. (H$_2$O from DMSO); IR (KBr) 3450, 3104, 2934, 1693, 1593, 1517, 1412, 1270, and 890 cm$^{-1}$; $^1$H NMR (DMSO-d$_6$) δ7.50 (s, 1H), 7.95 (s, 1H), 8.23 (s, 1H), 12.45 (br.s, 1H, N—H); $^{13}$C NMR (DMSO-d$_6$) δ118.09, 121.32, 125.79, 129.75, 130.31, 133.25, 135.50, 157.30; HPLC: 98.1%. HRMS Calcd for $C_8H_4N_2O_2Cl_2$: 229.9650. Found: 229.9660.

Example 6

Preparation of 6,7-Dichloro-3-phenyl-1,2-dihydroquinoxalin-2-one-4-oxide (126)

4,5-Dichloro-2-nitro-1-(phenylacetamido)benzene (125)

A mixture of phenylacetic acid (10 mmol) in SOCl$_2$ (4 ml, apr. 50 mmol) was stirred for 16 h at room temperature, then evaporated and kept at 2 mm Hg for 0.5 h to remove residual SOCl$_2$. A suspension of 4,5-dichloro-2-nitroaniline (1.035 g, 5 mmol) in ethanol-free CHCl$_3$ (10 mL) was added to the residue and the mixture was stirred at 50° C. for 4 h. It was then cooled to room temperature and evaporated. The residue was treated with ether (100 mL). Precipitated crude product was filtered, washed with ether (5×20 mL) and dried on air to give the title compound. Yield 90%; mp 116°–118° C. (from EtOH); (Lit., 118° C., Ahmad, Yu., et al., *Tetrahedron* 21:861 (1965)).

6,7-Dichloro-3-phenyl-1,2-dihydroquinoxalin-2-one-4-oxide (126)

To a stirred solution of 125 (8 mmol) in pyridine (15 mL), 20% aqueous NaOH (40 mL) was added. The resulting mixture was refluxed for 1 h, then cooled to room temperature, diluted with water (50 mL), and acidified with concentrated HCl to pH 2. The precipitated crude product was filtered, washed with 2N HCl, and then water, and air dried to give phenylnitrones 407. Yield: 72%; mp 300°–302° C. (from EtOAc); (Lit., 305°–306° C., Ahmad, Yu., et al., *Tetrahedron* 21:861 (1965)); IR (KBr) 3207, 3158, 3067, 2926, 2856, 1696, 1682, 1618, 1364, 1356 and 1250 cm$^{-1}$; $^1$H NMR (in DMSO-d$_6$) δ7.44 (m, 3H), 7.51 (s, 1H), 7.65 (m, 2H), 8.28 (s, 1H), 12.59 (s, 1H, N—H); HPLC: 100%.

Example 7

Preparation of 6,7-Dichloro-3-(4'-methoxyphenyl)-1,2-dihydroquinoxalin-2-one-4-oxide (128)

4,5-Dichloro-2-nitro-1-[(4-methoxyphenyl)acetamido]benzene (127)

The title compound was prepared according to the procedure described in the preceding example by substituting 10 mmol of p-methoxyphenylacetic acid for phenylacetic acid. Yield 95%; mp 124°–126° (from EtOH); IR KBr 3318, 3124, 2933, 2840, 1708, 1607, 1569, 1512, 1473, 1385, 1337, 1305, 1277, 1250, 1227 and 1033 cm$^{-1}$; $^1$H NMR (DMSO-d$_6$) δ3.62 (s, 2H), 3.70 (s, 3H), 6.87 (d, 2H, J=8.4 Hz), 7.19 (d, 2H, J=8.4 Hz), 8.05 (s, 1H), 8.26 (s, 1H), 10.44 (br. s, 1H, N—H); HRMS Calcd for C$_{15}$H$_{12}$N$_2$O$_4$Cl$_2$: 354.0174.

6,7-Dichloro-3-(4'-methoxyphenyl)-1,2-dihydroquinoxalin-2-one-4-oxide (128)

The title compound was prepared according to the procedure described in the preceding example by substituting 127 (8 mmol) for 125. Yield: 75%; mp 262°–264° C. (from EtOH); IR (KBr) 3439, 3204, 2934, 2841, 1696, 1682, 1663, 1609, 1362, 1308, 1262 and 1184 cm$^{-1}$; $^1$H NMR (in DMSO-d$_6$) δ3.79 (s, 3H), 6.99 (d, 2H, J=8.7 Hz), 7.50 (s, 1H), 7.74 (d, 2H, J=8.7 Hz), 8.28 (s, 1H), 12.48 (br.s, 1H, N—H); HPLC: 97%; HRMS Calcd for C$_{15}$H$_{10}$N$_2$O$_3$Cl$_2$: 336.0068. Found: 336.0068.

Example 8

Preparation of 6,7-Dichloro-3-(3'-methoxyphenyl)-1,2-dihydroquinoxalin-2-one-4-oxide (130)

4,5-Dichloro-2-nitro-1-[(3-methoxyphenyl)acetamido]benzene (129)

The title compound was prepared according to the procedure described in Example 6 by substituting 10 mmol of m-methoxyphenylacetic acid for phenylacetic acid. Yield 91%; mp 122°–124° C. (from EtOH). IR KBr 3320, 3121, 2935, 2843, 1702, 1601, 1563, 1509, 1390, 1252 and 1231 cm$^{-1}$; $^1$H NMR (DMSO-d$_6$) δ3.38 (s, 2H), 3.65 (s, 3H), 7.08 (m, 3H), 7.19 (m, 1H), 8.05 (s, 1H), 8.25 (s, 1H), 10.49 (br.s, 1H, N—H); HRMS Calcd for C$_{15}$H$_{12}$N$_2$O$_4$Cl$_2$: 354.0174.

6,7-Dichloro-3-(3'-methoxyphenyl)-1,2-dihydroquinoxalin-2-one-4-oxide (130)

The title compound was prepared according to the general procedure described in Example 6 by substituting 8 mmol of 129 for 125. Yield: 91%; mp 238°–240° C. (from EtOH); IR (KBr) 3436, 3046, 2926, 2855, 1652, 1618, 1597, 1374, 1363 and 1263 cm$^{-1}$; $^1$H NMR (in DMSO-d$_6$) δ3.73 (s, 3H), 7.00 (m, 1H), 7.18 (m, 2H), 7.20 (s, 1H), 7.36 (m, 1H), 7.52 (s, 1H), 8.28 (s, 1H), 12.57 (br.s, 1H, N—H); HPLC: 100%; HRMS Calcd for C$_{15}$H$_{10}$N$_2$O$_3$Cl$_2$: 336.0068. Found: 336.0075.

Example 9

Preparation of 6,7-Dichloro-3-(2'-methoxyphenyl)-1,2-dihydroquinoxalin-2-one-4-oxide (132)

4,5-Dichloro-2-nitro-1-[(2-methoxyphenyl)acetamido]benzene (131)

The title compound was prepared according to the procedure described in Example 6 by substituting 10 mmol of o-methoxyphenylacetic acid for phenylacetic acid. Yield 72%; mp 123°–125° C. (from EtOH); IR KBr 3301, 3114, 3071, 2950, 2848, 1705, 1604, 1571, 1541, 1475, 1339, 1250 and 1134 cm$^{-1}$; $^1$H NMR (DMSO-d$_6$) δ3.69 (s, 2H), 3.77 (s, 3H), 6.96 (m, 2H), 8.24 (s, 1H), 8.30 (s, 1H), 10.39 (br.s, 1H, N—H); HRMS Calcd for C$_{15}$H$_{12}$N$_2$O$_4$Cl$_2$: 354.0174.

6,7-Dichloro-3-(2'-methoxyphenyl)-1,2-dihydroquinoxalin-2-one-4-oxide (132)

The title compound was prepared according to the general procedure described in Example 6 by substituting 8 mmol of 131 for 125. Yield: 50%; mp 239°–241° C. (from EtOH); IR (KBr) 3459, 3050, 2958, 2796, 1651, 1618, 1375 and 1257 cm$^{-1}$; $^1$H NMR (in DMSO-d$_6$) δ3.69 (s, 3H), 7.00 (dd, 1H, JJ=7.4 Hz), 7.10 (d, 1H, J=7.4 Hz), 7.26 (d, 1H, J=7.4 Hz), 7.46 (dd, 1H, JJ=7.4 Hz), 7.54 (s, 1H), 8.26 (s, 1H), 12.58 (br.s, 1H, N—H); HPLC: 98%; HRMS Calcd for C$_{15}$H$_{10}$N$_2$O$_3$Cl$_2$: 336.0068. Found: 336.0078.

Example 10

Preparation of 6,7-Dichloro-3-(3'-methylphenyl)-1,2-dihydroquinoxalin-2-one-4-oxide (134)

4,5-Dichloro-2-nitro-1-[(3-methylphenyl)acetamido]benzene (133)

The title compound was prepared according to the procedure described in Example 6 by substituting 10 mmol of m-tolylacetic acid for phenylacetic acid. Yield 52%; mp 122°–124° C. (from EtOH); IR KBr 3296, 3112, 2929, 2856, 1691, 1567, 1481, 1336, 1280, 1239 and 1157 cm$^{-1}$; $^1$H NMR (DMSO-d$_6$) δ2.23 (s, 3H), 3.63 (s, 2H), 7.05 (m, 2H), 7.07 (s, 1H), 7.16 (m, 1H), 8.02 (s, 1H), 8.23 (s, 1H), 10.46 (br.s, 1H, N—H); HRMS Calcd for C$_{15}$H$_{12}$N$_2$O$_3$Cl$_2$: 338.0225. Found: 338.0221.

6,7-Dichloro-3-(3'-methylphenyl)-1,2-dihydroquinoxalin-2-one-4-oxide (134)

The title compound was prepared according to the general procedure described in Example 6 by instituting 8 mmol of 133 for 125. Yield: 97%; mp 260°–262° C. (from EtOH); IR (KBr) 3454, 3044, 2923, 2801, 1653, 1617, 1380, 1364, 1311 and 1245 cm$^{-1}$; $^1$H NMR (in DMSO-d$_6$) δ2.31 (s, 3H), 7.23 (m, 1H,), 7.33 (m, 1H), 7.43 (m, 1H), 7.44 (s, 1H, 7.51 (s, 1H), 8.27 (s, 1H), 12.59 (br.s, 1H, N—H); HPLC: 97%; HRMS Calcd for C$_{15}$H$_{10}$N$_2$O$_2$Cl$_2$: 320.0119.

Example 11

Preparation of 6,7-Dichloro-3-(3'-phenoxyphenyl)-1,2-dihydroquinoxalin-2-one-4-oxide (136)

4,5-Dichloro-2-nitro-1-[(3-phenoxyphenyl)acetamido]benzene (135)

The title compound was prepared according to the procedure described in Example 6 by substituting 120 mmol of commercially available m-phenoxyphenylacetic acid for phenylacetic acid. Yield 77%; mp 135°–137° C. (from EtOH). IR KBr 3305, 3113, 3092, 2926, 2856, 1696, 1567, 1483, 1470, 1253, 1233 and 1213 cm$^{-1}$; $^1$H NMR (DMSO-d$_6$) δ3.65 (s, 2H), 7.02 (m, 5H), 7.19 (m, 4H), 8.04 (s, 1H), 8.20 (s, 1H), 10.47 (br.s, 1H, N—H); HRMS Calcd for C$_{20}$H$_{14}$N$_2$O$_4$Cl$_2$: 416.0331.

6,7-Dichloro-3-(3'-phenoxyphenyl)-1,2-dihydroquinoxalin-2-one-4-oxide (136)

The title compound was prepared according to the general procedure described in Example 6 by substituting 8 mmol of 135 for 125. Yield: 53%; mp 258°–260° C. (from EtOH); IR (KBr) 3450, 3207, 3180, 3039, 1674, 1617, 1581, 1465, 1361, 1262, 1220 and 1149 cm$^{-1}$; $^1$H NMR (in DMSO-d$_6$) δ7.10 (m, 3H), 7.37 (m, 5H), 7.44 (s, 1H), 7.50 (s, 1H), 8.27

(s, 1H), 12.58 (br.s, 1H, N—H); HPLC: 98%; HRMS Calcd for $C_{20}H_{12}N_2O_3Cl_2$: 398.0225.

Example 12

Preparation of 6,7-Dichloro-3-phenyl-1,2-dihydroquinoxalin-2-one-4-oxide (126)

To a stirred solution of Grignard reagent prepared from Mg (240 mg, 10 mmol) and phenyl bromide (10 mmol) in THF (50 mL) solid powdered nitrone 124 (2 mmol) was added in small portions. The mixture was stirred for 2 h, then decomposed with MeOH (50 mL) and evaporated. The crude hydroxylamine derivative 139 was washed with hexane (3×10 mL), suspended in $CHCl_3$ (100 mL) and stirred with $MnO_2$ for 16 h. Solid inorganic material was filtered off, washed with $CHCl_3$ (10×10 mL), and MeOH (10×10 mL). Combined organic filtrate was evaporated. Solid residue was chromatographed on prep. TLC plate, eluent—mixture $CHCl_3$—MeOH (15:1), to yield of 3-aryl nitrone 126. Yield: 39%; the compound was identical to that prepared in Example 6.

Example 13

Preparation of 6,7-Dichloro-3-(4'-methoxyphenyl)-1,2-dihydroquinoxalin-2-one-4-oxide (128)

The title compound was prepared according to the general procedure described in Example 12, except that p-methoxyphenylmagnesium bromide was substituted for phenylmagnesium bromide. Yield: 22%; the compound was identical to that prepared in Example 7.

Example 14

Preparation of 6,7-Dichloro-3-(3'-methoxyphenyl)-1,2-dihydroquinoxalin-2-one-4-oxide (130)

The title compound was prepared according to the general procedure disclosed in Example 12, except that m-methoxyphenylmagnesium bromide was subtituted for phenylmagnesium bromide. Yield: 20%; compound was identical to that prepared in Example 8.

Example 15

Preparation of 6,7-Dichloro-3-(4'-hydroxyphenyl)-1,2-dihydroquinoxalin-2-one-4-oxide (137)

A mixture of p-methoxyphenyl nitrone 128 (2 mmol) and $BBr_3$ (1M in $CH_2Cl_2$, 15 mL, 15 mmol) in $CH_2Cl_2$ (100 mL) was stirred for 20 h, then evaporated. The residue was evaporated with MeOH (25 mL, repeated twice), then water (50 mL) was added. The reaction mixture was basified with saturated $NaHCO_3$ to pH 8, stirred for 1 h and acidified with 2N HCl to pH 3. The precipitated crude product was filtered, washed with water to a neutral pH, air dried and recrystallized from EtOH to give the title compound. Yield: 71%; mp 276°–278° C. (from EtOH); IR (KBr) 3422, 3069, 1670, 1653, 1609, 1590, 1459, 1361, 1297 and 1226 $cm^{-1}$; $^1$H NMR (in DMSO-$d_6$) δ6.83 (d, 2H, J=8.7 Hz), 7.41 (s, 1H), 7.99 (s, 1H), 8.27 (d, 2H, J=8.7 Hz), 10.09 (br.s, 1H, O—H), 12.53 (br.s, 1H, N—H); HPLC: 98%; HRMS Calcd for $C_{14}H_8N_2O_3Cl_2$: 321.9912.

Example 16

Preparation of 6,7-Dichloro-3-(2'-hydroxyphenyl)-1,2-dihydroquinoxalin-2-one-4-oxide (138)

The title compound was prepared according to the general procedure of Example 15, except that nitrone 133 is substituted for nitrone 128. Yield: 30%; mp 266°–268° C. (from EtOH); IR (KBr) 3440, 3218, 3102, 2929, 1674, 1619, 1470, 1348, 1143 and 1112 $cm^{-1}$; $^1$H NMR (in DMSO-$d_6$) δ6.86 (m, 2H), 7.25 (m, 2H), 7.53 (s, 1H), 8.28 (s, 1H), 9.41 (br.s, 1H, O—H), 12.57 (br.s, 1H, N—H); HPLC: 99%; HRMS Calcd for $C_{14}H_8N_2O_3Cl_2$: 321.9912.

Example 17

Preparation of 3-cyano-6,7-dichloro-1,2-dihydroquinoxaline-2-one-4-oxide (143)

N-(Cyanoacetyl)-4,5-dichloro-2-nitroaniline (142)

To a suspension of cyanoacetic acid (1.70 g, 20 mmol) in $CH_2Cl_2$ (50 mL) oxalyl chloride (2.2 mL, 25 mmol) was added. The mixture was stirred for 2 h, more oxalyl chloride (2.2 mL, 25 mmol) was added and the mixture was refluxed while stirring for 3 h. The mixture was cooled to room temperature and evaporated twice with ethanol-free $CHCl_3$ (20 mL) to remove excess of $(COCl)_2$. To the residue was added 4,5-dichloro-2-nitroaniline (1.035 g, 5 mmol) and $CH_2Cl_2$ (10 mL) and the resulting mixture was stirred for 3 h, then diluted with ether (50 mL). The precipitate was filtered, washed with ether (5×10 mL) to give 0.891 g (65%) of the title compound as an orange solid: mp 156°–158° C. (from EtOH); IR (KBr) 3369, 3118, 2928, 2261, 1694, 1609, 1576, 1498, 1346 and 1280 $cm^{-1}$; 1H NMR (DMSO-$d_6$) δ4.00 (s, 2H), 7.94 (s, 1H), 8.31 (s, 1H), 10.70 (s, 1H, N—H). HRMS Calcd for $C_9H_5N_3O_3Cl_2$: 272.9708. Found: 272.9712.

3-Cyano-6,7-dichloro-1,2-dihydroquinoxaline-2-one-4-oxide (143)

To a stirred solution of 142 (0.552 g, 2 mmol) in pyridine (4 mL), 1N NaOH (4 mL, 4 mmol) was added. The resulting mixture was stirred for 4 h, then diluted with water (50 mL) and acidified with 2N HCl to pH 2. The precipitated crude product was washed with water, dried on a filter and washed with ether (5×5 mL) to give 0.365 g (72%) of the title compound as an orange solid: mp 294°–296° C. (from EtOH); IR (KBr) 3104, 3048, 2231, 1675, 1623, 1453, 1399 and 1176 $cm^{-1}$; $^1$H NMR (DMSO-$d_6$) δ7.54 (s, 1H), 8.25 (s, 1H), 12.20 (s, 1H, N—H). HPLC: 95%; HRMS Calcd for $C_9H_3N_3O_2Cl_2$: 254.9602. Found: 254.9604.

Example 18

Preparation of 8-Aza-6-chloro-4-hydroxy-3-phenylquinolin-2-one (145)

Ethyl 2-Amino-5-chloronicotinate (143)

Ethyl 2-aminonicotinate (121, Example 4) (0.1626 g, 0.9906 mmol) was placed in a 10 mL round-bottom flask. Conc. HCl (35%, 1 mL) was added and the mixture stirred. When all of the ester had dissolved, $H_2O_2$ (30%, 0.10 mL, d=1.110, 0.98 mmol) was added. The resulting solution was heated at 55°–60° C. for 2 h. The solution was cooled to room temperature, diluted with water (10 mL), and basified to pH 8 (pH paper) with solid $NaHCO_3$. The mixture was filtered, washed with water (2×10 mL) and dried at 45° C. for 2 h to leave the title compound as a white solid, 0.186 g (93.7%), mp 119.5°–121.5° C.; $^1$H NMR ($CDCl_3$): δ1.39 (t, J=7.05, 3, $CH_3CH_2$), 4.35 (q, J=7.05, 2, $CH_3CH_2O$), 6.44 (bm, 2, $NH_2$), 8.11 (d, J=2.40, 1, py), 8.16 (d, J=2.4, 1, py); IR (KBr): 3448, 3441, 3284, 3161, 1709, 1641, 1402, 1307, 1232, 1150, 1109, 796; HPLC: 100%; LRMS (m/z) 202 (30), 200 ($M^+$, 100), 172 (15), 156 (20), 155 (30), 154 (60) 130 (15), 129 (20), 128 (50), 127 (45), 126 (15), 100 (15), 92 (10), 73 (20) 65 (15), 64 (15); HRMS Calcd: 200.0352. Found: 200.0355.

Ethyl 5-Chloro-2-(phenylacetamido)nicotinate (144)

Phenylacetyl chloride (0.21 mL, d=1.169, 1.6 mmol) was added to ethyl 2-amino-5-chloronicotinate (143) (159.6 mg, 0.7956 mmol) in a 10 mL round-bottom flask. A stir bar and pyridine (1.0 mL, distilled) were added. The mixture was heated to reflux (130° C., oil bath) with stirring under nitrogen. The resulting solution was refluxed for 1 h, then cooled to room temperature. The reaction mixture was quenched with water (5 mL) and extracted with chloroform (3×10 mL). The combined organic extracts were washed with sat. NaHCO$_3$ (3×10 mL) and water (3×10 mL), dried (MgSO$_4$), and rota-evaporated to dryness, leaving an orange liquid. This liquid was chromatographed on silica gel (30 g, Mallinckrodt, grade 62, mesh 60–200) and eluded with hexanes-EtOAc (1:4, 250 mL). The desired fractions were collected (R$_f$=0.79) and rota-evaporated to dryness, leaving an orange solid. Crystallization from ethanol afforded the title compound as yellow needles, 110 mg (43.6%), mp 113.5°–114° C.; $^1$H NMR (CDCl$_3$): δ1.38 (t, J=7.2, 3, CH$_3$CH$_2$), 3.90 (s, 2, benzylic), 4.34 (q, J=7.2, 2, CH$_3$CH$_2$O), 7.38 (m, 5, phenyl), 8.22 (d, J=2.4, 1, py), 8.54 (d, J=2.4, 1, py), 10.64 (s, 1, NH); IR (KBr): 3427, 3196, 1743, 1640, 1600, 1409, 1272, 1218, 1136, 1096, 796; HPLC: 100%; LRMS: 318 (M$^+$, 25), 202 (20), 201 (10), 200 (60), 183 (15), 181 (40), 154 (10), 128 (10), 118 (100 ), 91 (80), 65 (25), 39 (10); HRMS Calcd: 318.0771. Found: 318.0772.

8-Aza-6-chloro-4-hydroxy-3-phenylquinolin-2(1H)-one (145)

KHMDS (2.60 mL of 0.5M soln. in toluene) was placed in a 10 mL round-bottom flask under nitrogen. The solution was cooled to −78° C. (acetone/dry ice). After 15 min, a solution of ethyl 5-chloro-2-(phenylacetamido)nicotinate (144) (103.4 mg, 0.3244 mmol) in dry THF (5.0 mL) was added via syringe. The resulting mixture was stirred under nitrogen and allowed to warm to room temperature by letting the cooling bath evaporate. The mixture was stirred at room temperature overnight. The reaction mixture was quenched with water (5 mL) and washed with EtOAc (2×5 mL). The aqueous layer was acidified to pH<2 by the addition of 4N HCl (~5 drops). The resulting mixture was filtered and the filter cake was washed with water (5 mL). The solid was dried (45° C. for 1 h) to leave the title compound as an off-white solid (66.4 mg, 75.1%), mp 324°–6° C. (dec.); $^1$H NMR (DMSO-d$_6$): δ7.36 (m, 5, phenyl), 8.35 (d, J=2.1, 1, py), 8.55 (d, J=2.1, 1, py), 10.64 (bm, 1, OH), 12.05 (s, 1, NH); IR (KBr): 3434, 3134, 1661, 1559, 1402, 1341, 1232, 1143, 673, 564; HPLC: 100%; LRMS: 274 (30), 273 (45), 272 (M+, 100), 271 (90), 215 (10), 157 (10) 155 (35), 127 (20), 89 (15), 77 (10), 63 (10), 51 (10), 39 (10); HRMS Calcd: 272.0352. Found: 272.0349.

Example 19

Preparation of 8-Aza-6-chloro-4-hydroxy-3-(3'-phenoxy)phenylquinolin-2(1H)-one (147)

Ethyl 5-Chloro-2-(3-phenoxyphenylacetamido)nicotinate (146)

To a solution of 3-phenoxyphenylacetic acid (958.8 mg, 4.201 mmol) in dry CH$_2$Cl$_2$ (9.0 mL) in a 25 mL round-bottom flask with stirring under nitrogen was added oxalyl chloride (0.75 mL, d=1.455, 8.6 mmol). The yellow solution was stirred at room temperature under nitrogen for 23 h. Rota-evaporation of the solvent left the acid chloride as a yellow oil, 812 mg (78.4%); $^1$H NMR (CDCl$_3$): 4.12 (s, 2, benzylic), 7.20 (m, 9, phenyl); pure by NMR. This material was used in the next reaction without further characterization or purification.

To a mixture of ethyl 2-amino-5-chloronicotinate (143, Example 18) (344.9 mg, 1.719 mmol) in pyridine (2.0 mL, distilled) in a 10 mL round-bottom flask with stirring was added a solution of 3-phenoxyphenylacetyl chloride (812.5 mg, 3.293 mmol) in dry CH$_2$Cl$_2$ (2.0 mL). The mixture was gradually heated to reflux (130° C., oil bath), over which time the CH$_2$Cl$_2$ was allowed to evaporate. The resulting solution was refluxed for 3.5 h, then cooled to room temperature. The reaction mixture was quenched with water (10 mL) and extracted with chloroform (3×15 mL). The combined organic extracts were washed with water (3×10 mL), dried (MgSO$_4$), and rota-evaporated to dryness, leaving a dark green liquid. This liquid was chromatographed on silica gel (24 g, Mallinckrodt, grade 62, mesh 60–200) and eluted with hexanes-EtOAc (1:4, 250 mL). The desired fractions were collected (R$_f$=0.83) and rota-evaporated to dryness, leaving a green oil. This oil eventually precipitated out as a wet green mass. Crystallization from ethanol afforded the title compound as a light brown flakes, 114 mg (16.1%), mp 103°–4° C.; $^1$H NMR (CDCl$_3$): δ1.39 (t, J=7.2, 3, CH$_3$CH$_2$), 3.88 (s, 2, benzylic), 4.35 (q, J=7.2, 2, CH$_3$CH$_2$O), 7.10 (m, 9, phenyl), 8.24 (d, J=2.4, 1, py), 8.52 (d, J=2.4, 1, py), 10.70 (d, J=2.4, 1, NH); IR (KBr): 3434, 3155, 2925, 1722, 1659, 1401, 1252, 1205, 1102, 775, 700; HPLC: 99%; LRMS: 410 (M$^+$, 40), 211 (35), 210 (100), 200 (35), 183 (30), 181 (40), 128 (15), 89 (50), 77 (20), 51 (15); HRMS Calcd: 410. 1033. Found: 410.1026.

8-Aza-6-chloro-4-hydroxy-3-(3'-phenoxy)phenylquinolin-2 (1H)-one (147)

KHMDS (1.92 mL of 0.5M soln. in toluene) was placed in a 10 mL round-bottom flask under nitrogen. The solution was cooled to −78° C. (acetone/dry ice). After 15 min, a solution of ethyl 5-chloro-2-(3-phenoxyphenylacetamido) nicotinate (146) (98.3 mg, 0.239 mmol) in dry THF (5.0 mL) was added via syringe. The resulting mixture was stirred under nitrogen and allowed to warm to room temperature by letting the cooling bath evaporate. The mixture was stirred at room temperature overnight. The reaction mixture was quenched with water (5 mL) and washed with EtOAc (2×5 mL). The aqueous layer was acidified to pH<2 by the addition of 4N HCl (~7 drops). The resulting mixture was filtered and the filter cake washed with water (2×5 mL). The solid was dried (air) to leave the title compound as a yellow solid. Crystallization from hot DMSO afforded pure compound (27.5 mg, 31.5%), mp 237°–40° C. (dec.); $^1$H NMR (DMSO-d$_6$): δ7.10 (m, 9, phenyl), 8.33 (d, J=2.0, 1, py), 8.54 (d, J=2.0, 1, py), 10.70 (m, 1, OH), 12.04 (s, 1, NH); IR (KBr): 3434, 3155, 1641, 1409, 1218, 1136, 1096; HPLC: 98.0%; LRMS: 366 (25), 365 (45), 364 (M$^+$, 80), 363 (100), 214 (30), 169 (15), 168 (10), 155 (15), 141 (15), 127 (15), 78 (30), 77 (30), 63 (40), 51 (30), 45 (10), 39 (10); HRMS Calcd: 364. 0615. Found: 364.0606.

Example 20

Preparation of 8-Aza-4-hydroxy-3-(3'-phenoxy)phenyl-quinolin-2(1H)-one (149)

Ethyl 2-(3-Phenoxyphenylacetamido)nicotinate (148)

To a solution of 3-phenoxyphenylacetic acid (1 g, 4 mmol) in dry CH$_2$Cl$_2$ (10.0 mL) in a 25 mL round-bottom flask with stirring under nitrogen was added oxalyl chloride (0.75 mL, d=1.455, 8.6 mmol). The yellow solution was stirred at room temperature under nitrogen for 23 h. Rota-evaporation of the solvent left the acid chloride as a yellow oil, 1.0981 g (quant.); $^1$H NMR (CDCl$_3$): 4.11 (s, 2, benzylic), 7.10 (m, 9, phenyl); pure by NMR. This material was used in the next reaction without further characterization or purification.

Ethyl 2-aminonicotinate (121, Example 4) (367.3 mg, 2.238 mmol) was added to 3-phenoxyphenylacetyl chloride (1.0 g, 4.4 mmol) in a 10 mL round-bottom flask. A stir bar and pyridine (2.0 mL, distilled) were added and the mixture heated to reflux (130° C., oil bath) under nitrogen with stirring for 3 h, then cooled to room temperature. The reaction mixture was quenched with water (10 mL) and extracted with chloroform (3×15 mL). The combined organic extracts were washed with sat. NaHCO$_3$ (3×10 mL) and water (3×10 mL), dried (MgSO$_4$), and rota-evaporated to dryness, leaving a dark residue. This residue was chromatographed on silica gel (24 g, Mallinckrodt, grade 62; mesh 60–200) and eluted with hexanes-EtOAc (1:4, 300 mL). The desired fractions were collected ($R_f$=0.52) and rota-evaporated to dryness, leaving an orange oil. This oil eventually precipitated out as a wet orange mass. Crystallization from ethanol afforded the title compound as yellow flakes, 224 mg (26.5%), mp 90°–1° C.; $^1$H NMR (CDCl$_3$): δ1.39 (t, J=6.8, 3, CH$_3$CH$_2$), 3.83 (s, 2, benzylic), 4.35 (q, J=6.8, 2, CH$_3$CH$_2$O), 7.10 (m, 9, phenyl), 8.29 (dd, J$_1$=1.5, J$_2$=7.8, 1, py), 8.59 (dd, J$_1$=1.5, J$_2$=4.8, 1, py), 10.81 (s, 1, NH); IR (KBr): 3441, 3168, 1723, 1668, 1660, 1549, 1490, 1436, 1409, 1307, 1246, 1211, 1143, 1027, 980, 775, 700; HPLC: 100%; LRMS: 377 (10), 376 (M$^+$, 45), 211 (15), 210 (100), 183 (10), 167 (15), 166 (25), 147 (35), 121 (10), 94 (35), 89 (30), 77 (15), 51 (10), 39 (10); HRMS Calcd: 376.1423. Found: 376.1419.

8-Aza-4-hydroxy-3-(3'-phenoxy)phenylquinolin-2(1H)-one (149)

KHMDS (4.60 mL of 0.5 M soln. in toluene) was placed in a 10 mL round-bottom flask under nitrogen. The solution was cooled to −78° C. (acetone/dry ice). After 15 min, a solution of ethyl 2-(3-phenoxyphenylacetamido)nicotinate (148) (216.3 mg, 0.5747 mmol) in dry THF (4.0 mL) was added via syringe. The resulting mixture was stirred under nitrogen and allowed to warm to room temperature by letting the cooling bath evaporate. The mixture was stirred at room temperature overnight. The reaction mixture was quenched with water (5 mL) and washed with EtOAc (2×5 mL). The aqueous layer was acidified to pH<2 by the addition of 4N HCl (15 drops). The resulting mixture was filtered and the filter cake washed with water (5 mL). The solid was dried (45° C. for 1 h) to leave the title compound as an off-white solid (186 mg, 98.1%), mp 246°–8° C. (dec.); $^1$H NMR (DMSO-d$_6$): δ7.09 (m, 6, phenyl), 7.23 (dd, J$_1$=2.4, J$_2$=7.8, 1, py), 7.38 (m, 3, phenyl), 8.30 (d, J=7.8, 1, py), 8.50 (d, J=2.4, 1, py), 10.52 (bm, 1, OH), 11.81 (s, 1, NH); IR (KBr): 3434, 3127, 1648, 1607, 1498, 1409, 1341, 1246, 1150, 946, 789, 761, 700, 571, 543, 475; HPLC: 100%; LRMS: 332 (15), 331 (75), 330 (M$^+$, 100), 121 (10), 93 (10), 77 (10), 51 (10), 39 (10); HRMS Calcd: 330.1004. Found: 330.1015.

Example 21

Preparation of 5-Aza-7-chloro-4-hydroxyquinolin-2(1H)-one (150)

Ethyl 3-acetamido-5-chloropicolinate (155)

To a solution of ethyl 3-amino-5-chloropicolinate (107) (2.0 g, 10 mmol) in 10 mL of 1,4-dioxane was added 4 mL of acetic anhydride. The resulting solution was allowed to stir at 50° C. for 24 hr. Solvent was evaporated and water (10 mL) was added to the residue. The mixture was neutralized by saturated sodium bicarbonate solution to pH=7. A pale yellow solid was collected by filtration and dried in vacuo, giving 2.0 g (83%) of the product. mp 98°–100° C. $^1$H NMR (CDCl$_3$): δ1.476 (t, J=7.2 Hz, 3H), 4.45 (q, J=7.2 Hz, 3H), 8.352 (d, J=2.1 Hz, 1H), 9.218 (d, J=2.1 Hz, 1H), 11.087 (s, 1H).

5-Aza-7-chloro-4-hydroxyquinolin-2(1H)-one (150)

KHMDS (6.0 mL of 0.5M soln. in toluene) was placed in a 25 mL round-bottom flask with stirring under N$_2$ and cooled to −78° C. (acetone/dry ice). After ~15 min, a solution of ethyl 3-acetamido-5-chloropicolinate (155) (243.0 mg, 1.001 mmol) in dry THF (4.0 mL) was added dropwise via syringe. The reaction was allowed to warm to room temperature and stirred at room temperature for 19 h. The reaction was quenched with water (10 mL) and the mixture washed with EtOAc (2×5 mL). The aqueous layer was acidified to ~pH 5 with 4N HCl (4 drops). The mixture was filtered, leaving a light brown solid. A further precipitate was obtained by adding more 4N HCl (8 drops) to the filtrate. The precipitates were combined to leave the title compound as a light brown solid (152.8 mg, 77.65%). An analytical sample could be obtained by trituration in DMSO, mp 307°–310° C.; $^1$H NMR (DMSO-d$_6$): δ5.86 (s, 1, H-3), 7.66 (s, 1, py), 8.42 (s, 1, py), 11.35 (bm, 1, NH); IR (KBr): 3434, 3134, 2929, 2854, 1682, 1470, 1396, 1239, 1218, 1164, 802; HPLC: 98.2%; LRMS: 198 (35), 196 (M$^+$, 100), 170 (20), 168 (60), 127 (20), 113 (15), 69 (25), 64 (15); HRMS for C$_8$H$_5$ClN$_2$O$_2$: Calcd: 196.0040. Found: 196.0045.

Example 22

Preparation of 5-Aza-7-chloro-4-hydroxy-3-nitroquinolin-2(1H)-one (151)

Glacial acetic acid (2 mL) was added to 5-aza-7-chloro-4-hydroxyquinolin-2(1H)-one (150) (107.0 mg, 0.5443 mmol) in a 10 mL round-bottom flask with stirring. To the suspension was added HNO$_3$ (70%, 0.2 mL, d=1.40, 3 mmol). The orange mixture was heated at 100° C. (oil bath, external) for 1 h, then cooled to room temperature. The mixture was quenched with water (3 mL) and filtered, leaving the title compound as yellow crystals (45.6 mg, 34.7%), mp 252°–4° C. (dec.); $^1$H NMR (DMSO-d$_6$): δ7.74 (s, 1, py), 8.58 (s, 1, py), 12.01 (d, J=1.5, 1, NH); IR (KBr): 3441, 3141, 3004, 2930, 2861, 1675, 1546, 1470, 1402, 1293, 1239, 1157, 1102, 932, 904, 809, 625, 468; HPLC: 100%; LRMS: 243 (25), 241 (M$^+$, 80), 213 (35), 212 (15), 211 (100), 197 (15), 196 (15), 183 (15), 181 (30), 157 (15), 155 (50), 154 (20), 153 (25), 139 (15), 128 (15), 127 (20 ) 126 (15), 125 (15), 114 (15), 112 (50), 103 (15), 91 (25), 76 (30), 73 (20), 65 (15), 64 (45), 52 (25), 38 (25); HRMS for C$_8$H$_4$ClN$_3$O$_4$: Calcd: 240.9890. Found: 240.9888.

Example 23

Preparation of 5-Aza-7-chloro-1,2,3,4-tetrahydroquinolin-2,3,4(1H)-trione-3-oxime (152)

5-Aza-7-chloro-4-hydroxyquinolin-2(1H)-one (150) (86.8 mg, 0.442 mmol) and NaNO$_2$ (94.8 mg, 1.37 mmol) were added to a stirring aqueous solution of NaOH (3.4 mL, 0.2N). The mixture was stirred under N$_2$; the resulting orange solution was cooled in an ice-bath and an aqueous solution of H$_2$SO$_4$ (3.0 mL, 2N) was added dropwise under N$_2$. The resulting mixture was allowed to stir at room temperature for 23 h. The reaction was quenched with water (5 mL) and the resulting mixture filtered. The filter cake was washed with water (5 mL) and dried (air) to leave the title compound as a yellow solid (82.0 mg, 82.2%), mp 246° C. (dec.); $^1$H NMR (DMSO-d$_6$): δ7.56 (s, 1, py), 8.42 (m, 1, py), 11.23 (bm, 1, NH); IR (KBr): 3448, 3216, 3052, 2943, 2854, 1709, 1654, 1593, 1430, 1389, 1218, 1102, 1007, 796, 673; HPLC: 99.1%; LRMS: 227 (30), 225 (M$^+$, 100), 211

(30), 208 (20), 196 (15), 182 (15), 181 (30), 180 (20), 179 (20), 155 (15), 154 (20), 153 (30), 139 (15), 125 (20), 112 (25), 91 (15), 76 (20), 73 (20), 64 (40), 44 (35), 38 (20); HRMS for $C_8H_4ClN_3O_3$: Calcd: 224.9941. Found: 224.9943.

Example 24

Preparation of 5-(N-oxy)aza-7-chloro-4-hydroxy-3-phenylquinolin-2-one

Ethyl 5—Chloro-3-(phenylacetamido)picolinate-1-oxide (154)

Ethyl 5-chloro-3-(phenylacetamido)picolinate (153) was formed by reacting ethyl 3-aminopicolinate and phenacetyl chloride under the conditions described in Example 3. The amide (153) (10.0 mg, 0.0324 mmol) was added to a $CH_2Cl_2$ solution (10 mL) of methyl(trifluoromethyl)dioxirane, generated from 2.5 mL of 1,1,1-trifluoroacetone using the procedure of Mello et al. (Mello et al., *J. Amer. Chem. Soc.* 111:6749–6757 (1989)). The solution was stirred at rt in a bomb protected from light. After 4 days, the solvent was removed and the residue chromatographed by prep TLC (silica GF). Eluting with hexanes-EtOAc (1:4), the band at $R_f$=0.45 was removed and triturated with MeOH (40 mL) overnight. The mixture was filtered and the filtrate rotaevaporated to dryness, leaving a white residue (0.4 mg, 4%). $^1$H NMR (CDCl3): δ1.26 (t, J=7.2, 3, $CH_3CH_2$), 3.75 (s, 2, benzylic), 4.10 (q, J=7.2, 2, $CH_3CH_2O$), 7.37 (m, 5, phenyl), 7.98 (d, J=0.9, 1, py), 8.44 (s, 1, py); LRMS (m/z):336 (5), 335 (5), 334 (M$^+$, 20), 274 (15), 273 (10), 272 (55), 260 (10), 226 (10), 180 (10), 156 (10), 154 (30), 126 (10), 117 (20), 91 (100), 65 (15); HRMS Calcd for $C_{16}H_{15}ClN_2O_4$: 334.0720, Found: 334.0729; HPLC: 77%.

5-(N-oxy)aza-7-chloro-4-hydroxy-3-phenylquinolin-2-one

The title compound is formed by substituting ethyl 5-chloro-3-(phenylacetamido)picolinate-1-oxide (154) for methyl 3-(phenylacetamido)picolinate in the final reaction step of Example 3.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound having one of the formulae:

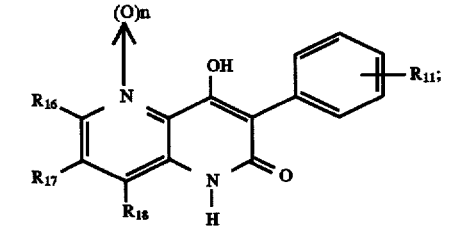

Ie

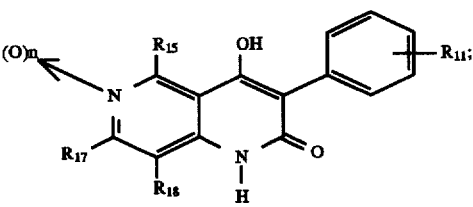

If

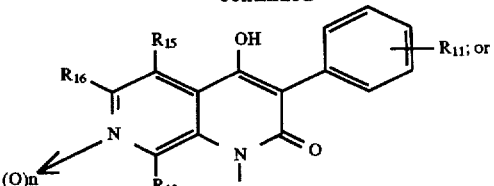

Ig

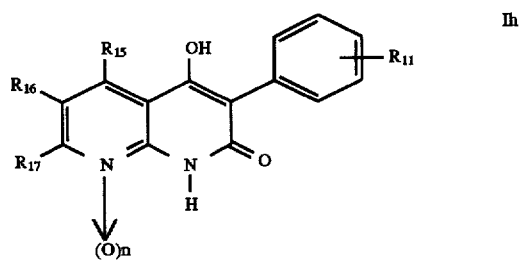

Ih or a tautomer or a pharmaceutically acceptable salt thereof; wherein $R_{15}$ and $R_{16}$ independently represent hydrogen, halogen, cyano, trifluoromethyl, nitro, hydroxy, amino, carboxy, $C_{1-6}$ alkyl, $C_{1-6}$ alkoxy, $C_{1-6}$ alkylthio or $C_{2-6}$ alkoxycarbonyl;

$R_{17}$ represents hydrogen, halogen, cyano, trifluoromethyl, nitro, carboxy, $C_{1-6}$ alkyl, $C_{1-6}$ alkylthio or $C_{2-6}$ alkoxycarbonyl;

$R_{18}$ represents hydrogen or fluorine;

$R_{11}$ represents hydrogen, halogen, cyano, trifluoromethyl, nitro, hydroxy, amino, carboxy, $C_{1-6}$ alkyl, $C_6$-$C_{14}$ aryl($C_{1-6}$)alkyl, $C_6$-$C_{14}$ aryloxy, $C_6$-$C_{14}$ aryl($C_{2-6}$) alkenyl, heteroaryl($C_{1-6}$)alkyl, heteroaryloxy, and heteroaryl($C_{2-6}$)alkenyl, any of which groups may be optionally substituted by hydroxy, halogen, trifluoromethyl, $C_{1-6}$ alkyl, $C_{1-6}$ alkoxy, $C_{1-6}$ alkoxy ($C_{1-6}$)alkoxy, $C_{1-6}$ haloalkyl, phenyl, benzyl or phenoxy, wherein the heteroaryl group in any of said heteroaryl, heteroarylalkyl or heteroarylalkenyl is one of thienyl, pyridyl, or (N-oxy)pyridyl; and n is zero or one.

2. The compound of claim 1 having the formula:

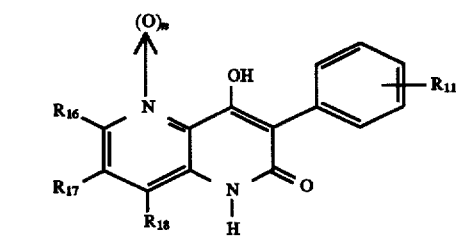

Ie or a tautomer or a pharmaceutically acceptable salt thereof; wherein n and $R_{11}$ are as defined in claim 3;

$R_{18}$ represents hydrogen;

$R_{16}$ represents hydrogen; and $R_{17}$ represents fluoro, chloro, bromo, methyl, trifluoromethyl, or nitro.

3. A compound having the formula:

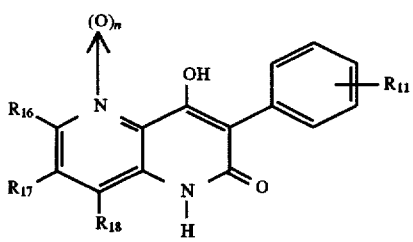

Ic or a tautomer or a pharmaceutically acceptable salt thereof; wherein $R_{16}$ represents hydrogen, halogen, cyano, trifluoromethyl, nitro, hydroxy, amino, carboxy, $C_{1-6}$ alkyl $C_{1-6}$ alkoxy, $C_{1-6}$ alkythio or $C_{2-6}$ alkoxycarbonyl;

$R_{17}$ represents hydrogen, halogen, cyano, trifluoromethyl, nitro, carboxy, $C_{1-6}$ alkyl, $C_{1-6}$ alkylthio or $C_{2-6}$ alkoxycarbonyl;

$R_{18}$ represents hydrogen;

$R_{11}$ represents hydrogen, halogen, cyano, trifluoromethyl, nitro, hydroxy, amino, or carboxy; and n is zero or one.

4. A compound having one of the formulae:

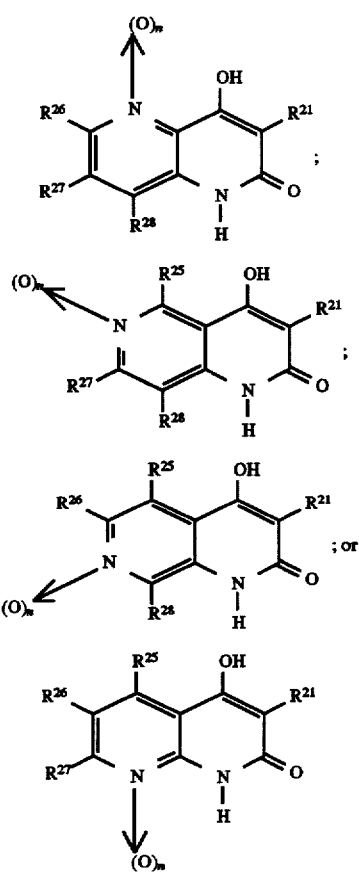

or a tautomer or a pharmaceutically acceptable salt thereof; wherein $R^{21}$ represents —$COR^{23}$ or —$CO_2R^{23}$;

$R^{25}$, $R^{26}$ and $R^{27}$ independently represent hydrogen, halogen, cyano, trifluoromethyl, nitro, hydroxy, amino, carboxy, $C_{1-6}$ alkyl, $C_{1-6}$ alkoxy, or $C_{1-6}$ alkylthio;

$R^{28}$ represents hydrogen or fluorine;

$R^{23}$ represents $C_{3-7}$ cycloalkyl, $C_6-C_{14}$ aryl($C_{1-6}$)alkyl, $C_6-C_{14}$ aryl($C_{2-6}$)alkenyl, $C_6-C_{14}$ aryl($C_{2-6}$)alkynyl, heteroaryl($C_{1-6}$)alkyl, heteroaryl($C_{2-6}$)alkenyl, or heteroaryl($C_{2-6}$)alkynyl, wherein the heteroaryl group in any of said heteroaryl($C_{1-6}$)alkyl, heteroaryl($C_{2-6}$)alkenyl, or heteroaryl($C_{2-6}$)alkynyl is one of indolyl, pyridyl, thienyl, pyridyl or (N-oxy)pyridyl, any of said $R^{23}$ groups may be optionally substituted by one or more of halogen, cyano, trifluoromethyl, nitro, hydroxy, amino, carboxy, $C_{1-6}$ alkyl, $C_{2-6}$ alkenyl, $C_{2-6}$ alkynyl, $C_{3-7}$cycloalkyl, $C_{3-7}$ cycloalkyl($C_{1-6}$)alkyl, $C_6-C_{14}$ aryl, $C_6-C_{14}$ aryloxy, $C_6-C_{14}$ arylthio, $C_6-C_{14}$ aryl($C_{1-6}$)alkyl, $C_{1-6}$ alkoxy, $C_{2-6}$ alkenyloxy, $C_{1-6}$ alkylthio, $C_{1-6}$ alkylsulfinyl, $C_{1-6}$ alkysulfonyl, $C_{2-6}$ alkenylthio, $C_{2-6}$ alkenylthio, $C_{2-6}$ alkylcarbonyl ($C_6-C_{14}$ aryl)carbonyl, $C_{2-6}$ alkoxycarbonyl, $C_{1-6}$alkoxy($C_{1-6}$)alkoxy, $C_{1-6}$ alkoxybenzyl, $C_{1-6}$ alkoxy($C_{1-6}$)alkoxybenzyl or phenoxy; and n is zero or one.

5. A compound of claim 4 having the formula:

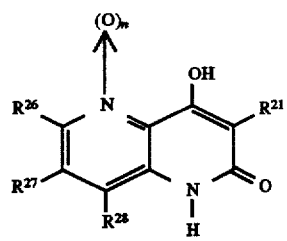

Ii or a tautomer or a pharmaceutically acceptable salt thereof; wherein $R^{21}$ represents —$COR^{23}$ or —$CO_2R^{23}$;

$R^{26}$ and $R^{27}$ independently represent hydrogen, halogen, cyano, trifluoromethyl, nitro, hydroxy, amino, carboxy, $C_{1-6}$ alkyl, $C_{1-6}$ alkoxy, or $C_{1-6}$ alkythio;

$R^{28}$ represents hydrogen;

$R^{23}$ is as defined above in claim 6, and n is zero or one.

6. A compound having one of the formulae:

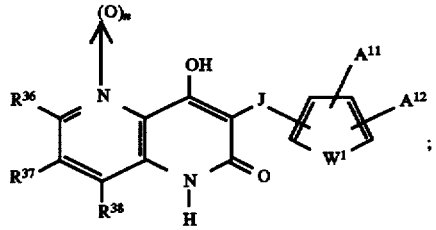

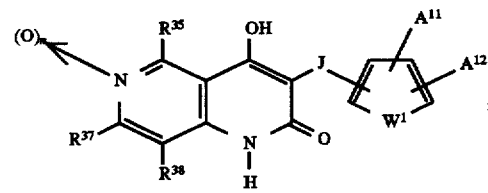

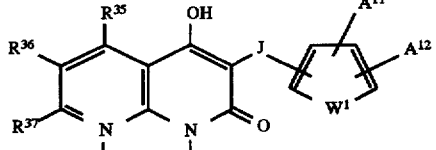

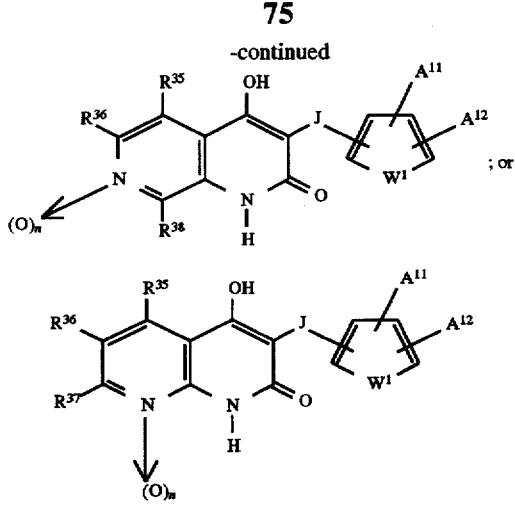

or a tautomer or a pharmaceutically acceptable salt thereof; wherein $W^1$ represents oxygen, sulphur or N—$A^{13}$, $A^{11}$ and $A^{12}$ independently represent hydrogen, halogen, cyano, trifluoromethyl, nitro, hydroxy, amino, carboxy, $C_{1-6}$ alkyl, $C_{2-6}$ alkenyl, $C_{2-6}$ alkynyl, $C_{3-7}$ cycloalkyl, $C_{3-7}$cycloalkyl($C_{1-6}$)alkyl, $C_6$–$C_{14}$ aryl, $C_6$–$C_{14}$ aryl($C_{1-6}$)alkyl, $C_{1-6}$ alkoxy, $C_{2-6}$ alkenyloxy, $C_{1-6}$alkylthio, $C_{2-6}$ alkenylthio, $C_{2-6}$ alkylcarbonyl, $C_6$–$C_{14}$ arylcarbonyl or $C_{2-6}$ alkoxycarbonyl;

$A^{13}$ represents hydrogen, $C_{1-6}$ alkyl or $C_6$–$C_{14}$ aryl($C_{1-6}$)alkyl;

J represents a bond or a carbonyl group;

$R^{38}$ represents hydrogen or fluorine; and $R^{35}$, $R^{36}$ and $R^{37}$ independently represent hydrogen, halogen, cyano, cyanamido, dicyanomethyl, trifluoromethyl, nitro, hydroxy, amino, carboxy, $C_{1-6}$ alkyl, $C_{1-6}$ alkoxy, $C_{1-6}$alkylthio or $C_{2-6}$ alkoxycarbonyl; and n is zero or one.

7. The compound of claim 6 having the formula:

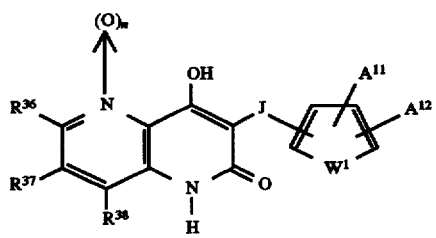

or a tautomer or a pharmaceutically acceptable salt thereof; wherein $W^1$ represents oxygen, sulphur or N—$A^{13}$, $A^{11}$ and $A^{12}$ independently represent hydrogen, halogen, cyano, trifluoromethyl, nitro, hydroxy, amino, carboxy, $C_{1-6}$ alkyl, $C_{2-6}$ alkenyl, $C_{2-6}$ alkynyl, $C_{3-7}$ cycloalkyl, $C_{3-7}$cycloalkyl($C_{1-6}$)alkyl, $C_6$–$C_{14}$ aryl, $C_6$–$C_{14}$ aryl ($C_{1-6}$)alkyl, $C_{1-6}$ alkoxy, $C_{2-6}$ alkenyloxy, $C_{1-6}$alkylthio, $C_{2-6}$ alkenylthio, $C_{2-6}$ alkylcarbonyl, $C_6$–$C_{14}$ arylcarbonyl or $C_{2-6}$ alkoxycarbonyl;

$A^{13}$ represents hydrogen, $C_{1-6}$ alkyl or $C_{6-14}$ aryl($C_{1-6}$)alkyl;

J represents a bond or a carbonyl group;

$R^{38}$ represents hydrogen; and $R^{36}$ and $R^{37}$ independently represent hydrogen, halogen, cyano, cyanamido, dicyanomethyl, trifluoromethyl, nitro, hydroxy, amino, carboxy, $C_{1-6}$ alkyl, $C_{1-6}$ alkoxy, $C_{1-6}$ alkylthio or $C_{2-6}$ alkoxycarbonyl; and n is zero or one.

8. A compound having one of the formulae:

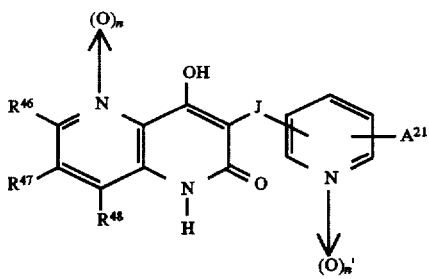

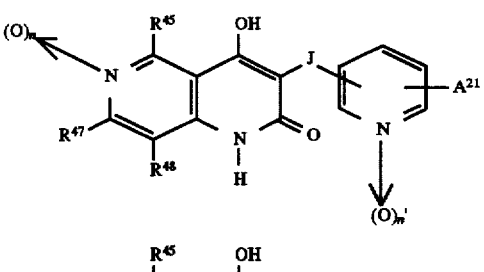

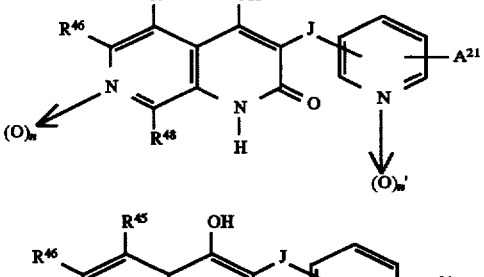

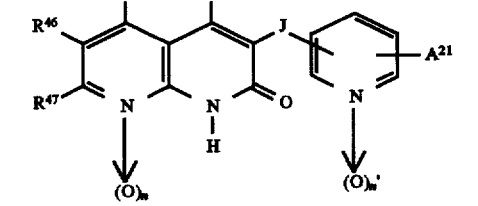

or a tautomer or a pharmaceutically acceptable salt thereof; wherein $A^{21}$ represents hydrogen, halogen, cyano, trifluoromethyl, nitro, hydroxy, amino, carboxy, $C_{1-6}$ alkyl, $C_{1-6}$ alkoxy, $C_{1-6}$ alkylthio, $C_{2-6}$ alkylcarbonyl, $C_6$–$C_{14}$ aryl($C_{1-6}$) alkyl, $C_6$–$C_{14}$ aryloxy, $C_6$–$C_{14}$ aryl($C_{2-6}$)alkenyl, $C_6$–$C_{14}$ aryl($C_{2-6}$)alkynyl, $C_6$–$C_{14}$ arylcarbonyl, or $C_{2-6}$ alkoxycarbonyl, wherein any of said aryl-containing moieties may have up to three substituents selected from the group consisting of hydroxy, halogen, trifluoromethyl, $C_{1-6}$ alkyl, $C_{1-6}$ alkoxy, $C_{1-6}$alkoxy($C_{1-6}$)alkoxy, $C_{1-6}$ haloalkyl, phenyl, benzyl or phenoxy;

J represents a bond or a carbonyl group;

$R^{48}$ represents hydrogen or fluorine;

$R^{45}$, $R^{46}$ and R 47 independently represent hydrogen, halogen, cyano, cyanamido, dicyanomethyl, trifluoromethyl, nitro, hydroxy, amino, carboxy, $C_{1-6}$ alkyl, $C_{1-6}$ alkoxy, $C_{1-6}$ alkylthio or $C_{2-6}$ alkoxycarbonyl, provided that at least one of $R^{45}$, $R^{46}$ and $R^{47}$ is other than hydrogen; and n is zero or one; and n' is zero or one.

9. The compound of claim 8 having the formula:

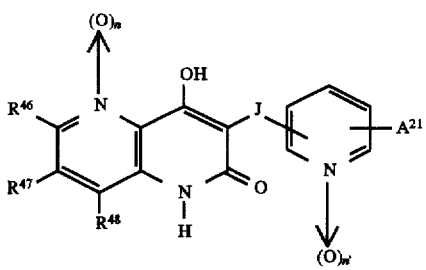

or a tautomer or a pharmaceutically acceptable salt thereof; wherein $A^{21}$ represents hydrogen, halogen, cyano, trifluoromethyl, nitro, hydroxy, amino, carboxy, $C_{1-6}$ alkyl, $C_{1-6}$ alkoxy, $C_{1-6}$ alkylthio, $C_{2-6}$ alkylcarbonyl, $C_6-C_{14}$ aryl($C_{1-6}$) alkyl, $C_6-C_{14}$ aryloxy, $C_6-C_{14}$ aryl($C_{2-6}$alkenyl, $C_6-C_{14}$ aryl($C_{2-6}$)alkynyl, $C_6-C_{14}$ arylcarbonyl, or $C_{2-6}$ alkoxycarbonyl;

J represents a bond or a carbonyl group;

$R^{48}$ represents hydrogen;

$R^{46}$ and $R^{47}$ independently represent hydrogen, halogen, cyano, cyanamido, dicyanomethyl, trifluoromethyl, nitro, hydroxy, amino, carboxy, $C_{1-6}$ alkyl, $C_{1-6}$ alkoxy, $C_{1-6}$ alkylthio or $C_{2-6}$ alkoxycarbonyl, provided that at least one of $R^{45}$, $R^{46}$ and $R^{47}$ is other than hydrogen; and n is zero or one; and n' is zero or one.

10. A compound having one of the following formulae:

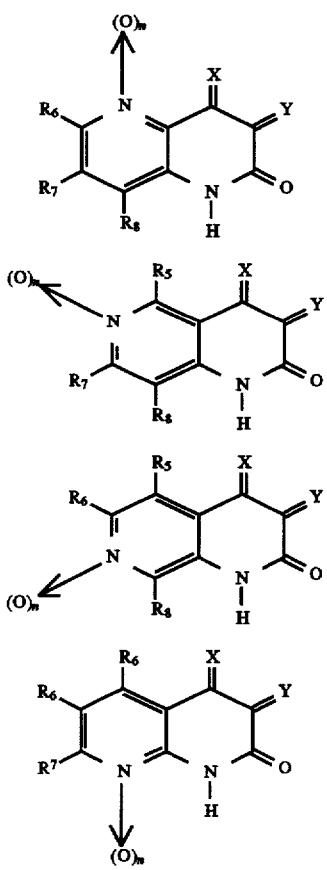

or a tautomer or a pharmaceutically acceptable salt thereof;

wherein $R_5$, $R_6$ and $R_7$ independently represent hydrogen, nitro, amino, halo, $C_{1-4}$ haloalkyl, cyano, cyanamido, dicyanomethyl, hydroxy, carboxy, $C_{1-4}$ alkyl, $C_{3-8}$ cycloalkyl, $C_{2-4}$ alkenyl, $C_{2-4}$ alkynyl, azido, $C_{2-6}$ acylamino, $C_{1-4}$ alkylthio, $C_{1-4}$ alkylsulfonyl, $C_{1-4}$ alkoxy, $C_{3-6}$ trialkylsilyl-substituted ($C_{1-4}$alkoxy, or $C_{1-4}$ haloalkoxy;

$R_8$ represents one of hydrogen or fluorine;

n is zero or one; and one of X or Y is oxygen and the other of X or Y is N—$OR_9$, wherein $R_9$ represents hydrogen, $C_{1-4}$ alkyl, $C_6-C_{14}$ aryl, acyl, halogen-substituted acyl or $C_6-C_{14}$ aryloyl.

11. The compound according to claim 10, wherein X is oxygen, and Y is N—$OR_9$ or a pharmaceutically acceptable salt thereof.

12. The compound according to claim 10, wherein X is N—$OR_9$, and Y is oxygen, or a pharmaceutically acceptable salt thereof.

13. A method of antagonizing excitatory amino acids at the NMDA receptor complex, comprising administering to an animal in need thereof an effective amount of a compound of any one of claims 1, 4, 6 or 8.

14. A method of treating or preventing convulsions, comprising administering to an animal in need of such treatment or prevention an effective amount of a compound of any one of claims 1, 4, 6 or 8.

15. The compound of claim 1, wherein n is zero.

16. The compound of claim 1, wherein n is one.

17. The compound of claim 1, wherein $R_{11}$ is hydrogen, benzyl, phenethyl, hydroxyphenylmethyl, hydroxyphenethyl, phenoxy, methoxyphenylmethyl, methoxymethoxyphenylmethyl, thienylmethyl, thienylvinyl, thienyloxy, pyridylethyl, pyridylmethyl, pyridyloxy, (N-oxy)pyridylmethyl or (N-oxy)pyridyloxy.

18. The compound of claim 4, wherein $R^{23}$ is one of cyclopropyl, benzyl, phenethyl, hydroxyphenethyl, bis(methoxymethoxy)phenethyl, (t-butoxycarbonylaminomethyl)phenethyl, phenylpropyl, hydroxyphenylpropyl, phenylbutyl, hydroxyphenylbutyl, phenylallyl, methoxyphenylallyl, phenylpropargyl, hydroxyphenylpropargyl, methoxyphenylpropargyl, indolylethyl, methoxyindolylethyl, indolylpropyl, thienylethyl, thienylvinyl, pyridylethyl, pyridylpropargyl, (N-oxy)pyridylethyl or (N-oxy)pyridylpropargyl.

19. The compound of claim 4, wherein $R^{25}$, $R^{26}$ and $R^{27}$ are independently selected from hydrogen, halogen, trifluoromethyl, nitro, amino and $C_{1-6}$ alkyl.

20. The compound of claim 6, wherein $A^{11}$ and $A^{12}$ are independently selected from the group consisting of hydrogen, halogen, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$) alkyl, $C_{1-6}$ alkoxy, $C_{2-6}$ alkenyloxy, $C_{1-6}$ alkylthio, $C_{2-6}$ alkenylthio and arylcarbonyl.

21. The compound of claim 6, wherein $A^{11}$ and $A^{12}$ are independently selected from the group consisting of hydrogen, bromo, methyl, ethyl, isopropyl, vinyl, allyl, cyclopropyl, cyclopropylmethyl, phenyl, benzyl, allyloxy, allylthio and benzoyl.

22. The compound of claim 6, wherein $W^1$ is N—$A^{13}$, and $A^{13}$ represents hydrogen or methyl.

23. The compound of claim 6, wherein $R^{35}$, $R^{36}$ and $R^{37}$ are independently selected from hydrogen, halogen, nitro, amino and $C_{1-6}$ alkyl, provided that at least one of $R^{35}$, $R^{36}$ and $R^{37}$ is other than hydrogen.

24. The compound of claim 8, wherein $A^{21}$ is hydrogen.

25. The compound of claim 8, wherein $R^{45}$, $R^{46}$ and $R^{47}$ are independently selected from hydrogen, halogen, nitro, amino and $C_{1-6}$ alkyl, provided that at least one of $R^{35}$, $R^{36}$ and $R^{37}$ is other than hydrogen.

26. The compound of claim 8, wherein J is a bond that attaches the quinolone to the 2-, 3- or 4- position of the pyridine moiety.

27. A compound of any one of claims 1, 4, 6 or 8, wherein n is zero.

28. A compound of any one of claims 1, 4, 6 or 8, wherein n is one.

29. A pharmaceutical composition, comprising a compound of any one of claims 1, 4, 6 or 8, and a pharmaceutically acceptable carrier or diluent.

30. A pharmaceutical composition, comprising a compound of claim 10, and a pharmaceutically acceptable carrier or diluent.

31. A method of antagonizing excitatory amino acids at the NMDA receptor complex, comprising administering to an animal in need thereof an effective amount of a compound of claim 10.

32. A method of antagonizing excitatory amino acids at the NMDA receptor complex, comprising administering to an animal in need thereof an effective amount of a compound having one of the formulae:

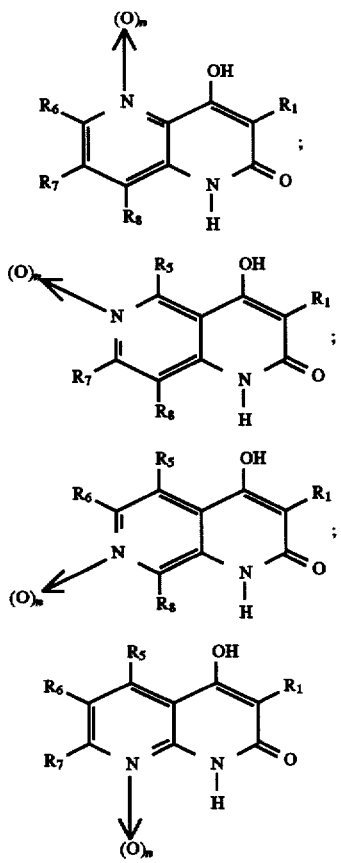

or a tautomer or a pharmaceutically acceptable salt thereof; wherein $R_5$, $R_6$ and $R_7$ independently represent hydrogen, nitro, amino, halo, $C_{1-4}$ haloalkyl, cyano, cyanamido, dicyanomethyl, hydroxy, carboxy, $C_{1-4}$ alkyl, $C_{3-8}$ cycloalkyl, $C_{2-4}$ alkenyl, $C_{2-4}$ alkynyl, azido, $C_{2-6}$ acylamino, $C_{1-4}$ alkylthio, $C_{1-4}$ alkylsulfonyl, $C_{1-4}$ alkoxy, $C_{3-6}$ trialkylsilyl-substituted $(C_{1-4})$alkoxy, or $C_{1-4}$ haloalkoxy;

$R_8$ represents one of hydrogen or fluorine;

n is zero or one;

$R_1$ represents nitro, cyano, trifluoromethyl, trifluoromethylsulfonyl, 1-($C_{2-4}$)alkynyl, —COR, —$CO_2R$, —C(O)SR, cyanamido, tricyanomethyl, —$N(CN)_2$, —$C(CN)_2$—R, —C(=$C(CN)_2$)—R, phenyl, pyridyl, furanyl, thienyl or pyrrolyl, wherein said phenyl, pyridyl, furanyl, thienyl or pyrrolyl can be optionally substituted by one or more of halogen, cyano, trifluoromethyl, nitro, hydroxy, amino, carboxy, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, $C_6$–$C_{14}$ aryl, $C_6$–$C_{14}$ aryloxy, $C_6$–$C_{14}$ arylthio, $C_6$–$C_{14}$ aryl($C_{1-6}$)alkyl, $C_{1-6}$ alkoxy, $C_{2-6}$ alkenyloxy, $C_{1-6}$ alkylthio, $C_{1-6}$ alkylsulfinyl, $C_{1-6}$ alkylsulfonyl, $C_{2-6}$ alkenylthio, $C_{2-6}$ alkenylthio, $C_{2-6}$ alkylcarbonyl, ($C_6$–$C_{14}$ aryl)carbonyl, $C_{2-6}$ alkoxycarbonyl, $C_{1-6}$ alkoxy($C_{1-6}$)alkoxy, $C_{1-6}$ alkoxybenzyl, $C_{1-6}$ alkoxy($C_{1-6}$)alkoxybenzyl or phenoxy; and R represents hydrogen, $C_{1-4}$ alkyl, $C_{2-4}$ alkenyl, $C_{2-4}$ alkynyl, $C_{3-8}$ cycloalkyl, $C_6$–$C_{14}$ aryl($C_{1-6}$)alkyl, $C_6$–$C_{14}$ aryl($C_{2-6}$)alkenyl, $C_6$–$C_{14}$ aryl($C_{2-6}$)alkynyl, pyridyl, furanyl, thienyl or pyrrolyl, any of which groups can be optionally substituted by one or more of halogen, cyano, trifluoromethyl, nitro, hydroxy, amino, carboxy, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, $C_6$–$C_{14}$ aryl, $C_6$–$C_{14}$ aryloxy, $C_6$–$C_{14}$ arylthio, $C_6$–$C_{14}$ aryl($C_{1-6}$) alkyl, $C_{1-6}$ alkoxy, $C_{2-6}$ alkenyloxy, $C_{1-6}$ alkylthio, $C_{1-6}$ alkylsulfinyl, $C_{1-6}$ alkylsulfonyl, $C_{2-6}$ alkenylthio, $C_{2-6}$ alkenylthio, $C_{2-6}$ alkylcarbonyl, ($C_6$–$C_{14}$ aryl)carbonyl, $C_{2-6}$ alkoxycarbonyl, $C_{1-6}$ alkoxy($C_{1-6}$)alkoxy, $C_{1-6}$ alkoxybenzyl, $C_{1-6}$ alkoxy($C_{1-6}$)alkoxybenzyl or phenoxy.

33. A method of treating or preventing convulsions, comprising administering to an animal in need thereof an effective amount of a compound having one of the formulae:

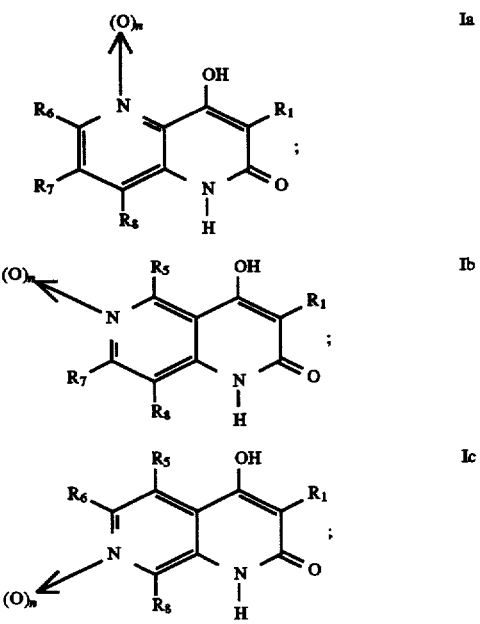

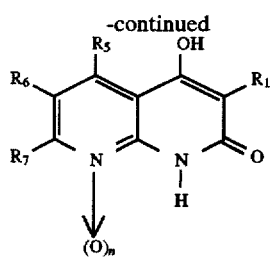

Id or a tautomer or a pharmaceutically acceptable salt thereof; wherein $R_5$, $R_6$ and $R_7$ independently represent hydrogen, nitro, amino, halo, $C_{1-4}$ haloalkyl, cyano, cyanamido, dicyanomethyl, hydroxy, carboxy, $C_{1-4}$ alkyl, $C_{3-8}$ cycloalkyl, $C_{2-4}$ alkenyl, $C_{2-4}$ alkynyl, azido, $C_{2-6}$ acylamino, $C_{1-4}$ alkylthio, $C_{1-4}$ alkylsulfonyl, $C_{1-4}$ alkoxy, $C_{3-6}$ trialkylsilyl-substituted ($C_{1-4}$)alkoxy, or $C_{1-4}$ haloalkoxy;

$R_8$ represents one of hydrogen or fluorine;

n is zero or one;

$R_1$ represents nitro, cyano, trifluoromethyl, trifluoromethylsulfonyl, 1-($C_{2-4}$)alkynyl, —COR, —$CO_2R$, —C(O)SR, cyanamido, tricyanomethyl, —$N(CN)_2$, —$C(CN)_2$—R, —C(=$C(CN)_2$)—R, phenyl, pyridyl, furanyl, thienyl or pyrrolyl, wherein said phenyl, pyridyl, furanyl, thienyl or pyrrolyl can be optionally substituted by one or more of halogen, cyano, trifluoromethyl, nitro, hydroxy, amino, carboxy, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, $C_6$–$C_{14}$ aryl, $C_6$–$C_{14}$ aryloxy, $C_6$–$C_{14}$ arylthio, $C_6$–$C_{14}$ aryl($C_{1-6}$)alkyl, $C_{1-6}$ alkoxy, $C_{2-6}$ alkenyloxy, $C_{1-6}$ alkylthio, $C_{1-6}$ alkylsulfinyl, $C_{1-6}$ alkylsulfonyl, $C_{2-6}$ alkenylthio, $C_{2-6}$ alkenylthio, $C_{2-6}$ alkylcarbonyl, ($C_6$–$C_{14}$ aryl)carbonyl, $C_{2-6}$ alkoxycarbonyl, $C_{1-6}$ alkoxy($C_{1-6}$)alkoxy, $C_{1-6}$ alkoxybenzyl, $C_{1-6}$ alkoxy($C_{1-6}$)alkoxybenzyl or phenoxy; and R represents hydrogen, $C_{1-4}$ alkyl, $C_{2-4}$ alkenyl, $C_{2-4}$ alkynyl, $C_{3-8}$ cycloalkyl, $C_6$–$C_{14}$ aryl($C_{1-6}$)alkyl, $C_6$–$C_{14}$ aryl($C_{2-6}$)alkenyl, $C_6$–$C_{14}$ aryl($C_{2-6}$)alkynyl, pyridyl, furanyl, thienyl or pyrrolyl, any of which groups can be optionally substituted by one or more of halogen, cyano, trifluoromethyl, nitro, hydroxy, amino, carboxy, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, $C_6$–$C_{14}$ aryl, $C_6$–$C_{14}$ aryloxy, $C_6$–$C_{14}$ arylthio, $C_6$–$C_{14}$ aryl($C_{1-6}$)alkyl, $C_{1-6}$ alkoxy, $C_{2-6}$ alkenyloxy, $C_{1-6}$ alkylthio, $C_{1-6}$ alkylsulfinyl, $C_{1-6}$ alkylsulfonyl, $C_{2-6}$ alkenylthio, $C_{2-6}$ alkenylthio, $C_{2-6}$ alkylcarbonyl, ($C_6$–$C_{14}$ aryl)carbonyl, $C_{2-6}$ alkoxycarbonyl, $C_{1-6}$ alkoxy($C_{1-6}$)alkoxy, $C_{1-6}$ alkoxybenzyl, $C_{1-6}$ alkoxy($C_{1-6}$)alkoxybenzyl or phenoxy.

* * * * *